(12) United States Patent
Bayer et al.

(10) Patent No.: US 9,034,609 B2
(45) Date of Patent: May 19, 2015

(54) BIO-ENGINEERED MULTI-ENZYME COMPLEXES COMPRISING XYLANASES AND USES THEREOF

(75) Inventors: Edward A. Bayer, Ramot Hashavim (IL); Yoav Barak, Rehovot (IL); Sarah Morais, Ashdod (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 27 days.

(21) Appl. No.: 13/579,217

(22) PCT Filed: Feb. 15, 2011

(86) PCT No.: PCT/IL2011/000158
§ 371 (c)(1),
(2), (4) Date: Aug. 15, 2012

(87) PCT Pub. No.: WO2011/099015
PCT Pub. Date: Aug. 18, 2011

(65) Prior Publication Data
US 2012/0301930 A1 Nov. 29, 2012

Related U.S. Application Data

(60) Provisional application No. 61/304,500, filed on Feb. 15, 2010.

(51) Int. Cl.
*C12P 19/14* (2006.01)
*C12N 9/42* (2006.01)
*C12N 9/24* (2006.01)

(52) U.S. Cl.
CPC .............. *C12P 19/14* (2013.01); *C12N 9/2434* (2013.01); *C12N 9/248* (2013.01); *C12N 9/2482* (2013.01); *C12P 2203/00* (2013.01); *C12Y 302/01008* (2013.01); *Y02E 50/16* (2013.01)

(58) Field of Classification Search
CPC combination set(s) only.
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,965,188 A | 10/1990 | Mullis |
| 2009/0035811 A1 | 2/2009 | Kohda |
| 2009/0130718 A1 | 5/2009 | Short |
| 2009/0155238 A1 | 6/2009 | Weiner |
| 2009/0220480 A1 | 9/2009 | Gray |
| 2011/0016545 A1 | 1/2011 | Gray |

FOREIGN PATENT DOCUMENTS

| | | |
|---|---|---|
| WO | 97/14789 | 4/1997 |
| WO | 99/25871 | 5/1999 |
| WO | 03/002761 | 1/2003 |
| WO | 2009/045627 | 4/2009 |
| WO | 2010/057064 | 5/2010 |
| WO | 2010/096562 | 8/2010 |

OTHER PUBLICATIONS

Heterologous Production, Assembly, and Secretion of a Minicellulosome by Clostridium acetobutylicum ATCC 824. Applied and Environmental Microbiology, Mar. 2005, vol. 71, No. 3 p. 1215-1222.*
Cha et al. (Effect of multiple copies of cohesins on cellulase and hemicellulase activities of Clostridium cellulovorans mini-cellulosomes. J. Microbiol. Biotechnol. (2007), 17(11), 1782-1788.*
Tuncer et al. Co-operative actions and degradation analysis of purified xylan-degrading enzymes from Thermomonospora fusca BD25 on oat-spelt xylan, J Appl Microbiol. 2003;94(6):1030-5.*
Bachmann, Susan L. and McCarthy, Alan J., "Purification and Cooperative Activity of Enzymes Constituting the Xylan-Degrading System of Thermomonospora fusca", Appl Environ Microbiol, 57(8):2121-2130 (1991).
Barak, Yoav et al., "Matching fusion protein systems for affinity analysis of two interacting families of proteins: the cohesin-dockerin interaction", J Mol Recognit, 18(6):491-501 (2005).
Cantarel, Brandi L. et al., "The Carbohydrate-Active EnZymes database (CAZy): an expert resource for Glycogenomics", Nucleic Acids Res, 37(Database issue):D233-D238. Epub Oct. 5, 2008 (2009).
Caspi, Jonathan et al., "Thermobifida fusca family-6 cellulases as potential designer cellulosome components", Biocat Biotransform 24(1-2):3-12 (2006).
Caspi, Jonathan et al., "Conversion of Thermobifida fusca free exoglucanases into cellulosomal components: comparative impact on cellulose-degrading activity", J Biotechnol, 135(4):351-357 (2008).
Caspi, Jonathan et al., "Effect of linker length and dockerin position on conversion of a Thermobifida fusca endoglucanase to the cellulosomal mode", Appl Environ Microbiol, 75(23)1335-7342 (2009).
Ding, Shi-You et al., "Cellulosomal scaffoldin-like proteins from Ruminococcus flavefaciens", J Bacteriol, 183(6):1945-1953 (2001).
Fierobe, Henri-Pierre et al., "Action of designer cellulosomes on homogeneous versus complex substrates: controlled incorporation of three distinct enzymes into a defined trifunctional scaffoldin", J Biol Chem, 280(16):16325-16334 (2005).
Ghose, T. K. et al., "Measurement of cellulase activities", Pure Appl Chem, 59(2):257-268 (1987).
Haimovitz, Rachel et al., "Cohesin-dockerin microarray: Diverse specificities between two complementary families of interacting protein modules", Proteomics, 8(5):968-979 (2008).
Hespell, R. B. and Cotta, M. A., "Degradation and utilization by Butyrivibrio fibrisolvens H17c of xylans with different chemical and physical properties", Appl Environ Microbiol, 61(8):3042-3050 (1995).

(Continued)

*Primary Examiner* — Kagnew H Gebreyesus
(74) *Attorney, Agent, or Firm* — Rodney J. Fuller; Booth Udall Fuller, PLC

(57) ABSTRACT

The present invention relates to bio-engineered multi-enzyme complexes having synergistic enzyme activity comprising xylanases and optionally further comprising additional carbohydrate active enzymes. Such complexes are advantageous for degrading recalcitrant cellulosic biomass.

14 Claims, 8 Drawing Sheets

(56) References Cited

OTHER PUBLICATIONS

Irwin, Diana C. et al., "Activity studies of eight purified cellulases: Specificity, synergism, and binding domain effects", Biotechnol Bioeng, 42(8):1002-1013 (1993).
Irwin, Diana C. et al., "Characterization and sequence of a Thermomonospora fusca xylanase", Appl Environ Microbiol, 60(3):763-770 (1994).
Irwin, Diana C. et al., "Cloning, expression and characterization of a family 48 exocellulase, Cel48A, from Thermobifida fusca", Eur J Biochem, 267(16):4988-4997 (2000).
Kim, Jeong H. et al., "Purification and characterization of Thermobifida fusca xylanase 10B", Can J Microbiol, 50(10):835-843 (2004).
Koukiekolo, Roger et al., "Degradation of corn fiber by Clostridium cellulovorans cellulases and hemicellulases and contribution of scaffolding protein CbpA", Appl Environ Microbiol, 71(7):3504-3511 (2005).
Miller, G. L. et al., "Use of dinitrosalicylic acid reagent for determination of reducing sugars", Anal Chem, 31(3):426-428 (1959).
Morag, Ely et al., "Expression, purification, and characterization of the cellulose-binding domain of the scaffoldin subunit from the cellulosome of Clostridium thermocellum", Appl Environ Microbiol, 61(5):1980-1986 (1995).
Morais, Sarah et al., "Cellulase-xylanase synergy in designer cellulosomes for enhanced degradation of a complex cellulosic substrate", mBio, 1(5):1-8 (2010).
Murashima, Koichiro et al., "Synergistic effects of cellulosomal xylanase and cellulases from Clostridium cellulovorans on plant cell wall degradation", J Bacteriol, 185(5):1518-1524 (2003).
Nordon, Robert E. et al., "Molecular engineering of the cellulosome complex for affinity and bioenergy applications", Biotechnol Lett, 31(4):465-476 (2009).
Park, J. T. and Johnson, M. J., "A submicrodetermination of glucose", J Biol Chem, 181(1):149-151 (1949).
Tabka, M. G.et al., "Enzymatic saccharification of wheat straw for bioethanol production by a combined cellulase xylanase and feruloyl esterase treatment", Enzyme Microb Technol, 39(4):897-902 (2006).
Tuncer, M. and Ball, A. S., "Co-operative actions and degradation analysis of purified xylan-degrading enzymes from Thermomonospora fusca BD25 on oat-spelt xylan", J Appl Microbiol, 94(6):1030-1035 (2003).
Wang, W. K. et al., "Cloning and DNA sequence of the gene coding for Clostridium thermocellum cellulase Ss (CelS), a major cellulosome component", J Bacteriol, 175(5):1293-1302 (1993).
Wilson, David B. et al., "Studies of Thermobifida fusca plant cell wall degrading enzymes", Chem Rec, 4(2):72-82 (2004).
Xu, Qi et al., "The cellulosome system of Acetivibrio cellulolyticus includes a novel type of adaptor protein and a cell surface anchoring protein", J Bacteriol, 185(15):4548-4557 (2003).
Yaron, Sima et al., "Expression, purification and subunit-binding properties of cohesins 2 and 3 of the Clostridium thermocellum cellulosome", FEBS Lett, 360(2):121-124 (1995).
ISR of PCT/IL2011/000158 Aug. 18, 2011.
Bayer et al., (1994) The cellulosome—A treasure-trove for biotechnology. Trends Biotechnol 12: 378-386.
Bayer et al., (2007) The potential of cellulases and cellulosomes for cellulosic waste management. Curr Opinion Biotechnol 18: 237-245.
Bayer et al., (2008) Cellulosome-enhanced conversion of biomass: On the road to bioethanol, pp. 75-96. In J. Wall, C. Harwood, and A. L Demain (ed.), Bioengergy. ASM Press, Washington, DC.
Bayer et al., (2008) the cellulosome: A natural bacterial strategy to combat biomass recalcitrance, pp. 407-426. In M. E. Himmel (ed.), Biomass Recalcitrance. Blackwell, London.
Berger et al., (2007) Two noncellulosomal cellulases of Clostridium thermocellum, Cel9I and Cel48Y, hydrolyse crystalline cellulose synergistically. FEMS Microbiol Lett 268: 194-201.
Boisset et al., (2000) Imaging the enzymatic digestion of bacterial cellulose ribbons reveals the endo character of the cellobiohydrolase Cel6A from Humicola insolens and its mode of synergy with cellobiohydrolase Cel7A. Appl Environ Microbiol 66: 1444-1452.
Boisset et al., (2001) Optimized mixtures of recombinant Humicola insolens cellulases for the biodegradation of crystalline cellulose. Biotechnol Bioeng 72: 339-45.
Boraston et al., (2004) Carbohydrate-binding modules: fine-tuning polysaccharide recognition. Biochem J 382: 769-781.
Chen and Wilson (2007) Proteomic and transcriptomic analysis of extracellular proteins and mRNA levels in Thermobifida fusca grown on cellobiose and glucose. J Bacteriol 189: 6260-6265.
Fan et al., (2009) Multimeric hemicellulases facilitate biomass conversion. Appl Environ Microbiol 75: 1754-1757.
Fan et al., (2009) The construction and characterization of two xylan-degrading chimeric enzymes. Biotechnol Bioeng 102: 684-692.
Fierobe et al., (1999) Cellulosome from Clostridium cellulolyticum: Molecular study of the dockerin/cohesin interaction. Biochemistry 38: 12822-12832.
Fierobe et al., (2001) Design and production of active cellulosome chimeras: Selective incorporation of dockerincontaining enzymes into defined functional complexes. J Biol Chem 276: 21257-21261.
Fierobe et al., (2002) Degradation of cellulose substrates by cellulosome chimeras: Substrate targeting versus proximity of enzyme components. J Biol Chem 277: 49621-49630.
Ghangas et al., (1989) Cloning of a Thermomonospora fusca xylanase gene and its expression in *Escherichia coli* and Streptomyces lividans. J Bacteriol 171: 2963-2969.
Gilbert and Hazlewood (1993) Bacterial cellulases and xylanases. J Gen Microbiol 139: 187-194.
Hammel et al., (2005) Structural basis of cellulosome efficiency explored by small angle X-ray scattering. J Biol Chem 280: 38562-38568.
Himmel et al., (2007) Biomass recalcitrance: Engineering plants and enzymes for biofuels production. Science 315: 804-807; Erratum: 316: 982.
Jeoh et al., (2002) Cooperative and competitive binding in synergistic mixtures of Thermobifida fusca cellulases Cel5A, Cel6B, and Cel9A. Biotechnol Prog 18: 760-9.
Johnson et al., (1982) Saccharification of complex cellulosic substrates by the cellulase system from Clostridium thermocellum. Appl Environ Microbiol 43: 1125-1132.
Lamed and Bayer (1988) The cellulosome of Clostridium thermocellum. Adv Appl Microbiol 33: 1-46.
Lykidis et al., (2007) Genome sequence and analysis of the soil cellulolytic actinomycete Thermobifida fusca YX. J Bacteriol 189: 2477-86.
Lytle et al., (1996) Interactions of the CelS binding ligand with various receptor domains of the Clostridium thermocellum cellulosomal scaffolding protein, CipA. J Bacteriol 178: 1200-1203.
Mechaly et al., (2000) Overproduction and characterization of seleno-methionine xylanase T-6. J Biotechnol 78: 83-86.
Mingardon et al., (2007) Exploration of new geometries in cellulosome-like chimeras. Appl Environ Microbiol 73: 7138-7149.
Mingardon et al., (2007) Incorporation of fungal cellulases in bacterial minicellulosomes yields viable, synergistically acting cellulolytic complexes. Appl Environ Microbiol 73: 3822-3832.
Morag et al., (1991) Isolation and properties of a major cellobiohydrolase from the cellulosome of Clostridium thermocellum. J Bacteriol 173(13): 4155-62.
Pagès et al., (1997) Species-specificity of the cohesin-dockerin interaction between Clostridium thermocellum and Clostridium cellulolyticum: Prediction of specificity determinants of the dockerin domain. Proteins 29: 517-527.
Pagès et al., (1999) Sequence analysis of scaffolding protein CipC and ORFXp, a new cohesincontaining protein in Clostridium cellulolyticum: comparison of various cohesion domains and subcellular localization of ORFXp. J Bacteriol 181: 1801-1810.
Poole et al., (1992) Identification of the cellulose binding domain of the cellulosome subunit S1 from Clostridium thermocellum. FEMS Microbiol Lett 99: 181-186.
Suurnakki et al., (1997) Hemicellulases in the bleaching of chemical pulps. Adv Biochem Eng Biotechnol 57: 261-287.

(56) References Cited

OTHER PUBLICATIONS

Viikari et al., (1986) Bleaching with enzymes, pp. 67-69. In: Proc. 3rd Int. Conf. Biotechnol. Pulp Paper Ind. Swedish Forest Products Research Laboratory, Stockholm.

Vuong and Wilson (2009) Processivity, synergism, and substrate specificity of Thermobifida fusca Cel6B. Appl Environ Microbiol 75:6655-6661.

Walker et al., (1993) Engineering cellulase mixtures by varying the mole fraction of Thermomonospora fusca E5 and E3, Trichoderma reesei CBHI, and Caldocellum saccharolyticum β-glucosidase. Biotechnol Bioeng 42: 1019-1028.

Bhat (1996) Multiple site-directed mutagenesis. Methods Mol Biol 57: 269-77.

Caruthers et al., (1987) Chemical synthesis of deoxyoligonucleotides by the phosphoramidite method. Methods Enzymol 154: 287-313.

Delagrave et al., (1993) Recursive ensemble mutagenesis. Protein Eng 6(3): 327-31.

Dwivedi et al., (1994) Generation of multiple mutations in the same sequence via the polymerase chain reaction using a single selection primer. Anal Biochem 221(2): 425-8.

Geysen et al., (1984) Use of peptide synthesis to probe viral antigens for epitopes to a resolution of a single amino acid. Proc Natl Acad Sci U S A 81(13): 3998-4002 Ishii et al., (1998) Site-directed mutagenesis. Methods Enzymol 293: 53-71.

Ishii et al., (1998) Site-directed mutagenesis. Methods Enzymol 293: 53-71.

Kegler-Ebo et al., (1994) Codon cassette mutagenesis: a general method to insert or replace individual codons by using universal mutagenic cassettes. Nucleic Acids Res 22(9): 1593-9.

Kim and Maas (2000) Multiple site mutagenesis with high targeting efficiency in one cloning step. Biotechniques 28(2): 196-8.

Kunkel (1985) Rapid and efficient site-specific mutagenesis without phenotypic selection. Proc Natl Acad Sci U S A 82(2): 488-92.

Meetei and Rao (1998) Generation of multiple site-specific mutations in a single polymerase chain reaction product. Anal Biochem 264(2): 288-91.

Merrifield (1963) Solid phase peptide synthesis. I. The synthesis of a tetrapeptide. 85(14): 2149-2154.

Mikaelian and Sergeant (1992) A general and fast method to generate multiple site directed mutations. Nucleic Acids Res 20(2): 376.

Moraïs et al., (2010) Contribution of a xylan-binding module to the degradation of a complex cellulosic substrate by designer cellulosomes. Appl Environ Microbiol 76(12): 3787-96.

Romaniec et al., (1987) Cloning and expression in *Escherichia coli* of Clostridium thermocellum DNA encoding p-glucosidase activity. Enzyme and Microbial Technology 9(8): 474-478.

Weiner et al., (1994) Site-directed mutagenesis of double-stranded DNA by the polymerase chain reaction. Gene 151(1-2): 119-23.

\* cited by examiner

BIO-ENGINEERED MULTI-ENZYME COMPLEXES COMPRISING XYLANASES AND USES THEREOF

RELATED APPLICATION DATA

This application is the U.S. National Stage of International Application No. PCT/IL2011/000158, filed Feb. 15, 2011, which claims the benefit of U.S. Provisional Application No. 61/304,500, filed Feb. 15, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 166,172 byte ASCII (text) file named "Seq_List" created on Aug. 15, 2012.

FIELD OF THE INVENTION

The present invention relates to bio-engineered multi-enzyme complexes comprising at least two xylanases, and optionally other types of carbohydrate active enzymes, designed to attach to a scaffold molecule by the introduction of suitable docking modules. Such complexes are advantageous for degrading recalcitrant cellulosic biomass.

BACKGROUND OF THE INVENTION

When a plurality of enzymes attack their substrates at different sites and create new sites for each other, whereby the resulting activity is higher than the sum of the individual activities, they are said to act synergistically. Enhancing enzyme activity in order to improve industrial processes is one of the most important biotechnological and industrial challenges of recent years. In this context, one group of enzymes that has received much attention is the carbohydrate active enzymes, which is a large group of enzymes that catalyze the breakdown, biosynthesis or modification of carbohydrates and glycoconjugates. Members of this group play an important role in the degradation of cellulosic biomass to soluble sugars that can be converted by microorganisms into liquid fuels, and are therefore of great interest in the fields of bio-energy and bio-fuel production.

The broad group of carbohydrate active enzymes is divided into enzyme classes and further into enzyme families according to a standard classification system (Cantarel et al. 2009 Nucleic Acids Res 37:D233-238). According to this classification system, four enzyme classes are defined, namely glycoside hydrolases, glycosyl transferases, polysaccharide lyases and carbohydrate esterases. Each class includes various enzymatic activities and substrate specificities and is further divided into families numbered in ascending order based on sequence similarities. The different families within each class may display a very broad diversity. For example, one family may contain members from bacteria, fungi, plants and animals, with several different activities and substrate specificities. In addition, a certain activity (for example, a xylanase) may be found in several different families. An informative and updated classification of carbohydrate active enzymes is available on the Carbohydrate-Active Enzymes (CAZy) server.

Typically, carbohydrate active enzymes are characterized by a multi-modular organization, where the catalytic module is associated with one or more ancillary, helper, modules which modulate the enzyme activity. Each module or domain comprises a consecutive portion of the polypeptide chain and forms an independently folding, structurally and functionally distinct unit. One of the main ancillary modules is the carbohydrate-binding module.

The complex structure of cellulosic materials (which may include, for example, cellulose, hemicellulose, lignin) requires cooperation of many types of carbohydrate active enzymes for degradation. Enhancing synergy between carbohydrate active enzymes could lead to improved degradation, and thus has a great impact in the field of energy production from cellulosic biomass.

Synergism has been demonstrated previously between different types of carbohydrate active enzyme, in particular between glycoside hydrolases such as cellulases and xylanases. For example, synergism has been demonstrated between cellulases from different microbial systems (Irwin et al. 1993 Biotechnol. Bioeng. 42:1002-1013), between cellulosomal and non-cellulosomal enzymes (Murashima et al. 2003 J. Bacteriol. 185(5):1518-24, Koukiekolo et al. 2005 Appl Environ Microbiol. 71(7):3504-11), between different types of enzymes from different families and between enzymes that have different substrate-degradation mechanisms (i.e. exoglucanase and endoglucanase).

As another example, synergism has been demonstrated among glycoside hydrolases from the bacterium *Termobifida fusca*, for example, between xylan-degrading enzymes (Bachmann et al. 1991 Appl. Environ. Microbiol. 57:2121-2130, Tuncer et al. 2003 J Appl Microbiol. 94(6):1030-5) and between cellulose-degrading enzymes (Wilson et al. 2004 Chem. Rec. 4:72-82). Attempts in enhancing *T. fusca* enzyme synergism have been undertaken while integrating its enzymes into designer cellulosomes (Caspi et al. 2006 Biocat. Biotransform. 24:3-12).

The cellulosome system is a multi-enzyme complex characterized by a strong bi-modular protein-protein interaction between "cohesin" and "dockerin" modules that integrates the various enzymes into the complex. "Scaffoldin" subunits (non-enzymatic protein components) contain the cohesin modules that incorporate the enzymes into the complex via their resident dockerins. The primary scaffoldin subunit also includes a carbohydrate (cellulose)-binding module (CBM) through which the complex recognizes and binds to the cellulosic substrate. Previous research has suggested that the multi-enzyme cellulosome complex from the bacterium *Clostridium thermocellum* is far more efficient than free cellulase systems that were tested in degrading polysaccharides.

The designer cellulosome concept is based on the very high affinity and specific interaction between cohesin and dockerin modules from the same microorganism species. Since the various scaffoldin-borne cohesins of a given species essentially show the same specificity of binding for the enzyme-borne dockerins, designer cellulosomes are constructed from recombinant chimeric scaffoldins containing divergent cohesins from different species to which matching dockerin-containing enzyme hybrids are prepared. In effect, in designer cellulosomes, enzymes are complexed together on a scaffoldin subunit via the very strong and specific cohesin-dockerin interaction. In such designer cellulosome complexes, enzyme proximity, combined with substrate binding via a carbohydrate-binding module contained in the scaffoldin, resulted in enhanced enzymatic activities in several cases, for example, as described in Fierobe et al. 2005 J. Biol. Chem. 280:16325-16334.

Apart from the designer cellulosome approach, another attempt to increase enzyme synergism has been reported in the form of multifunctional enzyme conjugates. An increase in degradation of natural substrates was observed upon fusing two or three complementary xylan-degrading activities (xylanase, arabinofuranosidase and xylosidase) into the same polypeptide chain. This approach may be cost-reducing, however, strategies involving multifunctional enzyme are limited to small numbers of enzymes and restricted to sub-optimal equimolar ratios of enzymes.

International Patent Application Publication No. WO 1997/014789 discloses an enzymatic array, which composition comprises one or more enzymes non-covalently bound to a peptide backbone, wherein at least one of the enzymes is heterologous to the peptide backbone and the peptide backbone is capable of having bound thereto a plurality of enzymes. The array is useful, for example, in recovery systems, targeted multi-enzyme delivery systems, soluble substrate modification, quantification type assays, and other applications in the food industry, feed, textiles, bioconversion, pulp and paper production, plant protection and pest control, wood preservatives, topical lotions and biomass conversions.

International Patent Application Publication No. WO 2010/057064 discloses designer cellulosomes for efficient hydrolysis of cellulosic material and more particularly for the generation of ethanol.

International Patent Application Publication No. WO 2010/096562 discloses the engineering and expression of heterologous cellulosomes in microorganisms in order to facilitate the conversion of biomass to useful products. In some embodiments, the invention relates to the expression of scaffoldin proteins which form the nucleus of a cellulosome. Cellulases or other biomass-degrading enzymes can be non-covalently linked to the scaffoldin protein by virtue of a dockerin domain-cohesin domain interaction.

U.S. Patent Application Publication Nos. 2009/0155238 and 2011/0016545 disclose enzymes having xylanase, mannanase and/or glucanase activity, e.g., catalyzing hydrolysis of internal β-1,4-xylosidic linkages or endo-β-1,4-glucanase linkages; and/or degrading a linear polysaccharide β-1,4-xylan into xylose. Methods and processes for breaking down hemicellulose, which is a major component of the cell wall of plants, are also disclosed, including methods and processes for hydrolyzing hemicelluloses in any plant or wood or wood product, wood waste, paper pulp, paper product or paper waste or byproduct. In addition, methods of designing new xylanases, mannanases and/or glucanases and methods of use thereof are also disclosed. The xylanases, mannanases and/or glucanases have increased activity and stability at increased pH and temperature.

U.S. Patent Application Publication No. 2009/0220480 discloses polypeptides having any cellulolytic activity, e.g., a cellulase activity, an endoglucanase, a cellobiohydrolase, a beta-glucosidase, a xylanase, a mannanse, a β-xylosidase, an arabinofuranosidase, and/or an oligomerase activity, polynucleotides encoding these polypeptides, and methods of making and using these polynucleotides and polypeptides. The disclosed polypeptides can be used in a variety of pharmaceutical, agricultural, food and feed processing and industrial contexts. Compositions or products of manufacture comprising mixtures of enzymes comprising at least one enzyme of the invention are also disclosed.

There still remains a need for improved degradation of biomass, especially recalcitrant cellulosic biomass. For example, it would be highly beneficial to have bio-engineered, designer cellulosomes showing highly synergistic, improved degradative capabilities.

SUMMARY OF THE INVENTION

The present invention provides bio-engineered multi-enzyme complexes having synergistic enzyme activity comprising xylanases and optionally further comprising additional carbohydrate active enzymes. The combination of different types of enzymatic activities, that work synergistically and in close proximity, may provide a particularly efficient system for degradation of recalcitrant, complex cellulosic biomass.

The present invention discloses for the first time bio-engineered cellulosomes comprising two xylanases having a heterologous dockerin domain, which exhibit enhanced activity, i.e. synergy, of degradation of natural recalcitrant substrates (such as wheat straw) compared to the combined action of the free wild-type enzymes. It is now disclosed that surprisingly, xylanases work synergistically with other xylanases when incorporated into bio-engineered, artificial cellulosomes. It is now disclosed that synergistic activity of xylanases in bio-engineered cellulosomes can be obtained in the case of xylanases that do not naturally include a dockerin domain, and are engineered to include a heterologous dockerin. Further improvement may be achieved when additional carbohydrate active enzymes are added to the complex, including but not limited to cellulases.

The present invention further provides compositions comprising the multi-enzyme complexes and methods for the bioconversion of cellulosic material utilizing same. The present invention further provides cell cultures comprising host cells that produce and secrete the multi-enzyme complexes of the present invention. In some embodiments, a plurality of host cells is present in the culture, each producing at least one component of the multi-enzyme complex.

The present invention further encompasses polypeptides and polynucleotides encoding same comprising components capable of integrating or self-assembling into the bio-engineered complexes of the present invention.

According to one aspect, the present invention provides a bio-engineered multi-enzyme complex comprising:

(i) a scaffold polypeptide comprising a plurality of cohesin domains; and (ii) a plurality of carbohydrate active enzymes bound to said scaffold polypeptide, each carbohydrate active enzyme comprises a dockerin domain;

(iii) wherein the plurality of carbohydrate active enzymes comprises at least two xylanases;

(iv) wherein at least one of the xylanases comprises a heterologous dockerin domain.

As used herein, "plurality" indicates more than one or at least two.

As used herein, "carbohydrate active enzymes" encompass glycoside hydrolases, polysaccharide lyases and carbohydrate esterases.

As used herein, the term "heterologous", when referring to a dockerin domain, indicates either a dockerin that is different from the naturally-occurring dockerin of the enzyme, or a dockerin that is introduced into a polypeptide that does not naturally include a dockerin.

Thus, in some embodiments, at least one of the xylanases present in the complex comprises a dockerin domain which is not the naturally-occurring dockerin domain of this enzyme. According to these embodiments, the at least one xylanase is derived from a wild-type sequence that includes a dockerin, but the variant is engineered to include a different dockerin.

The different dockerin may originate, for example, from a different microorganism species.

In alternative or additional embodiments, at least one of the xylanases present in the complex does not naturally include a dockerin domain. The phrase "does not naturally include a dockerin domain", when referring to a carbohydrate active enzyme, refers to a variant of a carbohydrate active enzyme that is derived from a wild-type sequence that does not include a dockerin domain. The wild-type is therefore unable to incorporate into complexes such as the cellulosome. The variant, however, is engineered to include a dockerin domain and is therefore capable of integrating into the enzyme complex of the present invention.

The enzyme complexes of the present invention are multifunctional. For example, the enzyme complexes may be bi-, tri-, quadri-functional, etc.

Typically, the number of cohesin domains introduced into the scaffold polypeptide is determined according to the number of enzymes to be attached thereto.

The cohesin domains of the scaffold polypeptide may be the same or different. As noted above, the cohesin-dockerin interaction is species specific—scaffoldin-borne cohesins of a given species recognize and interact with enzyme-borne dockerins from the same species. It is therefore possible, in some embodiments, to select the cohesin domains such that each cohesin of the scaffold polypeptide would recognize a different dockerin. In a similar way, the enzymes to be incorporated into the multi-enzyme complex would bear divergent dockerins matching the relevant cohesins.

The individual enzymes that constitute the plurality of carbohydrate active enzymes may be the same or different.

In some embodiments, the dockerin domain included in the carbohydrate active enzymes present in the complex is selected from the group consisting of a dockerin derived from *Clostridium thermocellum*, a dockerin derived from *Acetivibrio cellulolyticus*, a dockerin derived from *Ruminococcus flavefaciens*, a dockerin derived from *Bacteroides cellulosolvens*, a dockerin derived from *Archaeoglobus fulgidus* and a dockerin derived from *Clostridium cellulolyticum*. Each possibility represents a separate embodiment of the invention.

In some embodiments, the dockerin domain included in the carbohydrate active enzymes present in the complex is selected from the group consisting of a dockerin derived from *Clostridium thermocellum*, a dockerin derived from *Acetivibrio cellulolyticus*, a dockerin derived from *Ruminococcus flavefaciens* and a dockerin derived from *Bacteroides cellulosolvens*. Each possibility represents a separate embodiment of the invention.

As noted above, carbohydrate active enzymes are usually characterized by a modular structure, where one or more ancillary or "helper" modules are found in the polypeptide chain in addition to the catalytic module. As used herein, the term "ancillary", when referring to a module of a carbohydrate active enzyme, refers to a non-catalytic module that is present in the enzyme structure in addition to the catalytic module. The ancillary module may modulate the catalytic activity of the enzyme. A non-limiting example of an ancillary module is a carbohydrate-binding module. In some embodiments, the dockerin domain introduced into the carbohydrate active enzymes present in the multi-enzyme complex of the present invention replaces at least one of the ancillary modules originally found in the enzyme structure. In other embodiment, the dockerin domain is introduced in addition to the original ancillary modules.

The xylanases present in the multi-enzyme complex may be classified in any glycoside hydrolase family that include xylanases, as defined in the Carbohydrate-Active Enzymes (CAZy) server and/or CAZypedia.

In some embodiments, the xylanases present in the multi-enzyme complex are classified in a glycoside hydrolase family selected from the group consisting of family 5, 8, 10, 11, 26 and 43. Each possibility represents a separate embodiment of the invention. In some typical embodiments, the xylanases are classified in a glycoside hydrolase family selected from the group consisting of family 10 and 11.

The individual xylanases present in the complex may be classified in the same or different glycoside hydrolase families.

In some embodiments, at least one of the xylanases present in the complex is derived from *Thermobifida fusca* xylanases. In additional embodiments, all xylanases present in the complex are derived from *T. fusca* xylanases. In some embodiments, the *T. fusca* xylanases are selected from the group consisting of Xylanase 10B (Xyn10B) and Xylanase 11A (Xyn11A). Each possibility represents a separate embodiment of the invention. The amino acid sequences of the wild-type Xyn10B (Accession No. AAZ56824.1) and Xyn11A (Accession No. AAA21480.1) are set forth in SEQ ID NOs: 1 and 3, respectively. The DNA encoding wild-type Xyn10B (Accession No. CP000088.1) and Xyn11A (Accession No. U01242.1) are set forth in SEQ ID NOs: 2 and 4, respectively.

In some embodiments, the xylanases present in the complex are selected from the group consisting of a variant Xyn10B comprising a dockerin derived from *C. thermocellum*, and a variant Xyn11A comprising a dockerin derived from *A. cellulolyticus*. Each possibility represents a separate embodiment of the invention. According to these embodiments, the scaffold polypeptide comprises one cohesin domain derived from *C. thermocellum* and one cohesin domain derived from *A. cellulolyticus*.

In some embodiments, the xylanases present in the complex are selected from the group consisting of a variant Xyn10B comprising a sequence homologous to the sequence set forth in SEQ ID NO: 5 and a variant Xyn11A comprising a sequence homologous to the sequence set forth in SEQ ID NO: 7.

As used herein, the degree of homology between a certain reference sequence and its homologous sequence is such that the different functional modules (for example, catalytic module, substrate binding module) are considered to be the same, according to criteria defined in CAZY database and/or CAZYpedia, as detailed above.

In some embodiments, the xylanases present in the complex are selected from the group consisting of a variant Xyn10B comprising the sequence set forth in SEQ ID NO: 5 and a variant Xyn11A comprising the sequence set forth in SEQ ID NO: 7. Each possibility represents a separate embodiment of the invention.

In some embodiments, the plurality of carbohydrate active enzymes present in the complex further comprises at least one carbohydrate active enzyme selected from the group consisting of a glycoside hydrolase, polysaccharide lyase and carbohydrate esterase, wherein the at least one carbohydrate active enzyme is other than a xylanase. Each possibility represents a separate embodiment of the invention.

In some embodiments, the at least one carbohydrate active enzyme is a cellulase. In some embodiments, more than one cellulase is present in the complex, in addition to the xylanases.

In some embodiments, the cellulases are selected from the group consisting of an endocellulase and exocellulase. Each possibility represents a separate embodiment of the invention.

The cellulases present in the multi-enzyme complex may be classified in any glycoside hydrolase family that include cellulases (also referred to as endoglucanases and exoglucanases), as defined in the Carbohydrate-Active Enzymes (CAZy) server and/or CAZypedia.

In some embodiments, the cellulases are classified in a glycoside hydrolase family selected from the group consisting of family 5, 6, 7, 8, 9, 12, 26, 44, 45, 48, 51, 61, and 74. Each possibility represents a separate embodiment of the invention.

The individual cellulases present in the complex may be classified in the same or different glycoside hydrolase families.

In some embodiments, at least one of the cellulases present in the complex is derived from *T. fusca* cellulases. In additional embodiments, all cellulases present in the complex are derived from *T. fusca* cellulases. In some embodiments, the *T. fusca* cellulases are selected from the group consisting of Cellulase 5A (Cel5A) and Cellulase 48A (Cel48A). Each possibility represents a separate embodiment of the invention. The amino acid sequences of the wild-type Cel5A (Accession No. AAZ54939.1) and Cel48A (Accession No. AAD39947.1) are set forth in SEQ ID NOs: 9 and 11, respectively. The DNA encoding wild-type Cel5A (Accession No. CP000088.1) and Cel48A (Accession No. AF144563.1) are set forth in SEQ ID NOs: 10 and 12, respectively.

In some embodiments, the cellulases present in the complex are selected from the group consisting of a variant Cel5A comprising a dockerin derived from *R. flavefaciens*, and a variant Cel48A comprising a dockerin derived from *B. cellulosolvens*. Each possibility represents a separate embodiment of the invention. According to these embodiments, the scaffold polypeptide comprises one cohesin domain derived from *R. flavefaciens* and one cohesin domain derived from *B. cellulosolvens*.

In some embodiments, the cellulases present in the complex are selected from the group consisting of a variant Cel5A comprising a sequence homologous the sequence set forth in SEQ ID NO: 13 and a variant Cel48A comprising a sequence homologous the sequence set forth in SEQ ID NO: 15. Each possibility represents a separate embodiment of the invention.

In some embodiments, the cellulases present in the complex are selected from the group consisting of a variant Cel5A comprising the sequence set forth in SEQ ID NO: 13 and a variant Cel48A comprising the sequence set forth in SEQ ID NO: 15. Each possibility represents a separate embodiment of the invention.

In some embodiments, the bio-engineered multi-enzyme complex is bi-functional. As used herein, "bi-functional", when referring to the enzyme complex, indicates a complex with two enzymes. According to these embodiments, the complex comprises two xylanases, each comprising a dockerin domain.

In some embodiments, one of the two xylanases is derived from *T. fusca* xylanases. In additional embodiments, at least one of the two xylanases is derived from *T. fusca* xylanases. In yet additional embodiments, both xylanases are derived from *T. fusca* xylanases. In some embodiments, the *T. fusca* xylanases are selected from the group consisting of Xyn10B and Xyn11A. Each possibility represents a separate embodiment of the invention.

In some embodiments, the bi-functional complex comprises a variant Xyn10B and a variant Xyn11A, each variant comprises an added dockerin domain.

In some embodiments, the variant Xyn10B comprises a dockerin domain derived from *C. thermocellum* and the variant Xyn11A comprises a dockerin domain derived from *A. cellulolyticus*. According to these embodiments, the scaffold polypeptide comprises one cohesin domain derived from *C. thermocellum* and a second cohesin domain derived from *A. cellulolyticus*.

In some embodiments, the variant Xyn10B comprises an amino acid sequence homologous to the amino acid sequence set forth in SEQ ID NO: 5. In some embodiments, the variant Xyn11A comprises an amino acid sequence homologous to the amino acid sequence set forth in SEQ ID NO: 7.

In some embodiments, the variant Xyn10B comprises the amino acid sequence set forth in SEQ ID NO: 5. In some embodiments, the variant Xyn11A comprises the amino acid sequence set forth in SEQ ID NO: 7.

In some embodiments, the bio-engineered multi-enzyme complex is tri-functional. As used herein, "tri-functional", when referring to the enzyme complex, indicates a complex with three enzymes.

In some embodiments, the tri-functional complex comprises two xylanases and one additional carbohydrate active enzyme selected from the group consisting of a glycoside hydrolase, polysaccharide lyase and carbohydrate esterase, wherein the one additional carbohydrate active enzyme is other than a xylanase. Each possibility represents a separate embodiment of the invention.

In some embodiments, the carbohydrate active enzyme is a cellulase. In some embodiments, the cellulase is an endocellulase. In other embodiments, the cellulase is an exocellulase.

In some embodiments, at least one of the two xylanases and/or the cellulase are derived from *T. fusca* xylanases and cellulases. In additional embodiments, both xylanases and the one cellulase are derived from *T. fusca* xylanases and cellulases.

In some embodiments, the *T. fusca* xylanases are selected from the group consisting of Xyn10B and Xyn11A. Each possibility represents a separate embodiment of the invention.

In some embodiments, the *T. fusca* cellulase is selected from the group consisting of Cel5A and Cel48A. Each possibility represents a separate embodiment of the invention.

In some embodiments, the tri-functional complex comprises a variant Xyn10B, a variant Xyn11A and a variant Cel5A, each variant comprises an added dockerin domain.

In some embodiments, the variant Xyn10B comprises a dockerin domain derived from *C. thermocellum*, the variant Xyn11A comprises a dockerin domain derived from *A. cellulolyticus* and the variant Cel5A comprises a dockerin domain derived from *Ruminococcus flavefaciens*. According to these embodiments, the scaffold polypeptide comprises one cohesin domain derived from *C. thermocellum*, a second cohesin domain derived from *A. cellulolyticus* and a third cohesin derived from *R. flavefaciens*.

In some embodiments, the variant Xyn10B comprises an amino acid sequence homologous to the amino acid sequence set forth in SEQ ID NO: 5. In some embodiments, the variant Xyn11A comprises an amino acid sequence homologous to the amino acid sequence set forth in SEQ ID NO: 7. In some embodiments, the variant Cel5A comprises an amino acid sequence homologous to the amino acid sequence set forth in SEQ ID NO: 13.

In some embodiments, the variant Xyn10B comprises the amino acid sequence set forth in SEQ ID NO: 5. In some embodiments, the variant Xyn11A comprises the amino acid sequence set forth in SEQ ID NO: 7. In some embodiments, the variant Cel5A comprises the amino acid sequence set forth in SEQ ID NO: 13.

In some embodiments, the bio-engineered multi-enzyme complex is quadri-functional. As used herein, "quadri-functional", when referring to the enzyme complex, indicates a complex with four enzymes.

In some embodiments, the quadri-functional complex comprises two xylanases and two additional carbohydrate active enzymes selected from the group consisting of a glycoside hydrolase, polysaccharide lyase and carbohydrate esterase, wherein the two additional carbohydrate active enzymes are other than xylanases. Each possibility represents a separate embodiment of the invention.

In some embodiments, the quadri-functional complex comprises two xylanases and two cellulases. In some typical embodiments, the complex comprises two xylanases, one endocellulase and one exocellulase.

In some embodiments, at least one of the two xylanases and/or at least one of the two cellulases are derived from *T. fusca* xylanases and cellulases. In additional embodiments, both xylanases and both cellulases are derived from *T. fusca* xylanases and cellulases.

In some embodiments, the *T. fusca* xylanases are selected from the group consisting of Xyn10B and Xyn11A. Each possibility represents a separate embodiment of the invention.

In some embodiments, the *T. fusca* cellulases are selected from the group consisting of Cel5A and Cel48A. Each possibility represents a separate embodiment of the invention.

In some embodiments, the quadri-functional complex comprises a variant Xyn10B, a variant Xyn11A, a variant Cel5A and a variant Cel48A, each variant comprises an added dockerin domain.

In some embodiments, the variant Xyn10B comprises a dockerin domain derived from *C. thermocellum*, the variant Xyn11A comprises a dockerin domain derived from *A. cellulolyticus*, the variant Cel5A comprises a dockerin domain derived from *R. flavefaciens* and the variant Cel48A comprises a dockerin domain derived from *Bacteroides cellulosolvens*. According to these embodiments, the scaffold polypeptide comprises one cohesin domain derived from *C. thermocellum*, a second cohesin domain derived from *A. cellulolyticus*, a third cohesin derived from *R. flavefaciens* and a fourth dockerin domain derived from *B. cellulosolvens*.

In some embodiments, the variant Xyn10B comprises an amino acid sequence homologous to the amino acid sequence set forth in SEQ ID NO: 5. In some embodiments, the variant Xyn11A comprises an amino acid sequence homologous to the amino acid sequence set forth in SEQ ID NO: 7. In some embodiments, the variant Cel5A comprises an amino acid sequence homologous to the amino acid sequence set forth in SEQ ID NO: 13. In some embodiments, the variant Cel48A comprises an amino acid sequence homologous to the amino acid sequence set forth in SEQ ID NO: 15.

In some embodiments, the variant Xyn10B comprises the amino acid sequence set forth in SEQ ID NO: 5. In some embodiments, the variant Xyn11A comprises the amino acid sequence set forth in SEQ ID NO: 7. In some embodiments, the variant Cel5A comprises the amino acid sequence set forth in SEQ ID NO: 13. In some embodiments, the variant Cel48A comprises the amino acid sequence set forth in SEQ ID NO: 15.

In some typical embodiments, the scaffold polypeptide further comprises at least one substrate-binding module. In some embodiments, the substrate-binding module is a carbohydrate-binding module (CBM). In some embodiments, the CBM is a cellulose-binding CBM. In other embodiments, the CBM is a xylan-binding CBM. In some embodiments, the CBM is classified in a CBM family selected from the group consisting of family 1, 2 and 3, as defined in the CAZY server and/or CAZYpedia as detailed above. In some embodiments, the CBM is derived from *C. thermocellum* CBMs. In some exemplary embodiments, the *C. thermocellum* CBM is CBM3a.

In some embodiments, the scaffold polypeptide comprises an amino acid sequence selected from the group consisting of the sequences set forth in SEQ ID NOs: 17, 19, 21, 23 and 25. Each possibility represents a separate embodiment of the invention.

In some embodiments, the scaffold polypeptide comprises an amino acid sequence selected from the group consisting of the sequences set forth in SEQ ID NOs: 19, 23 and 25. Each possibility represents a separate embodiment of the invention.

In some typical embodiments, the scaffold polypeptide and each of the carbohydrate active enzymes present in the multi-enzyme complexes of the present invention are non-covalently linked. In additional typical embodiments, they are linked via an interaction between the cohesins present on the scaffold polypeptide and the dockerins present on each of the cellulolytic enzymes.

In other embodiments, the scaffold polypeptide and each of the cellulolytic enzymes are covalently linked. In additional or alternative embodiments, the scaffold polypeptide and each of the cellulolytic enzymes are crosslinked.

According to another aspect, the present invention provides a composition for degrading biomass comprising the multi-enzyme complex of the present invention.

The different components of the multi-enzyme complex of the present invention may be produced from genetically-modified host cells. In some embodiments, each individual component is isolated and the different components are mixed and assembled. In other embodiments, genetically-modified host cells capable of producing and secreting at least one component of the multi-enzyme complex are co-cultured under conditions that allow the secretion and assembly of the different components.

Thus, according to another aspect, the present invention provides a host cell comprising at least one component of the bio-engineered multi-enzyme complex of the present invention.

In some embodiments, a genetically modified host cell is provided, comprising a polynucleotide encoding at least one component of the bio-engineered multi-enzyme complex of the present invention.

In some embodiments, the host cell is selected from a prokaryotic and eukaryotic cell. Each possibility represents a separate embodiment of the invention.

According to a further aspect, the present invention provides a cell culture comprising at least one genetically modified host cell, the host cell comprising at least one component of the multi-enzyme complex of the present invention. The host cells that constitute the culture of the present invention are capable of producing, and typically secreting, at least one component of the multi-enzyme complex of the present invention.

In some embodiments, a cell culture is provided, comprising at least one genetically modified host cell comprising a polynucleotide encoding at least one bio-engineered component of the multi-enzyme complex of the present invention.

In some embodiments, a plurality of different host cells is modified to express and produce at least one component of the multi-enzyme system. According to these embodiments, a plurality of different genetically modified host cells are present in the culture, each comprises at least one component of the multi-enzyme complex.

In other embodiments, a single host cell is genetically modified to express all components of the multi-enzyme complex of the present invention. According to these embodiments, a single host cell is present in the culture, the single host cell comprises all components of the multi-enzyme complex.

The multi-enzyme complexes of the present invention, compositions comprising same and cells cultures producing same may be utilized for the bioconversion of cellulosic material into soluble sugars.

Thus, according to another aspect, the present invention provides a method for bioconversion of cellulosic material into degradation products, the method comprising exposing said cellulosic material to the multi-enzyme complex of the present invention.

In some embodiments, a method for bioconversion of cellulosic material into degradation products is provided, the method comprising exposing said cellulosic material to host cells comprising at least one component of the multi-enzyme system of the present invention.

The degradation products typically comprise mono-, di- and oligosaccharides, including but not limited to glucose, xylose, cellobiose, xylobiose, cellotriose, cellotetraose, arabinose, xylotriose.

According to a further aspect, the present invention provides a system for bioconversion of cellulosic material, the system comprising a multi-enzyme complex of the present invention.

The present invention further provides variant xylanases capable of integrating into the bio-engineered complex of the present invention, and suitable scaffold polypeptides.

Thus, according to another aspect, the present invention provides an isolated polypeptide comprising a variant xylanase, the variant comprises a heterologous dockerin domain.

In some embodiments, the dockerin domain is selected from the group consisting of *C. thermocellum, A. cellulolyticus, R. flavefaciens, B. cellulosolvens, A. fulgidus* and *C. cellulolyticum* dockerins. Each possibility represents a separate embodiment of the invention. In some embodiments, the dockerin domain is selected from the group consisting of *C. thermocellum, A. cellulolyticus, R. flavefaciens* and *B. cellulosolvens*. Each possibility represents a separate embodiment of the invention.

The variant xylanase may be classified in any glycoside hydrolase family that includes xylanases, as defined in the Carbohydrate-Active Enzymes (CAZy) server and/or CAZypedia.

In some embodiments, the variant xylanase is classified in a glycoside hydrolase family selected from the group consisting of family 5, 8, 10, 11, 26 and 43. Each possibility represents a separate embodiment of the invention. In some typical embodiments, the variant xylanase is classified in a glycoside hydrolase family selected from the group consisting of family 10 and 11.

In some embodiments, the variant xylanase is derived from *T. fusca* xylanases.

Xylanases from *T. fusca* does not naturally include a dockerin domain, and the introduction of a dockerin according to embodiments of the present invention enables their utilization and incorporation into enzyme complexes of the present invention.

In some embodiments, the *T. fusca* xylanases are selected from the group consisting of Xyn10B and Xyn11A. Each possibility represents a separate embodiment of the invention.

In some embodiments, the variant *T. fusca* xylanase is selected from the group consisting of a variant Xyn10B comprising a dockerin domain derived from *C. thermocellum* and a variant Xyn11A comprises a dockerin domain derived from *A. cellulolyticus*. Each possibility represents a separate embodiment of the invention.

In some embodiments, the variant *T. fusca* xylanase comprises an amino acid sequence homologous to the amino acid sequence set forth in SEQ ID NO: 5. In some embodiments, the variant *T. fusca* xylanase comprises the amino acid sequence set forth in SEQ ID NO: 5.

In some embodiments, the variant *T. fusca* xylanase comprises an amino acid sequence homologous to the amino acid sequence set forth in SEQ ID NO: 7. In some embodiments, the variant *T. fusca* xylanase comprises the amino acid sequence set forth in SEQ ID NO: 7.

According to another aspect, the present invention provides an isolated scaffold polypeptide comprising a plurality of cohesin domains, wherein the plurality of cohesin domains comprises a cohesin derived from *C. thermocellum*, a cohesin derived from *A. cellulolyticus* and a cohesin derived from *R. flavefaciens*.

In some embodiments, the plurality of cohesin domains is consisting of a cohesin derived from *C. thermocellum*, a cohesin derived from *A. cellulolyticus* and a cohesin derived from *R. flavefaciens*.

In some embodiments, the isolated scaffold polypeptide comprises the amino acid sequence set forth in SEQ ID NO: 23.

According to yet another aspect, the present invention provides an isolated scaffold polypeptide comprising a plurality of cohesin domains, wherein the plurality of cohesin domains comprises a cohesin derived from *C. thermocellum*, a cohesin derived from *A. cellulolyticus*, a cohesin derived from *R. flavefaciens* and a cohesin derived from *B. cellulosolvens*.

In some embodiments, the plurality of cohesin domains is consisting of a cohesin derived from *C. thermocellum*, a cohesin derived from *A. cellulolyticus*, a cohesin derived from *R. flavefaciens* and a cohesin derived from *B. cellulosolvens*.

In some embodiments, the isolated scaffold polypeptide comprises the amino acid sequence set forth in SEQ ID NO: 25.

According to yet another aspect, the present invention provides an isolated scaffold polypeptide comprising at least two cohesin domains, wherein the at least two cohesin domains are selected from the group consisting of:

(i) a cohesin derived from *A. cellulolyticus* and a cohesin derived from *C. thermocellum;*

(ii) a cohesin derived from *B. cellulosolvens* and a cohesin derived from *R. flavefaciens*; and (iii) a cohesin derived from *A. cellulolyticus* and a cohesin derived from *R. flavefaciens*.

In some embodiments, an isolated scaffold polypeptide is provided, comprising a plurality of cohesin domains, wherein the plurality of cohesin domains comprises a cohesin derived from *A. cellulolyticus* and a cohesin derived from *C. thermocellum*. In some embodiments, the plurality of cohesin domains is consisting of a cohesin derived from *A. cellulolyticus* and a cohesin derived from *C. thermocellum*. In some embodiments, the isolated scaffold polypeptide comprises the amino acid sequence set forth in SEQ ID NO: 19.

In some embodiments, an isolated scaffold polypeptide is provided, comprising a plurality of cohesin domains, wherein the plurality of cohesin domains comprises a cohesin derived from *B. cellulosolvens* and a cohesin derived from *R. flavefaciens*. In some embodiments, the plurality of cohesin domains is consisting of a cohesin derived from *B. cellulosolvens* and a cohesin derived from *R. flavefaciens*. In some embodiments, the isolated scaffold polypeptide comprises the amino acid sequence set forth in SEQ ID NO: 21.

In some embodiments, an isolated scaffold polypeptide is provided, comprising a plurality of cohesin domains, wherein the plurality of cohesin domains comprises a cohesin derived from *A. cellulolyticus* and a cohesin derived from *R. flavefaciens*. In some embodiments, the plurality of cohesin domains is consisting of a cohesin derived from *A. cellulolyticus* and a cohesin derived from *R. flavefaciens*. In some embodiments, the isolated scaffold polypeptide comprises the amino acid sequence set forth in SEQ ID NO: 17.

According to another aspect, the present invention provides an isolated polynucleotide comprising a sequence encoding a polypeptide of the present invention.

In some embodiments, the isolated polynucleotide comprises a polynucleotide sequence selected from the group consisting of the sequences set forth in SEQ ID NOs: 6, 8, 18, 20, 22, 24 and 26. Each possibility represents a separate embodiment of the invention.

According to another aspect, the present invention provides a construct comprising a polynucleotide sequence of the present invention. According to yet another aspect, the present invention provides a host cell comprising a polynucleotide sequence of the present invention. In some embodiments, the cell is selected from a prokaryotic and eukaryotic cell.

These and further aspects and features of the present invention will become apparent from the figures, detailed description, examples and claims which follow.

DETAILED DESCRIPTION OF THE INVENTION

Figure 1:
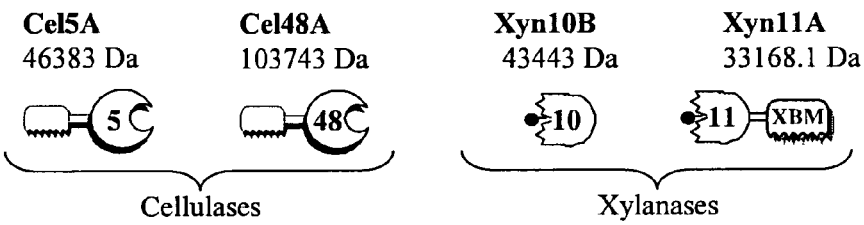
FIG. 1. Schematic representation of the recombinant proteins. The source of the representative module (see key) is indicated as follows: black (*A. cellulolyticum*), white (*C. thermocellum*), dots (*R. flavefasciens*), diagonal stripes (*T. fusca*) and diamonds (*B. cellulosolvens*). In the shorthand notation for the engineered enzymes, the numbers 5, 10, 11 and 48 refer to the corresponding GH family (GH5, GH10, GH11 and GH48) of the catalytic module; upper case characters (B, F, T and A) indicate the source of the cohesin module and lower case (b, f t and a) indicate the source of the dockerin module: *B. cellulosolvens, R. flavefaciens, C. thermocellum* and *A. cellulolyticum* respectively.
Figure 1:
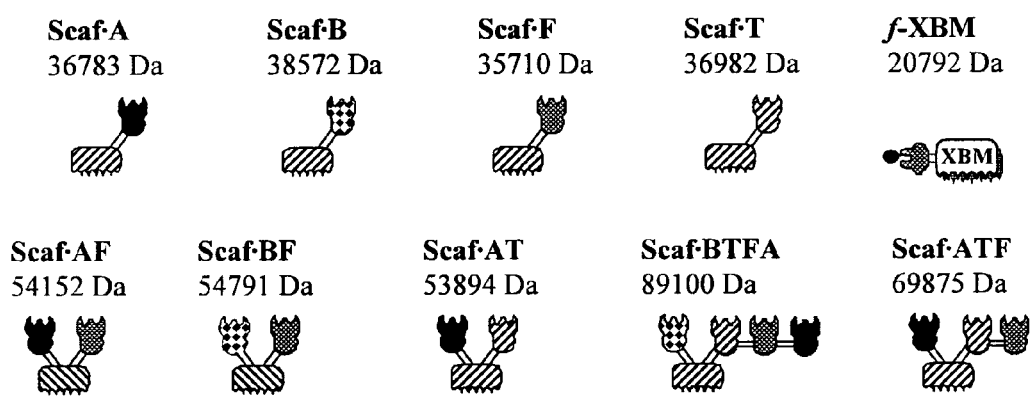
Figure 1:
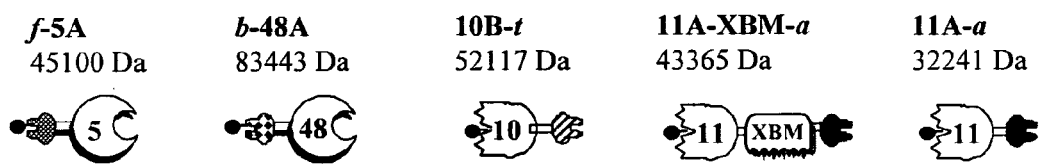
Figure 1:
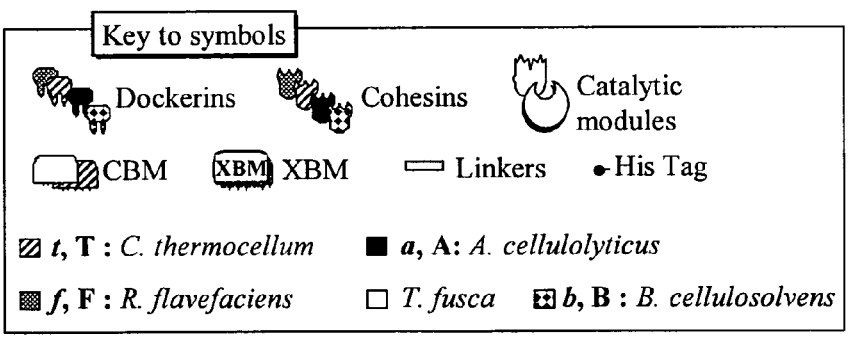

The present invention relates to bio-engineered cellulosomes incorporating at least two xylanases and optionally further comprising other carbohydrate active enzymes. These enzymatic complexes may be useful in the process of bioconversion of cellulosic biomass into soluble sugars.

The present invention is based in part on the unexpected discovery that enhanced synergistic enzymatic activity on raw cellulosic material is observed when two xylanases are bio-engineered to be compatible to the cellulosomal mode via inclusion of a heterologous dockerin domain into at least on of them, and then integrated into artificial cellulosomes. As exemplified hereinbelow, enhanced synergistic enzymatic activity is also observed when the two xylanases are further combined with other carbohydrate active enzymes, such as one or two cellulases, in one artificial cellulosome.

While carbohydrate active enzymes from different classes might theoretically be expected to work synergistically when incorporated into bio-engineered cellulosomes, it was unexpectedly found that synergy is observed between two xylanases incorporated into a bio-engineered cellulosome.

DEFINITIONS

As used herein, the term "enzyme" refers to a polypeptide having a catalytic activity towards a certain substrate or substrates.

As used herein, the term "variant" refers to a protein which differs from an unaltered, wild-type protein due to one or more amino acid substitutions introduced into the amino acid sequence and/or due to the inclusion of sequences/domains not included in the wild-type protein.

The terms "wild type" and "unaltered sequence" are used interchangeably and as used herein refer to the naturally occurring DNA/protein sequence.

As used herein, the term "derived from", when referring to a dockerin or cohesin domain, refers to a variant that has been modified without adversely affecting its ability to recognize the matching cohesin/dockerin, respectively. Typically, the recognition site of the relevant counterpart, also referred to as the binding site, is maintained. When referring to an enzyme, the term "derived from" indicates a variant that has been modified without adversely affecting its catalytic activity. Typically, the catalytic domain is maintained. A derivative generally retains the properties or activity observed in the wild-type to the extent that the derivative is useful for similar purposes as the wild-type form.

As used herein, the term "gene" has its meaning as understood in the art. In general, a gene is taken to include gene regulatory sequences (e.g. promoters, enhancers, etc.) and/or intron sequences, in addition to coding sequences (open reading frames).

As used herein, the term "isolated" means 1) separated from at least some of the components with which it is usually associated in nature; 2) prepared or purified by a process that involves the hand of man; and/or 3) not occurring in nature.

The terms "polypeptide," "peptide" and "protein" are used interchangeably herein to refer to a polymer of amino acid residues.

As used herein, the term "DNA construct" refers to an artificially assembled or isolated nucleic acid molecule which comprises the gene of interest.

As used herein, the term "vector" refers to any recombinant polynucleotide construct that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced.

As used herein, a "primer" defines an oligonucleotide which is capable of annealing to (hybridizing with) a target sequence, thereby creating a double stranded region which can serve as an initiation point for DNA synthesis 5 under suitable conditions.

As used herein, the terms "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

Multi-Enzyme Complexes and Compositions

According to one aspect, the present invention provides a bio-engineered multi-enzyme complex comprising:

(i) a scaffold polypeptide comprising a plurality of cohesin domains; and (ii) a plurality of carbohydrate active enzymes bound to said scaffold polypeptide, each carbohydrate active enzyme comprises a dockerin domain;

(iii) wherein the plurality of carbohydrate active enzymes comprises two xylanases;

(iv) wherein at least one of the xylanases comprises a heterologous dockerin domain.

As noted above, the different carbohydrate active enzymes, as well as the different carbohydrate-binding modules. are classified into classes and families according to a standard classification system. Information about the classification system is available on the Carbohydrate-Active Enzymes (CAZy) server and CAZypedia database. Along with the classification system, a unifying scheme for designating the different catalytic modules and the different carbohydrate active enzymes was suggested and has been widely adopted. A catalytic module is designated by its enzyme class and family number. For example, a glycoside hydrolase having a catalytic module classified in family 10 is designated as "GH10". An enzyme is designated by the type of activity, the family it belongs to and typically an additional letter. For example, a cellulase from a certain organism having a catalytic module classified as family 5 glycoside hydrolase, which is the first reported GH5 cellulase from this organism, is designated as "Cel5A".

Carbohydrate active enzymes according to embodiments of the present invention encompass glycoside hydrolases, polysaccharide lyases and carbohydrate esterases.

As used herein, the term "glycoside hydrolases" refers to enzymes that hydrolyze glycosidic bonds between two or more carbohydrates or between a carbohydrate and a non-carbohydrate moiety. The glycoside hydrolases may catalyze the hydrolysis of O-, N- and/or S-linked glycosides. The glycoside hydrolases are sometimes referred to as glycosidases and glycosyl hydrolases. Non-limiting examples of glycoside hydrolases include a cellulase, xylanase, α-L-arabinofuranosidase, cellobiohydrolase, β-glucosidase, β-xylosidase, β-mannosidase, mannanase.

Information about glycosidic bonds and other types of bonds found in carbohydrate molecules, can be found, for example, in M. L. Sinnott (2007) Carbohydrate Chemistry and Biochemistry: Structure and mechanism, $1^{st}$ edition, Royal Society of Chemistry.

As used herein, the term "polysaccharide lyases" refers to a group of carbon-oxygen lyases that catalyze the breakage of a carbon-oxygen bond in polysaccharides leading to an unsaturated product and the elimination of an alcohol. Typically, polysaccharide lyases cleave uronic acid-containing polysaccharide chains via a β-elimination mechanism, to generate an unsaturated hexenuronic acid residue and a new reducing end. Non-limiting examples of polysaccharide lyases include pectate lyase, alginate lyase.

As used herein, the term "carbohydrate esterases" refers to enzymes that hydrolyze carbohydrate esters. Typically, "carbohydrate esterases" catalyze the de-O or de-N-acylation of substituted saccharides. Non-limiting examples of carbohydrate esterases include acetylxylan esterase, pectin methyl esterase, pectin acetyl esterase, ferulic acid esterases.

The enzyme complexes of the present invention are multi-functional. For example, the enzyme complexes may be bi-, tri-, quadri-functional, etc.

As noted above, mixtures of free carbohydrate active enzymes may show synergistic activity. Further enhancement of the observed synergy (i.e., enhanced synergy) may be obtained when the enzymes are incorporated or self-assembled into multi-enzyme complexes, such as the multi-enzyme complexes of the present invention. Typically, the multi-enzyme complexes of the present invention exhibit enhanced synergy compared to the combined action of the free enzymes.

Thus, multi-enzyme complexes of the present invention typically provide enhanced synergy for the degradation of cellulosic biomass.

Typically, the number of cohesin domains introduced into the scaffold polypeptide is determined according to the number of enzymes to be attached thereto. The cohesin domains of the scaffold polypeptide may be the same or different.

In some embodiments, the cohesin domains are selected such that each cohesin of the scaffold polypeptide would recognize a different dockerin. In a similar way, the enzymes to be incorporated into the multi-enzyme complex would bear divergent dockerins matching the relevant cohesins.

The individual enzymes that constitute the plurality of carbohydrate active enzymes may be the same or different.

In some embodiments, at least one additional enzyme of the plurality of carbohydrate active enzymes present in the multi-enzyme complex comprises a heterologous dockerin domain.

In some embodiments, the dockerin domain included in the carbohydrate active enzymes present in the complex is selected from the group consisting of a dockerin derived from *Clostridium thermocellum*, a dockerin derived from *Acetivibrio cellulolyticus*, a dockerin derived from *Ruminococcus flavefaciens*, a dockerin derived from *Bacteroides cellulosolvens* a dockerin derived from *Archaeoglobus fulgidus* and a dockerin derived from *Clostridium cellulolyticum*. Each possibility represents a separate embodiment of the invention.

In some embodiments, the dockerin domain included in the carbohydrate active enzymes present in the complex is selected from the group consisting of a dockerin derived from *Clostridium thermocellum*, a dockerin derived from *Acetivibrio cellulolyticus*, a dockerin derived from *Ruminococcus flavefaciens* and a dockerin derived from *Bacteroides cellulosolvens*. Each possibility represents a separate embodiment of the invention.

Exemplary amino acid sequences of dockerin domains that can be used according to embodiments of the present invention are set forth in SEQ ID NOs: 27 (from *C. thermocellum*), 29 (from *A. cellulolyticus*), 31 (from *R. flavefaciens*) and 33 (from *B. cellulosolvens*). The sequences of the polynucleotides encoding them are set forth in SEQ ID NOs: 28, 30, 32 and 34, respectively.

In some embodiments, the dockerin domain introduced into the carbohydrate active enzymes present in the multi-enzyme complex of the present invention replaces at least one of the ancillary modules originally found in the enzyme structure. In other embodiment, the dockerin domain is introduced in addition to the original ancillary modules.

The xylanases present in the multi-enzyme complex may be classified in any glycoside hydrolase family that include xylanases, as defined in the Carbohydrate-Active Enzymes (CAZy) server (www.cazy.org) and/or CAZypedia (www.cazypedia.org).

In some embodiments, the xylanases present in the multi-enzyme complex are classified in a glycoside hydrolase family selected from the group consisting of family 5, 8, 10, 11, 26 and 43. Each possibility represents a separate embodiment of the invention. In some typical embodiments, the xylanases are classified in a glycoside hydrolase family selected from the group consisting of family 10 and 11.

Non-limiting examples of additional xylan-degrading enzymes that can be incorporated into the multi-enzyme complex include β-xylosidase, for example β-xylosidase classified in glycoside hydrolase family selected from the group consisting of family 3, 30, 39, 43, 52, 54.

The individual xylanases present in the complex may be classified in the same or different glycoside hydrolase families.

In some embodiments, all xylanases present in the multi-enzyme complex belong to the same family. In other embodiments, the xylanases present in the complex belong to different families.

In some embodiments, at least one of the xylanases present in the complex is derived from *Thermobifida fusca* xylanases. In additional embodiments, all xylanases present in the complex are derived from *T. fusca* xylanases.

*T. fusca* is an aerobic thermophilic soil bacterium with strong cellulolytic activity. This actinomycete produces six different cellulases that have been well studied. *T. fusca* also has the ability to grow on xylan and it produces several enzymes involved in xylan degradation, such as xylanases, β-xylosidase, α-L arabinofuranosidase and acetylesterases.

In some embodiments, the *T. fusca* xylanases are selected from the group consisting of Xylanase 10B (Xyn10B) and Xylanase 11A (Xyn11A). Each possibility represents a separate embodiment of the invention.

*T. fusca* xylanases 11A and 10B are the most abundant xylanases produced by this organism during growth on xylan. They both function as endoxylanases but differ in structure: Xyn11A contains catalytic module followed by a C-terminal family-2 CBM, whereas Xyn10B lacks a CBM.

As exemplified hereinbelow, *T. fusca* xylanases can be engineered to include a dockerin domain and can then be incorporated into enzyme complexes of the present invention.

In some embodiments, the xylanases present in the complex are selected from the group consisting of a variant Xyn10B comprising a dockerin derived from *C. thermocellum*, and a variant Xyn11A comprising a dockerin derived from *A. cellulolyticus*. Each possibility represents a separate embodiment of the invention. According to these embodiments, the scaffold polypeptide comprises one cohesin domain derived from *C. thermocellum* and one cohesin domain derived from *A. cellulolyticus*.

In some embodiments, the xylanases present in the complex are selected from the group consisting of a variant Xyn10B comprising a sequence homologous to the sequence set forth in SEQ ID NO: 5 and a variant Xyn11A comprising a sequence homologous to the sequence set forth in SEQ ID NO: 7.

In some embodiments, the xylanases present in the complex are selected from the group consisting of a variant Xyn10B comprising the sequence set forth in SEQ ID NO: 5 and a variant Xyn11A comprising the sequence set forth in SEQ ID NO: 7. Each possibility represents a separate embodiment of the invention.

In some embodiments, the xylanases present in the complex are selected from the group consisting of a variant Xyn10B consisting of the sequence set forth in SEQ ID NO: 5 and a variant Xyn11A consisting of the sequence set forth in SEQ ID NO: 7. Each possibility represents a separate embodiment of the invention.

In some embodiments, the plurality of carbohydrate active enzymes present in the complex further comprises at least one carbohydrate active enzyme selected from the group consisting of a glycoside hydrolase, polysaccharide lyase and carbohydrate esterase, wherein the at least one carbohydrate active enzyme is other than a xylanase. Each possibility represents a separate embodiment of the invention.

Carbohydrate active enzymes that participate in the degradation of hemicelluloses, a heterogeneous group of branched and linear polysaccharides that are bound via hydrogen bonds to the cellulose microfibrils in the plant cell wall, are sometimes referred to as hemicellulases. Non-limiting examples of such carbohydrate active enzymes include cellulases, xylanases, mannanases, α-L-arabinofuranosidases, ferulic acid esterases, acetyl-xylanesterases, α-D-glucuronidases, β-xylosidases, 3-mannosidases, β-Glucosidases, acetyl-mannanesterases, α-galactosidase, -α-L-arabinanase, β-galactosidase.

In some embodiments, the at least one carbohydrate active enzyme which is further included in the complex is a hemicellulase other than a xylanase. In some exemplary embodiments, the at least one carbohydrate active enzyme is selected from the group consisting of α-L-arabinofuranosidases, β-xylosidase and β-glucosidase. Each possibility represents a separate embodiment of the invention.

In some embodiments, the at least one carbohydrate active enzyme is a cellulase. In some embodiments, more than one cellulase is present in the complex, in addition to the xylanases.

In some embodiments, the cellulases are selected from the group consisting of an endocellulase and exocellulase. Each possibility represents a separate embodiment of the invention. Endocellulases and exocellulases are sometimes referred to as "endoglucanases" and "exoglucanases", respectively.

In some embodiments, the multi-enzyme complex comprises both endocellulases and exocellulases. In other embodiments, only one type of cellulase is present in the complex.

In some embodiments, the ratio between exocellulases and endocellulases in the complex is other than 1:1 ratio. In some embodiments, the exocellulases-to-endocellulases ratio is greater than 1.

The use of scaffold polypeptides bearing several copies of a certain cohesin matching the exocellulases dockerin may be used to modify exocellulases-to-endocellulases ratios within the bio-engineered multi-enzyme complex.

The cellulases present in the multi-enzyme complex may be classified in any glycoside hydrolase family that include cellulases (also referred to as endoglucanases and exoglucanases), as defined in the Carbohydrate-Active Enzymes (CAZy) server and/or CAZypedia.

In some embodiments, the cellulases are classified in a glycoside hydrolase family selected from the group consisting of family 5, 6, 7, 8, 9, 12, 26, 44, 45, 48, 61, and 74. Each possibility represents a separate embodiment of the invention.

The individual cellulases present in the complex may be classified in the same or different glycoside hydrolase families.

In some embodiments, at least one of the cellulases present in the complex is derived from *T. fusca* cellulases. In additional embodiments, all cellulases present in the complex are derived from *T. fusca* cellulases. In some embodiments, the *T. fusca* cellulases are selected from the group consisting of Cellulase 5A (Cel5A) and Cellulase 48A (Cel48A). Each possibility represents a separate embodiment of the invention.

In some embodiments, the cellulases present in the complex are selected from the group consisting of a variant Cel5A comprising a dockerin derived from *R. flavefaciens*, and a variant Cel48A comprising a dockerin derived from *B. cellulosolvens*. Each possibility represents a separate embodiment of the invention. According to these embodiments, the scaffold polypeptide comprises one cohesin domain derived from *R. flavefaciens* and one cohesin domain derived from *B. cellulosolvens*.

In some embodiments, the cellulases present in the complex are selected from the group consisting of a variant Cel5A comprising a sequence homologous the sequence set forth in SEQ ID NO: 13 and a variant Cel48A comprising a sequence homologous the sequence set forth in SEQ ID NO: 15. Each possibility represents a separate embodiment of the invention.

In some embodiments, the cellulases present in the complex are selected from the group consisting of a variant Cel5A comprising the sequence set forth in SEQ ID NO: 13 and a variant Cel48A comprising the sequence set forth in SEQ ID NO: 15. Each possibility represents a separate embodiment of the invention.

In some embodiments, the cellulases present in the complex are selected from the group consisting of a variant Cel5A consisting of the sequence set forth in SEQ ID NO: 13 and a variant Cel48A consisting of the sequence set forth in SEQ ID NO: 15. Each possibility represents a separate embodiment of the invention.

In some embodiments, the bio-engineered multi-enzyme complex is bi-functional. As used herein, "bi-functional", when referring to the enzyme complex, indicates a complex with two enzymes. According to these embodiments, the complex comprises two xylanases, each comprising a dockerin domain.

In some embodiments, one of the two xylanases is derived from *T. fusca* xylanases. In additional embodiments, both xylanases are derived from *T. fusca* xylanases. In some embodiments, the *T. fusca* xylanases are selected from the group consisting of Xyn10B and Xyn11A. Each possibility represents a separate embodiment of the invention.

In some embodiments, the bi-functional complex comprises a variant Xyn10B and a variant Xyn11A, each variant comprises an added dockerin domain.

In some embodiments, the variant Xyn10B comprises a dockerin domain derived from *C. thermocellum* and the variant Xyn11A comprises a dockerin domain derived from *A. cellulolyticus*. According to these embodiments, the scaffold polypeptide comprises one cohesin domain derived from *C. thermocellum* and a second cohesin domain derived from *A. cellulolyticus*.

In some embodiments, the variant Xyn10B comprises an amino acid sequence homologous to the amino acid sequence set forth in SEQ ID NO: 5. In some embodiments, the variant Xyn11A comprises an amino acid sequence homologous to the amino acid sequence set forth in SEQ ID NO: 7.

In some embodiments, the variant Xyn10B comprises the amino acid sequence set forth in SEQ ID NO: 5. In some embodiments, the variant Xyn11A comprises the amino acid sequence set forth in SEQ ID NO: 7.

In some embodiments, the variant Xyn10B is consisting of the amino acid sequence set forth in SEQ ID NO: 5. In some embodiments, the variant Xyn11A is consisting of the amino acid sequence set forth in SEQ ID NO: 7.

In some embodiments, a multi-enzyme complex is provided, wherein the plurality of carbohydrate active enzymes consists of a variant Xyn10B and a variant Xyn11A, each comprises a dockerin domain. In some particular embodiments, the variant Xyn10B comprises the amino acid sequence set forth in SEQ ID NO: 5 and the variant Xyn11A comprises the amino acid sequence set forth in SEQ ID NO: 7.

In some embodiments, the bio-engineered multi-enzyme complex is tri-functional. As used herein, "tri-functional", when referring to the enzyme complex, indicates a complex with three enzymes.

In some embodiments, the tri-functional complex comprises two xylanases and one carbohydrate active enzyme selected from the group consisting of a glycoside hydrolase, polysaccharide lyase and carbohydrate esterase, wherein the one carbohydrate active enzyme is other than a xylanase. Each possibility represents a separate embodiment of the invention.

In some embodiments, the carbohydrate active enzyme is a cellulase.

In some embodiments, the cellulase is an endocellulase. In other embodiments, the cellulase is an exocellulase.

In some embodiments, at least one of the two xylanases and/or the cellulase are derived from *T. fusca* xylanases and cellulases. In additional embodiments, both xylanases and the one cellulase are derived from *T. fusca* xylanases and cellulases.

In some embodiments, the *T. fusca* xylanases are selected from the group consisting of Xyn10B and Xyn11A. Each possibility represents a separate embodiment of the invention.

In some embodiments, the *T. fusca* cellulase is selected from the group consisting of Cel5A and Cel48A. In some embodiments, the *T. fusca* cellulase is Cel5A.

In some embodiments, the tri-functional complex comprises a variant Xyn10B, a variant Xyn11A and a variant Cel5A, each variant comprises an added dockerin domain.

In some embodiments, the variant Xyn10B comprises a dockerin domain derived from *C. thermocellum*, the variant Xyn11A comprises a dockerin domain derived from *A. cellulolyticus* and the variant Cel5A comprises a dockerin domain derived from *Ruminococcus flavefaciens*. According to these embodiments, the scaffold polypeptide comprises one cohesin domain derived from *C. thermocellum*, a second cohesin domain derived from *A. cellulolyticus* and a third cohesin derived from *R. flavefaciens*.

In some embodiments, the variant Xyn10B comprises an amino acid sequence homologous to the amino acid sequence set forth in SEQ ID NO: 5. In some embodiments, the variant Xyn11A comprises an amino acid sequence homologous to the amino acid sequence set forth in SEQ ID NO: 7. In some embodiments, the variant Cel5A comprises an amino acid sequence homologous to the amino acid sequence set forth in SEQ ID NO: 13.

In some embodiments, the variant Xyn10B comprises the amino acid sequence set forth in SEQ ID NO: 5. In some embodiments, the variant Xyn11A comprises the amino acid sequence set forth in SEQ ID NO: 7. In some embodiments, the variant Cel5A comprises the amino acid sequence set forth in SEQ ID NO: 13.

In some embodiments, the variant Xyn10B is consisting of the amino acid sequence set forth in SEQ ID NO: 5. In some embodiments, the variant Xyn11A is consisting of the amino acid sequence set forth in SEQ ID NO: 7. In some embodiments, the variant Cel5A is consisting of the amino acid sequence set forth in SEQ ID NO: 13.

In some embodiments, a multi-enzyme complex is provided, wherein the plurality of carbohydrate active enzymes consists of a variant Xyn10B, a variant Xyn11A and a variant Cel5A, each comprises a dockerin domain. In some particular embodiments, the variant Xyn10B comprises the amino acid sequence set forth in SEQ ID NO: 5, the variant Xyn11A comprises the amino acid sequence set forth in SEQ ID NO: 7 and the variant Cel5A comprises the amino acid sequence set forth in SEQ ID NO: 13.

In some embodiments, the bio-engineered multi-enzyme complex is quadri-functional. As used herein, "quadri-functional", when referring to the enzyme complex, indicates a complex with four enzymes.

In some embodiments, the quadri-functional complex comprises two xylanases and two carbohydrate active enzymes selected from the group consisting of a glycoside hydrolase, polysaccharide lyase and carbohydrate esterase, wherein the two carbohydrate active enzymes are other than xylanases. Each possibility represents a separate embodiment of the invention.

In some embodiments, the quadri-functional complex comprises two xylanases and two cellulases. In some typical embodiments, the complex comprises two xylanases, one endocellulase and one exocellulase.

In some embodiments, at least one of the two xylanases and/or at least one of the two cellulases are derived from *T. fusca* xylanases and cellulases. In additional embodiments, both xylanases and both cellulases are derived from *T. fusca* xylanases and cellulases.

In some embodiments, the *T. fusca* xylanases are selected from the group consisting of Xyn10B and Xyn11A. Each possibility represents a separate embodiment of the invention.

In some embodiments, the *T. fusca* cellulases are selected from the group consisting of Cel5A and Cel48A. Each possibility represents a separate embodiment of the invention.

In some embodiments, the quadri-functional complex comprises a variant Xyn10B, a variant Xyn11A, a variant Cel5A and a variant Cel48A, each variant comprises an added dockerin domain.

In some embodiments, the variant Xyn10B comprises a dockerin domain derived from *C. thermocellum*, the variant Xyn11A comprises a dockerin domain derived from *A. cellulolyticus*, the variant Cel5A comprises a dockerin domain derived from *R. flavefaciens* and the variant Cel48A comprises a dockerin domain derived from *Bacteroides cellulosolvens*. According to these embodiments, the scaffold polypeptide comprises one cohesin domain derived from *C. thermocellum*, a second cohesin domain derived from *A. cellulolyticus*, a third cohesin derived from *R. flavefaciens* and a fourth dockerin domain derived from *B. cellulosolvens*.

In some embodiments, the variant Xyn10B comprises an amino acid sequence homologous to the amino acid sequence set forth in SEQ ID NO: 5. In some embodiments, the variant Xyn11A comprises an amino acid sequence homologous to the amino acid sequence set forth in SEQ ID NO: 7. In some embodiments, the variant Cel5A comprises an amino acid sequence homologous to the amino acid sequence set forth in SEQ ID NO: 13. In some embodiments, the variant Cel48A comprises an amino acid sequence homologous to the amino acid sequence set forth in SEQ ID NO: 15.

In some embodiments, the variant Xyn10B comprises the amino acid sequence set forth in SEQ ID NO: 5. In some embodiments, the variant Xyn11A comprises the amino acid sequence set forth in SEQ ID NO: 7. In some embodiments, the variant Cel5A comprises the amino acid sequence set forth in SEQ ID NO: 13. In some embodiments, the variant Cel48A comprises the amino acid sequence set forth in SEQ ID NO: 15.

In some embodiments, the variant Xyn10B is consisting of the amino acid sequence set forth in SEQ ID NO: 5. In some embodiments, the variant Xyn11A is consisting of the amino acid sequence set forth in SEQ ID NO: 7. In some embodiments, the variant Cel5A is consisting of the amino acid sequence set forth in SEQ ID NO: 13. In some embodiments, the variant Cel48A is consisting of the amino acid sequence set forth in SEQ ID NO: 15.

In some embodiments, a multi-enzyme complex is provided, wherein the plurality of carbohydrate active enzymes consists of a variant Xyn10B, a variant Xyn11A, a variant Cel5A and a variant Cel48A, each comprises a dockerin domain. In some particular embodiments, the variant Xyn10B comprises the amino acid sequence set forth in SEQ ID NO: 5, the variant Xyn11A comprises the amino acid sequence set forth in SEQ ID NO: 7, the variant Cel5A comprises the amino acid sequence set forth in SEQ ID NO: 13 and the Cel48A comprises the amino acid sequence set forth in SEQ ID NO: 15.

The scaffold polypeptide of the present invention is typically a non-catalytic peptide structure which has the ability to have a plurality of enzymes attached thereto.

In some typical embodiments, the scaffold polypeptide further comprises at least one substrate-binding module. In some embodiments, the substrate-binding module is a carbohydrate-binding module (CBM). In some embodiments, the CBM classified in a CBM family selected from the group consisting of family 1, 2 and 3. In some embodiments, the CBM is derived from a thermophilic bacterium. In other embodiments, the CBM is derived from a bacterium other than a thermophilic bacterium. In some embodiments, the CBM is derived from *C. thermocellum* CBMs. In some exemplary embodiments, the *C. thermocellum* CBM is CBM3a.

In some particular embodiments, the scaffold polypeptide comprises an amino acid sequence selected from the group consisting of the sequences set forth in SEQ ID NOs: 17, 19, 21, 23 and 25. Each possibility represents a separate embodiment of the invention.

In some particular embodiments, the scaffold polypeptide comprises an amino acid sequence selected from the group consisting of the sequences set forth in SEQ ID NOs: 19, 23 and 25. Each possibility represents a separate embodiment of the invention.

In some typical embodiments, the scaffold polypeptide and each of the cellulolytic enzymes present in the multi-enzyme complexes of the present invention are non-covalently linked. In additional typical embodiments, they are linked via an interaction between the cohesins present on the scaffold polypeptide and the dockerins present on each of the cellulolytic enzymes.

"Non-covalent bond" or "non-covalently bound" or "non-covalently linked" refer to a molecular interaction which is not the result of a covalent bond. A non-covalent bond includes, for example, hydrophobic attraction, hydrophilic attraction, van der Waals interaction, ionic interaction or any other equivalent molecular interaction which does not involve the formation of a covalent bond.

In other embodiments, the scaffold polypeptide and each of the cellulolytic enzymes are covalently linked. In additional or alternative embodiments, the scaffold polypeptide and each of the cellulolytic enzymes are crosslinked.

The different components of the multi-enzyme complexes of the present invention may be produced by recombinant methods from genetically-modified host cells. The different components may also be prepared by synthetic methods. Exemplary procedures are described below.

In some embodiments, a composition is provided, the composition comprising the multi-enzyme complex of the present invention.

Host Cells and Cell Culture

The different components of the multi-enzyme complex of the present invention may be produced from genetically-modified host cells. In some embodiments, the host cells are grown, each individual component is expressed and isolated, and the different components are mixed and assembled. In other embodiments, genetically-modified host cells capable of producing and secreting at least one component of the multi-enzyme complex are co-cultured under conditions that allow the secretion and assembly of the different components. According to these embodiments, the different components are engineered to include a suitable signal sequence to enable their secretion.

Thus, according to another aspect, the present invention provides a host cell comprising at least one component of the bio-engineered multi-enzyme complex of the present invention.

In some embodiments, a host cell is provided, wherein the host cell is genetically modified to produce at least one component of the multi-enzyme system of the present invention.

In some embodiments, a genetically modified host cell is provided, comprising a polynucleotide encoding at least one bio-engineered component of the multi-enzyme complex of the present invention. In some embodiments, the host cell comprises a combination of polynucleotides that encode more than one component of the multi-enzyme system of the present invention.

In some embodiments, a genetically modified host cell is provided, capable of producing at least one component of the bio-engineered multi-enzyme system of the present invention.

According to a further aspect, the present invention provides a cell culture comprising at least one genetically modified host cell, the host cell comprising at least one component of the multi-enzyme system of the present invention. The host cells that constitute the culture of the present invention are capable of producing and secreting at least one component of the multi-enzyme system of the present invention.

In some embodiments, a cell culture is provided, comprising at least one genetically modified host cell, the at least one genetically modified host cell comprising a polynucleotide encoding at least one bio-engineered component of the multi-enzyme complex of the present invention.

In some embodiments, a plurality of different host cells is modified to express and produce at least one component of the multi-enzyme system. According to these embodiments, a plurality of different genetically modified host cells are present in the culture, each comprises at least one component of the multi-enzyme complex. For example, In some embodiments, each host cell is modified to produce one component of the multi-enzyme system, for example a dockerin-containing enzyme or a scaffold protein. According to these embodiments, the culture comprises a plurality of different types of host cells, each type is modified in a different way and produces a different component of the multi-enzyme complex.

The individual host cells may be from the same or different species.

In some embodiments, a single host cell is modified to produce more than one component of the multi-enzyme system.

In other embodiments, a single host cell is genetically modified to express all components of the multi-enzyme complex of the present invention. According to these embodiments, a single host cell is present in the culture, the single host cell comprises all components of the multi-enzyme complex.

Any host cell known in the art for the production of recombinant proteins may be used for the present invention.

In some embodiments, the host cell is a prokaryotic cell. Representative, non-limiting examples of appropriate prokaryotic hosts include bacterial cells, such as cells of *Escherictahia coli* and *Bacillus subtilis*.

In other embodiments, the host cell is a eukaryotic cell. In some exemplary embodiments, the host cell is a fungal cell, such as yeast. Representative, non-limiting examples of appropriate yeast cells include *Saccharomyces cerevisiae* and *Pichia pastoris*. In additional exemplary embodiments, the host cell is a plant cell.

Genes encoding the different complex components may be cloned into the selected host cells by cloning methods known in the art. Exemplary procedures for cloning and expressing recombinant proteins in host cells are described below.

In the case of secreted proteins, secretion of the different components to the medium may be confirmed, for example by Western blotting. For example, the different components may be engineered to include a certain tag, such as a His-tag, thereby allowing their probing by a suitable antibody.

Host cells secreting the different components are co-cultured and the correct assembly of the multi-enzyme complex may be confirmed, for example by using non-denaturing gel electrophoresis mobility assay. An exemplary procedure is exemplified herein below.

The appropriate culturing conditions that allow expression and secretion of the recombinant proteins are determined according to the particular host cells. Determination of the suitable conditions is within the capabilities of a person skilled in the art.

The activity of transformed host cells or cell cultures, as well as the multi-enzyme complexes may be assayed. For example, cellulase activity can be determined for example, using Avicel as the substrate as is well known to a person skilled in the art and is exemplified herein below. The activity of the secreted components may be assayed on complex substrates, such as wheat straw, as also exemplified herein below.

Methods and Systems for Bioconversion of Cellulosic Material

The multi-enzyme complexes of the present invention, compositions comprising same and cells cultures producing same may be utilized for the bioconversion of cellulosic material into degradation products.

Resulting sugars may be used for the production of alcohols such as ethanol, propanol, butanol and/or methanol, production of fuels, e.g., biofuels such as synthetic liquids or gases, such as syngas, and the production of other fermentation products, e.g. succinic acid, lactic acid, or acetic acid.

Thus, according to another aspect, the present invention provides a method for bioconversion of cellulosic material into degradation products comprising exposing said cellulosic material to the multi-enzyme complex of the present invention.

According to a further aspect, the present invention provides a system for bioconversion of cellulosic material comprising a multi-enzyme complex of the present invention.

Multi-enzyme complexes of the present invention may be added to bioconversion and other industrial processes for example, continuously, in batches or by fed-batch methods. Alternatively or additionally, the multi-enzymes of the invention may be recycled.

By relieving end-product inhibition of endoxylanases and exo/endo-glucanases (such as xylobiose and cellobiose), it may be possible to further enhance the hydrolysis of the cellulosic material.

Polypeptides and Polynucleotides

The present invention further provides variant xylanases capable of integrating into the bio-engineered complex of the present invention, and suitable scaffold polypeptides.

The variant xylanases of the present invention are modified to include a heterologous dockerin. Thus, the variant xylanases are chimeric polypeptides, comprising a xylanase catalytic module and a heterologous dockerin domain.

According to another aspect, the present invention provides an isolated polypeptide comprising a variant xylanase, the variant comprises a heterologous dockerin domain.

In some embodiments, the dockerin domain is selected from the group consisting of *C. thermocellum, A. cellulolyticus, R. flavefaciens, B. cellulosolvens A. fulgidus* and *C. cellulolyticum* dockerins. Each possibility represents a separate embodiment of the invention. In some embodiments, the dockerin domain is selected from the group consisting of *C. thermocellum, A. cellulolyticus, R. flavefaciens* and *B. cellulosolvens*. Each possibility represents a separate embodiment of the invention.

In some embodiments, the variant xylanase is classified in a glycoside hydrolase family selected from the group consisting of family 5, 8, 10, 11, 26 and 43. Each possibility represents a separate embodiment of the invention. In some typical embodiments, the variant xylanase is classified in a glycoside hydrolase family selected from the group consisting of family 10 and 11.

In some embodiments, the variant xylanase is derived from *T. fusca* xylanases.

Xylanases from *T. fusca* does not naturally include a dockerin domain, and the introduction of a dockerin according to embodiments of the present invention enables their utilization and incorporation into enzyme complexes of the present invention.

In some embodiments, the *T. fusca* xylanases are selected from the group consisting of Xyn10B and Xyn11A. Each possibility represents a separate embodiment of the invention.

In some embodiments, the variant *T. fusca* xylanase is selected from the group consisting of a variant Xyn10B comprising a dockerin domain derived from *C. thermocellum* and a variant Xyn11A comprises a dockerin domain derived from *A. cellulolyticus*. Each possibility represents a separate embodiment of the invention.

In some embodiments, the variant *T. fusca* xylanase comprises an amino acid sequence homologous to the amino acid sequence set forth in SEQ ID NO: 5. In some embodiments, the variant *T. fusca* xylanase comprises the amino acid sequence set forth in SEQ ID NO: 5. In some embodiments, the variant *T. fusca* xylanase is consisting of the amino acid sequence set forth in SEQ ID NO: 5.

In some embodiments, the variant *T. fusca* xylanase comprises an amino acid sequence homologous to the amino acid sequence set forth in SEQ ID NO: 7. In some embodiments, the variant *T. fusca* xylanase comprises the amino acid sequence set forth in SEQ ID NO: 7. In some embodiments, the variant *T. fusca* xylanase is consisting of the amino acid sequence set forth in SEQ ID NO: 7.

The variant xylanases may be utilized for the bio-conversion of cellulosic material. In some embodiments, a composition is provided, comprising the variant xylanase of the present invention.

The variant xylanases they may be incorporated into multi-enzyme complexes, such as the bio-engineered complexes described above. Thus, there is provided a bio-engineered multi-enzyme complex comprising a variant xylanase of the present invention. In some embodiments, there is provided a bio-engineered cellulosome comprising a variant xylanase of the present invention.

There is further provided a method for the bio-conversion of cellulosic material into degradation products comprising exposing said cellulosic material to a variant xylanase of the present invention.

There is further provided a system for bioconversion of cellulosic material comprising a variant xylanase of the present invention.

According to another aspect, the present invention provides an isolated scaffold polypeptide comprising a plurality of cohesin domains, wherein the plurality of cohesin domains comprises a cohesin derived from C. thermocellum, a cohesin derived from A. cellulolyticus and a cohesin derived from R. flavefaciens.

It is to be understood the plurality of cohesin domains present in scaffold polypeptides of the present invention may be arranged in any order in the scaffold polypeptide.

In some embodiments, the isolated scaffold polypeptide comprises the amino acid sequence set forth in SEQ ID NO: 23. In some embodiments, the isolated scaffold polypeptide is consisting of the amino acid sequence set forth in SEQ ID NO: 23.

According to yet another aspect, the present invention provides an isolated scaffold polypeptide comprising a plurality of cohesin domains, wherein the plurality of cohesin domains comprises a cohesin derived from C. thermocellum, a cohesin derived from A. cellulolyticus, a cohesin derived from R. flavefaciens and a cohesin derived from B. cellulosolvens.

In some embodiments, the isolated scaffold polypeptide comprises the amino acid sequence set forth in SEQ ID NO: 25. In some embodiments, the isolated scaffold polypeptide is consisting of the amino acid sequence set forth in SEQ ID NO: 25.

According to yet another aspect, the present invention provides an isolated scaffold polypeptide comprising at least two cohesin domains, wherein the at least two cohesin domains are selected from the group consisting of:

(i) a cohesin derived from A. cellulolyticus and a cohesin derived from C. thermocellum;
(ii) a cohesin derived from B. cellulosolvens and a cohesin derived from R. flavefaciens; and
(iii) a cohesin derived from A. cellulolyticus and a cohesin derived from R. flavefaciens.

In some embodiments, an isolated scaffold polypeptide is provided, comprising a plurality of cohesin domains, wherein the plurality of cohesin domains comprises a cohesin derived from A. cellulolyticus and a cohesin derived from C. thermocellum. In some embodiments, the plurality of cohesin domains is consisting of a cohesin derived from A. cellulolyticus and a cohesin derived from C. thermocellum. In some embodiments, the isolated scaffold polypeptide comprises the amino acid sequence set forth in SEQ ID NO: 19. In some embodiments, the isolated scaffold polypeptide is consisting of the amino acid sequence set forth in SEQ ID NO: 19.

In some embodiments, an isolated scaffold polypeptide is provided, comprising a plurality of cohesin domains, wherein the plurality of cohesin domains comprises a cohesin derived from B. cellulosolvens and a cohesin derived from R. flavefaciens. In some embodiments, the plurality of cohesin domains is consisting of a cohesin derived from B. cellulosolvens and a cohesin derived from R. flavefaciens. In some embodiments, the isolated scaffold polypeptide comprises the amino acid sequence set forth in SEQ ID NO: 21. In some embodiments, the isolated scaffold polypeptide is consisting of the amino acid sequence set forth in SEQ ID NO: 21.

In some embodiments, an isolated scaffold polypeptide is provided, comprising a plurality of cohesin domains, wherein the plurality of cohesin domains comprises a cohesin derived from A. cellulolyticus and a cohesin derived from R. flavefaciens. In some embodiments, the plurality of cohesin domains is consisting of a cohesin derived from A. cellulolyticus and a cohesin derived from R. flavefaciens. In some embodiments, the isolated scaffold polypeptide comprises the amino acid sequence set forth in SEQ ID NO: 17. In some embodiments, the isolated scaffold polypeptide is consisting of the amino acid sequence set forth in SEQ ID NO: 17.

The scaffold polypeptides of the present invention may be utilized for the bio-conversion of cellulosic material. In some embodiments, a composition is provided, comprising a scaffold polypeptide of the present invention.

In some embodiments, a bio-engineered multi-enzyme complex is provided, comprising a scaffold polypeptide of the present invention. In some embodiments, there is provided a bio-engineered cellulosome comprising a scaffold polypeptide of the present invention.

There is further provided a system for bioconversion of cellulosic material comprising a scaffold polypeptide of the present invention.

According to another aspect, the present invention provides an isolated polynucleotide comprising a sequence encoding a polypeptide of the present invention.

In some particular embodiments, the isolated polynucleotide comprises a polynucleotide sequence selected from the group consisting of the sequences set forth in SEQ ID NOs: 6, 8, 18, 20, 22, 24 and 26. Each possibility represents a separate embodiment of the invention.

According to another aspect, the present invention provides a construct comprising a polynucleotide sequence of the present invention.

According to yet another aspect, the present invention provides a host cell comprising a polynucleotide sequence of the present invention. In some embodiments, the cell is selected from a prokaryotic and eukaryotic cell.

The variant polypeptides disclosed herein may be produced by recombinant or chemical synthetic methods. For example:

Recombinant Expression:

The variant polypeptides may be synthesized by expressing a polynucleotide molecule encoding the variant polypeptide in a host cell, for example, a microorganism cell transformed with the nucleic acid molecule.

DNA sequences encoding wild type polypeptides may be isolated from any cell producing them, using various methods well known in the art (see for example, Sambrook, et al., Molecular Cloning: A Laboratory Manual, Third Edition, Cold Spring Harbor, N.Y., (2001)). For example, a DNA encoding the wild-type polypeptide may be amplified from genomic DNA of an appropriate microorganism (for example, a bacterium) producing them by polymerase chain reaction (PCR) using specific primers, constructed on the basis of the nucleotide sequence of the known wild type sequence. Suitable techniques are well known in the art, described for example in U.S. Pat. Nos. 4,683,195; 4,683, 202; 4,800,159 and 4,965,188.

The genomic DNA may be extracted from the bacterial cell prior to the amplification using various methods known in the art, see for example, Marek P. M et al., "Cloning and expression in *Escherichia coli* of *Clostridium thermocellum* DNA encoding p-glucosidase activity", Enzyme and Microbial Technology Volume 9, Issue 8, Aug. 1987, Pages 474-478.

The isolated polynucleotide encoding the wild type polypeptide may be cloned into a vector, such as the pET28a plasmid.

Upon isolation and cloning of the polynucleotide encoding the wild type polypeptide, desired mutation(s) may be introduced by modification at one or more base pairs, using methods known in the art, such as for example, site-specific mutagenesis (see for example, Kunkel Proc. Natl. Acad. Sci. USA 1985, 82:488-492; Weiner et al., Gene 1994, 151:119-123; Ishii et al., Methods Enzymol. 1998, 293:53-71); cassette mutagenesis (see for example, Kegler-Ebo et al., Nucleic Acids Res. 1994 May 11; 22(9):1593-1599); recursive ensemble mutagenesis (see for example, Delagrave et al., Protein Engineering 1993, 6(3):327-331), and gene site saturation mutagenesis (see for example, U.S. Pat. Application No. 2009/0130718). Methods are also well known for introducing multiple mutations into a polynucleotide (see for example, Michaelian et al., Nucleic Acids Res. 1992, 20:376; Dwivedi et al., Anal. Biochem. 1994, 221:425-428; Bhat Methods Mol. Biol. 1996, 57:269-277; Meetei et al., Anal. Biochem. 1998, 264:288-291; Kim et al., Biotechniques 2000, 28:196-198; and International patent Application Publication Nos. WO 03/002761A1 and WO 99/25871). For example, introduction of two and/or three mutations can be performed using commercially available kits, such as the QuickChange site-directed mutagenesis kit (Stratagene).

An alternative method to producing a polynucleotide with a desired sequence is the use of a synthetic gene. A polynucleotide encoding a desired polypeptide may be prepared synthetically, for example using the phosphoroamidite method (see, Beaucage et al., Curr Protoc Nucleic Acid Chem. 2001 May; Chapter 3:Unit 3.3; Caruthers et al., Methods Enzymol. 1987, 154:287-313).

The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

In the case of a fusion protein, different polynucleotides may be ligated to form one polynucleotide. For example, different polynucleotides may be ligated into linearized pET21a.

The polynucleotide encoding the polypeptide of the invention may be incorporated into a wide variety of expression vectors, which may be transformed into in a wide variety of host cells. The host cell may be prokaryotic or eukaryotic.

Introduction of a polynucleotide into the host cell can be effected by well known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

Representative, non-limiting examples of appropriate hosts include bacterial cells, such as cells of *E. coli* and *Bacillus subtilis*.

The polypeptides may be expressed in any vector suitable for expression. The appropriate vector is determined according the selected host cell. Vectors for expressing proteins in *E. coli*, for example, include, but are not limited to, pET, pK233, pT7 and lambda pSKF. Other expression vector systems are based on betagalactosidase (pEX); maltose binding protein (pMAL); and glutathione S-transferase (pGST).

The proteins may be deigned to include a tag, for example, a His-Tag (six consecutive histidine residues), which can be isolated and purified by conventional methods.

Selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the polypeptide may be identified in cell extracts of the transformed cells. Transformed hosts expressing the polypeptide may be identified by analyzing the proteins expressed by the host, for example, using SDS-PAGE and comparing the gel to an SDS-PAGE gel obtained from the host which was transformed with the same vector but not containing a nucleic acid sequence encoding the desired polypeptide.

The desired polypeptides which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof. The polypeptides of the invention may be produced as fusion proteins, attached to an affinity purification tag, such as a His-tag, in order to facilitate their rapid purification.

The isolated polypeptide may be analyzed for its various properties, for example specific activity, using methods known in the art, some of them are described hereinbelow.

Conditions for carrying out the aforementioned procedures as well as other useful methods are readily determined by those of ordinary skill in the art (see for example, Current Protocols in Protein Science, 1995 John Wiley & Sons).

Synthetic Production:

The polypeptides of the present invention may also be produced by synthetic means using well known techniques, for example solid phase synthesis (see for example, Merrifield, R. B., J. Am. Chem. Soc., 85:2149-2154, 1963; Stewart, J. M. and Young, J. D., Solid Phase Peptide Synthesis, 2nd Ed., Pierce Chemical Co., Rockford, Ill., pp. 11-12). Synthetic peptides may be produced using commercially available laboratory peptide design and synthesis kits (see for example, Geysen et al, Proc. Natl. Acad. Sci., USA 1984, 81:3998). In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

As is readily apparent to those of skill in the art, the codon used in the polynucleotide for encoding a particular amino acid should be selected in accordance with the known and favored codon usage of the host cell which was selected for expressing the polynucleotide. A skilled person will be aware of the relationship between nucleic acid sequence and polypeptide sequence, in particular, the genetic code and the degeneracy of this code, and will be able to construct nucleic acids encoding the polypeptides of the present invention without difficulty. For example, a skilled person will be aware that for each amino acid substitution in a polypeptide sequence, there may be one or more codons which encode the substitute amino acid. Accordingly, it will be evident.

EXAMPLES

Example 1

Construction And Expression of Recombinant Proteins

Methods

Cloning of Wild-Type Enzymes:

Plasmids encoding wild-type enzymes pCel5A, pXyn11A, pXyn10B, pCel48A were cloned as described in Irwin et al. 1994 Appl. Environ. Microbiol. 60:763-770; Irwin et al. 2000 Eur. J. Biochem. 267:4988-97; Kim et al. 2004 Can. J. Microbiol. 50:835-843. The sequences of the resulting polynucleotides and corresponding polypeptides are set forth in the following SEQ ID NOs:

Cel5A cloned wild-type: DNA—SEQ ID NO: 64; amino acids—SEQ ID NO: 65.

Xyn11A cloned wild-type: DNA—SEQ ID NO: 66; amino acids—SEQ ID NO: 67.

Xyn10B cloned wild-type: DNA—SEQ ID NO: 68; amino acids—SEQ ID NO: 69.

Cel48A cloned wild-type: DNA—SEQ ID NO: 84; amino acids—SEQ ID NO: 85.

Cloning of Chimeric Enzymes:

The recombinant pf-5A was engineered as reported in Caspi et al. 2009 Appl. Environ. Microbiol. 75:7335-7342. The sequences of the resulting polynucleotide and corresponding polypeptide are set forth in SEQ ID NOs: 14 and 13, respectively. The b-48A chimera was cloned as described in Caspi et al. 2008 J. Biotechnol. 135:351-357. The sequences of the resulting polynucleotide and corresponding polypeptide are set forth in SEQ ID NOs: 16 and 15, respectively.

The 11A-a chimera, i.e., the catalytic module of Xyn11A attached directly to a dockerin from *Acetivibrio cellulolyticus* ATCC 33288, but lacking the family-2 xylan-binding CBM (XBM), was constructed from pXyn11A using primers:

SEQ 1N NO: 35:
5'CTGCCGCTAGCATGCACCATCACCAT-CACCACGCCGTGACCTCC AACGAGACC-3' (NheI site in boldface), and SEQ 1N NO: 36:
5'-TCCCAAGAGCTCCGTCGAACTAGTGC-CACCGCCACCGGGGGGG TTGCC-3' (SpeI and SacI sites in boldface) for cloning the catalytic module, and primers:
SEQ 1N NO: 37:
5'ATGTATACTAGTAAATTTATATATGGTGATGT-3' (SpeI site in boldface) and SEQ 1N NO: 38:
5'-TACCAAGAGCTCTTATTCTTCTTTCTCT-TCAACAG-3' (SacI site in boldface) for amplification of the *A. cellulolyticus* dockerin B.

The two modules were ligated (T4 DNA Ligase: Fermentas UAB Vilnius, Lithuania) into NheI-SacI (New England Biolabs Inc., Beverly, Mass.) linearized pET21a (Novagen Inc. Madison, Wis.) to form the p11A-a. The sequences of the resulting polynucleotide and corresponding polypeptide are set forth in SEQ ID NOs: 70 and 71, respectively.

The 11A-XBM-a chimera, i.e., the catalytic module of Xyn11A together with its adjacent XBM attached to a dockerin from *A. cellulolyticus* ATCC 33288, was constructed using primers: Primer (SEQ 1N NO: 39) 5'-TATCCGGAGCTCGTTGGCGCTGCAGGACACCG-3' (SacI site in boldface) was used to clone the full-length Xyn11A (together with the forward Xyn11A primer used above), and primers for cloning *A. cellulolyticus* dockerin B were designed:

SEQ 1N NO: 40:
5' TTATTCGAGCTCACAGCAACTACAACAC-CAACTACAACACCAAC TACAACACCAACGC-CTAAAT—3' (SacI site in boldface) and SEQ 1N NO: 41: 5' TTATTCGAGCTCACAGCAACTACAACAC-CAACTACAACACCAAC TACAACACCAACGC-CTAAAT-3' (XhoI site in boldface). The two PCR products were then ligated into NheI-XhoI linearized pET21a to form the p11A-XBM-a. The sequences of the resulting polynucleotide and corresponding polypeptide are set forth in SEQ ID NOs: 8 and 7, respectively.

The 10B-t chimera, i.e., the catalytic module of Xyn10B attached directly to a dockerin from *C. thermocellum*, was cloned as follows: the DNA encoding the *C. thermocellum* dockerin S (from Cel48S) was amplified from the genomic DNA (strain YS) using primers: SEQ 1N NO: 42:
5'-TTATTCACTAGTACATATAAAGTACCTG-GTACTCC-3' and SEQ IN NO: 43:
5'-TTATTCCTCGAGTTAGTTCTTGTACG-GCAATGTATC-3' (SpeI and XhoI sites in boldface). The Xyn10B catalytic module was cloned from the Xyn10B plasmid using primers: SEQ 1N NO: 44:
5'CATATTGCTAGCCATCACCATCACCAT-CACGGACCGGTCCACGA CCATCATCCC-3' and SEQ 1N NO: 45:
5' TTATTCCTCGAGTTATTAACTAGTA-CAGTGATCGTGCTTGGGGCC C-3' (NheI, SpeI and XhoI sites in boldface).

The two modules were then ligated into NheI-XhoI linearized pET21a to form the p10B-t. The sequences of the resulting polynucleotide and corresponding polypeptide are set forth in SEQ ID NOs: 6 and 5, respectively. All enzymes constructs were designed to contain a His-tag for subsequent purification.

Cloning of Chimeric Scaffoldins:

Scaffoldins were assembled from modules (cohesins, dockerins, CBM) cloned from different genomic DNAs. The following primers represent the homologous gene sequences only and were used with different restriction sites, either NcoI, KpnI, BamHI or Xhoi, depending on the desired construct. Cohesin F (cohesin 1 from *Ruminococcus flavefaciens* strain 17 scaffoldin B) was amplified using: SEQ 1N NO: 46:
5'-CGCCGGTGGTTTATCCGCTGTG-3' and SEQ 1N NO: 47:
5'-TTAATGGTGATGGTGATGGTGAACAAT-GATAGCGCCATCAGT-3'. The sequences of the resulting polynucleotide and corresponding polypeptide are set forth in SEQ ID NOs: 72 and 73, respectively.

Cohesin A (cohesin 3 from *A. cellulolyticus* scaffoldin C) was cloned from genomic DNA using SEQ 1N NO: 48: 5'-ATTTACAGGTTGACATTGGAAGT-3' and SEQ 1N NO: 49: 5'-GATGCAATTACCTCAATTTTTCC-3'. The sequences of the resulting polynucleotide and corresponding polypeptide are set forth in SEQ ID NOs: 74 and 75, respectively.

Cohesin B (cohesin 3 from *Bacteroides cellulosolvens* scaffoldin B) was amplified using SEQ 1N NO: 86: 5' CCATGGCGGGGAAAAGTTCACCAG 3' (five random bases were added before the restriction site in each primer) and SEQ 1N NO: 87: 5' GGTACCTTAGTTACAGTAAT-GCTTCC 3' primers (NcoI and KpnI sites in boldface type). The sequences of the resulting polynucleotide and corresponding polypeptide are set forth in SEQ ID NOs: 76 and 77, respectively.

CBM-T (CBM3a and cohesin 3 from the cellulosomal scaffoldin subunit *Clostridium thermocellum* YS) was cloned from *C. thermocellum* YS genomic DNA using: SEQ 1N NO: 50: 5'-GACAAACACACCGACAAACACA-3' and SEQ 1N NO: 51: 5'-CTATATCTCCAACATTTACTCCAC-3'. The sequences of the resulting polynucleotide and corresponding polypeptide are set forth in SEQ ID NOs: 80 and 81, respectively. The sequence of the DNA encoding Cohesin T (cohesin 3 from *Clostridium thermocellum* CipA scaffoldin) and the resulting polypeptide are set forth in SEQ ID NOs: 78 and 79, respectively.

The different modules were assembled in the linearized pET28a plasmid to form the chimeric scaffoldins.

pScaf.T, pScaf.F and pScaf-A were cloned as described in Haimovitz et al. 2008 Proteomics 8:968-979. The amino acid sequences of the resulting polypeptides and the DNA encoding them are set forth in the following SEQ ID NOs:

Scaf-T DNA—SEQ ID NO: 52; Scaf-T amino acids—SEQ ID NO: 53.

Scaf-B DNA—SEQ ID NO: 54; Scaf-B amino acids—SEQ ID NO: 55.

Scaf-F DNA—SEQ ID NO: 56; Scaf-F amino acids—SEQ ID NO: 57.

Scaf-A DNA—SEQ ID NO: 58; Scaf-A amino acids—SEQ ID NO: 59.

To form the dockerin-containing pf-XBM, the XBM was amplified from the Xyn11A plasmid using the following primers: SEQ 1N NO: 60:

5'-AAATAAGGTACCTACCAGCGGCGGTG-GAAACCCC-3' (KpnI site in boldface) and SEQ 1N NO: 61:

5'-AAATTACTCGAGCTAGTTGGCGCTGCAGGACA-3' (XhoI site in boldface), and ligated to linearized pET28a together with the *R. flavefasciens* ScaB dockerin, cloned from genomic DNA using: SEQ 1N NO: 62:

5'TGATCCATGGCACACCATCACCATCAC-CATGCACCATCACCCGG CACAAAGC-3' (BamHI site in boldface) and SEQ 1N NO: 63:

5'-ATGCTTGGTACCGCTTGAGGAAGTGT-GATGAGTTCAA-3' (KpnI site in boldface). The sequences of the resulting polynucleotide and corresponding polypeptide are set forth in SEQ ID NOs: 82 and 83, respectively. Other recombinant scaffoldins were cloned as described in Irwin et al. 1994 Appl. Environ. Microbiol. 60:763-770; Irwin et al. 2000 Eur. J. Biochem. 267:4988-97; Haimovitz et al. 2008 Proteomics 8:968-979. The sequences of the resulting polynucleotides and corresponding polypeptides are set forth in SEQ ID NOs:

Scaf-AF: DNA—SEQ ID NO: 18; amino acids—SEQ ID NO: 17.

Scaf-BF: DNA—SEQ ID NO: 22; amino acids—SEQ ID NO: 21.

Scaf AT: DNA—SEQ ID NO: 20; amino acids—SEQ ID NO: 19.

Scaf-ATF: DNA—SEQ ID NO: 24; amino acids—SEQ ID NO: 23.

Scaf-BTFA: DNA—SEQ ID NO: 26; amino acids—SEQ ID NO: 25.

PCR reactions were performed using ABgene Reddymix ×2 (Advanced Biotechnologies Ltd., Epsom, UK), DNA samples were purified using a HiYield™ Gel/PCR Fragments Extraction Kit (Real Biotech Corporation, RBC, Banqiao City, Taiwan).

Protein Expression and Purification:

Cel5A, Xyn11A, Xyn10B were prepared as described in Irwin et al. 1994 Appl. Environ. Microbiol. 60:763-770; Irwin et al. 2000 Eur. J. Biochem. 267:4988-97; Kim et al. 2004 Can. J. Microbiol. 50:835-843. The f-5A chimera was expressed as reported in Caspi et al. 2009 Appl. Environ. Microbiol. 75:7335-7342.

The 11A-a, 11A-XBM-a, 10B-t and f-XBM plasmids were expressed in *E. coli* BL21 (λDE3) pLysS cells and purified on a Ni column, as reported in Caspi et al. 2006 Biocat. Biotransform. 24:3-12. Cel48A and the b-48A chimera were expressed as reported in Caspi et al. 2008 J. Biotechnol. 135:351-357. Scaffoldins were expressed and purified on phosphoric acid swollen cellulose 7.5 mg m-1-1 pH 7 (PASC) according to the previously described methodology Haimovitz et al. 2008 Proteomics 8:968-979. Protein expression and purification was carried out by transforming BL21 (XDE3) pLysS cells with the designated plasmids and growing them on Luria-Bertani medium at 37° C. to an $A_{600}$~1. Isopropyl thio-β-D-galactoside (IPTG) was added to a final concentration of 0.1 mM. Following induction, cells were incubated for 3 h at 37° C., centrifuged, sonicated, and the supernatant fluids were incubated with amorphous cellulose for 1-2 h at 4° C. to allow binding of the CBM-Coh. The amorphous cellulose was washed three times with TBS, pH 7.4, containing 1M NaCl and three times with TBS. The protein was eluted with 1% v/v triethylamine, and neutralized with MES buffer.

Purity of the recombinant proteins was tested by SDS-PAGE on 12% acrylamide gels. The concentration of each purified protein was estimated by absorbance (280 nm) based on the known amino acid composition of the protein using the Protparam tool. Proteins were stored in 50% (v/v) glycerol at −20° C.

Results

The recombinant proteins are shown schematically in FIG. 1. Four different *T. fusca* enzymes were used: two xylanases, Xyn11A and Xyn10B, and two cellulases, the family-5 endoglucanase, Cel5A and the family-48 exoglucanase Cel48A. Cel5A and Cel48A are typical free (non-cellulosomal) enzymes that both contain a family-2 cellulose-binding CBM. Xyn11A contains a CBM from the same family, which shows binding specificity for both cellulose and xylan. Xyn10B lacks a CBM.

Dockerins from different specificities were used to replace the CBM or XBM of the native enzymes, generating f-5A, b-48A and 11A-a, or added in the C-terminal of the xylanases generating 11A-XBM-a and 10B-t.f-5A is a recombinant cellulose-hydrolyzing enzyme consisting of two fused modules: a catalytic module of the family-5 endoglucanase Cel5A from *T. fusca*, and a dockerin from *Ruminococcus flavefaciens* (Ding et al. 2001 J. Bacteriol. 183:1945-1953). b-48 was designed to contain the catalytic module of the *T. fusca* exoglucanase Cel48A ligated with a dockerin from the *Bacteroides cellulosolvens* ScaA scaffoldin.

Two recombinant forms of Xyn11A were designed: one, 11A-XBM-a, in which dockerin B from *Acetivibrio cellulolyticus* was appended at the C-terminus of the original Xyn11A thus retaining the original catalytic module and xylan-binding CBM (XBM), and a second, 11A-a, in which XBM was replaced by the same *A. cellulolyticus* dockerin. The resultant fusion protein is identical to 11A-XBM-a, but now lacks the XBM. 11A-a is employed as a crucial control, in order to assay the importance of the XBM module in the enzymatic activity of the enzyme alone or within a complex. XBM alone was also examined for its contribution to activity; therefore the dockerin of scaffoldin A from *Ruminococcus flavefaciens* (Ding et al. 2001 J. Bacteriol. 183:1945-1953) was fused to the XBM module at the N-terminus of the protein. In order to integrate Xyn10B into an enzymatic complex, the dockerin from exoglucanase Cel48S of *Clostridium thermocellum* (Wang et al. 1993 J. Bacteriol. 175:1293-1302)

was fused at its C-terminus resulting in 10B-t.ScafAF has two cohesins of divergent specificity, allowing the possibility of binding two different dockerin-containing proteins selectively. The specific modules that comprise the construct are as follows: cohesin 3 from *A. cellulolyticus* scaffoldin C (designated A) (Xu et al. 2003 J. Bacteriol. 185:4548-4557), CBM3a from *C. thermocellum*, which binds strongly to cellulose (Morag et al. 1995 Appl. Environ. Microbiol. 61:1980-1986), and cohesin 1 from *R. flavefaciens* scaffoldin B (designated F) (Ding et al. 2001J. Bacteriol. 183:1945-1953). Scaf.AF allows the specific incorporation of the previously described enzymes (either 11A-XBM-a or 11A-a and f-5A), and will direct the complex to the substrate via the CBM.

Scaf.AT also has 2 different cohesins and a cellulose-binding CBM. *A. cellulolyticus* cohesin 3 (A, as specified above) will interact specifically with enzymes carrying the matching dockerin, i.e., 11A-XBM-a or 11A-a. At the C-terminus, T-cohesin 3 from the CipA *C. thermocellum* scaffoldin (Yaron et al. 1995 FEBS Lett. 360:121-124)—will bind with the dockerin S-containing enzyme, 10B-t.

Scaf.ATF, includes all three above-described cohesin types together with the cellulose-binding CBM. This 3-cohesin scaffoldin enables the integration of the two xylanases, 10B-t and 11A-XBM-a (or 11A-a), and endoglucanase f-5A. Scaf-BF has two cohesins of divergent specificity, allowing the possibility of binding two different dockerin-containing proteins selectively. The specific modules that comprise the construct are as follows: cohesin from *B. cellulosolvens* ScaB, CBM3a from *C. thermocellum*, which binds strongly to cellulose (described above), and cohesin 1 from *R. flavefaciens* scaffoldin B (designated F, described above). Scaf.BF allows the specific incorporation of the previously described enzymes (b-48A and f-5A), and will direct the complex to the substrate via the CBM. Scaf.BTFA includes all four above-described cohesin types together with the cellulose-binding CBM. This 4-cohesin scaffoldin enables the integration of the two xylanases, 10B-t and 11A-XBM-a, and the two cellulases f-5A and b-48A. All purified recombinant proteins showed a single major band on SDS-PAGE and in each case their mobility was consistent with their molecular mass.

Example 2

Interaction Between Scaffoldin and Enzymes

Methods:
Affinity-Based ELISA:
The matching fusion-protein procedure of Barak et al. 2005J. Mol. Recogit. 18:491-501; and Caspi et al. 2006 Biocat. Biotransform. 24:3-12. was followed to determine cohesin-dockerin specificity.

For example, for the analysis of dockerin-containing xylanases:

Analysis of Divergent Dockerins Using Immobilized Cohesins:

MaxiSorp ELISA plates (Nunc A/S, Roskilde, Denmark) were coated overnight at 4° C. with predetermined concentrations (designated below) of the desired CBM-Coh (100 µl/well) in 0.1M sodium carbonate (pH 9). The following steps were performed at room temperature with all reagents at a volume of 100 µl/well. The coating solution was discarded and blocking buffer (TBS, 10 mM $CaCl_2$, 0.05% Tween 20, 2% BSA) was added (1 h incubation). The blocking buffer was discarded, and incremental concentrations of the desired XynDoc constructs, diluted in blocking buffer, were added. After a 1 h incubation period, the plates were washed three times with wash buffer (blocking buffer without BSA), and the primary antibody preparation (rabbit anti-xylanase T-6 antibody, diluted 1:10,000 in blocking buffer) was added. Following another 1 h incubation period, the plates were washed three times with wash buffer and the secondary antibody preparation (HRP-labeled anti-rabbit antibody diluted 1:10,000 in blocking buffer) was added. After another 1 h incubation, the plates were again washed (four times) with wash buffer and 100 µl/well TMB+Substrate-Chromogen were added. Color formation was terminated upon addition of 1M $H_2SO_4$ (50 µl/well), and the absorbance was measured at 450 nm using a tunable microplate reader. Absorbance was plotted as a function of XynDoc concentration, usually resulting in a sigmoidal (dose-response) curve. For presentation of results in bar graph form, two alternative and complementary methods were used: (i) the $pEC_{50}$ was determined for the binding curve of the test XynDoc constructs and compared with that of the XynDoc standard; and (ii) the 'reference concentration' of a XynDoc standard that generates a maximum response was employed for comparison of the level of response produced by other test XynDoc constructs at that concentration. In the latter case, the data can be normalized as a percentage (relative binding) of maximum response by the reference XynDoc. The two methods produced very similar results.

Analysis of Divergent Cohesins Using Immobilized Dockerins:

The assay for divergent cohesins was essentially the converse of that described above for the divergent dockerins: instead of immobilizing a cohesin construct, a suitable dockerin construct was substituted. The following modifications were then introduced: coating was performed with 20 nM of the desired XynDoc construct, the desired CBM-Coh(s) was diluted to concentrations of 10 µM to 10 nM, and rabbit anti-CBM antibody (diluted 1:10,000) was used as the primary antibody preparation. Subsequent steps were performed as described in the previous section.

Non-Denaturing PAGE:
A differential mobility assay on non-denaturing gels was used to check the full interaction between scaffoldin and enzymes. In a 30 µl reaction (in which 15 µl of Tris Buffer Saline pH 7.4 (TBS) buffer, supplemented with 10 mM $CaCl_2$ and 0.05% Tween 20), 4-8 µg of each protein were added in an equimolar manner. The 1.5 ml tubes were incubated 1.5 h at 37° C. Sample buffer (7.5 in the absence of SDS) was added to 15 µl of the reaction mixture, and the samples were loaded onto non-denaturing gels (4.3%-stacking/9%-separating phase). A parallel SDS-PAGE gel (10%) was performed on the remaining 15 µl sample.

Figure 2A:
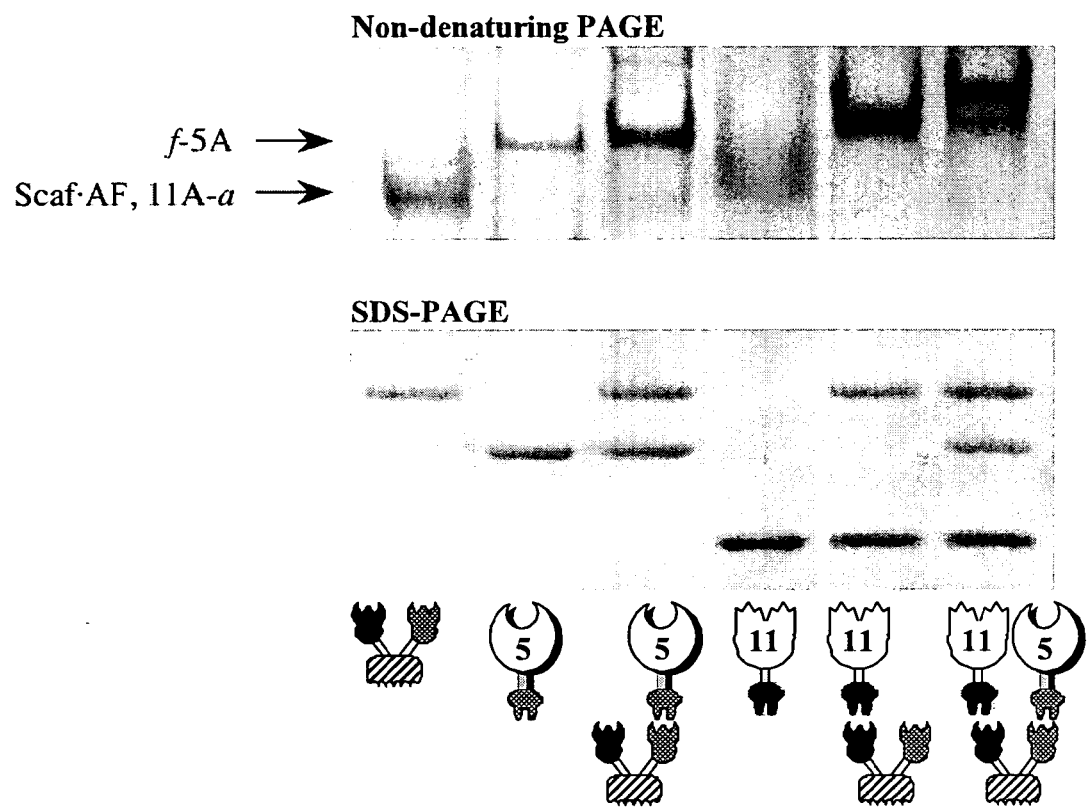
FIG. 2. Electrophoretic mobility of components and assembled complexes on non-denaturing and denaturing gels. A) Equimolar concentrations of the chimeric enzymes (f-5A and 11A-a) and their matching scaffoldin (Scaf.AF) were combined. The single fusion proteins and the mixtures were subjected to non-denaturing PAGE (top panel) and SDS-PAGE (bottom panel). Analysis of the matching components by native PAGE clearly shows their complete or near-complete interaction. B) Equimolar concentrations of the chimeric enzymes (f-5A, b-48A, 11A-XBM-a and 10B-t) and their matching scaffoldin (Scaf.BTAF) were combined. The single fusion proteins and the mixtures were subjected to non-denaturing PAGE (top panel) and SDS-PAGE (bottom panel). Analysis of the matching components by native PAGE clearly shows their complete interaction.
Figure 2B:
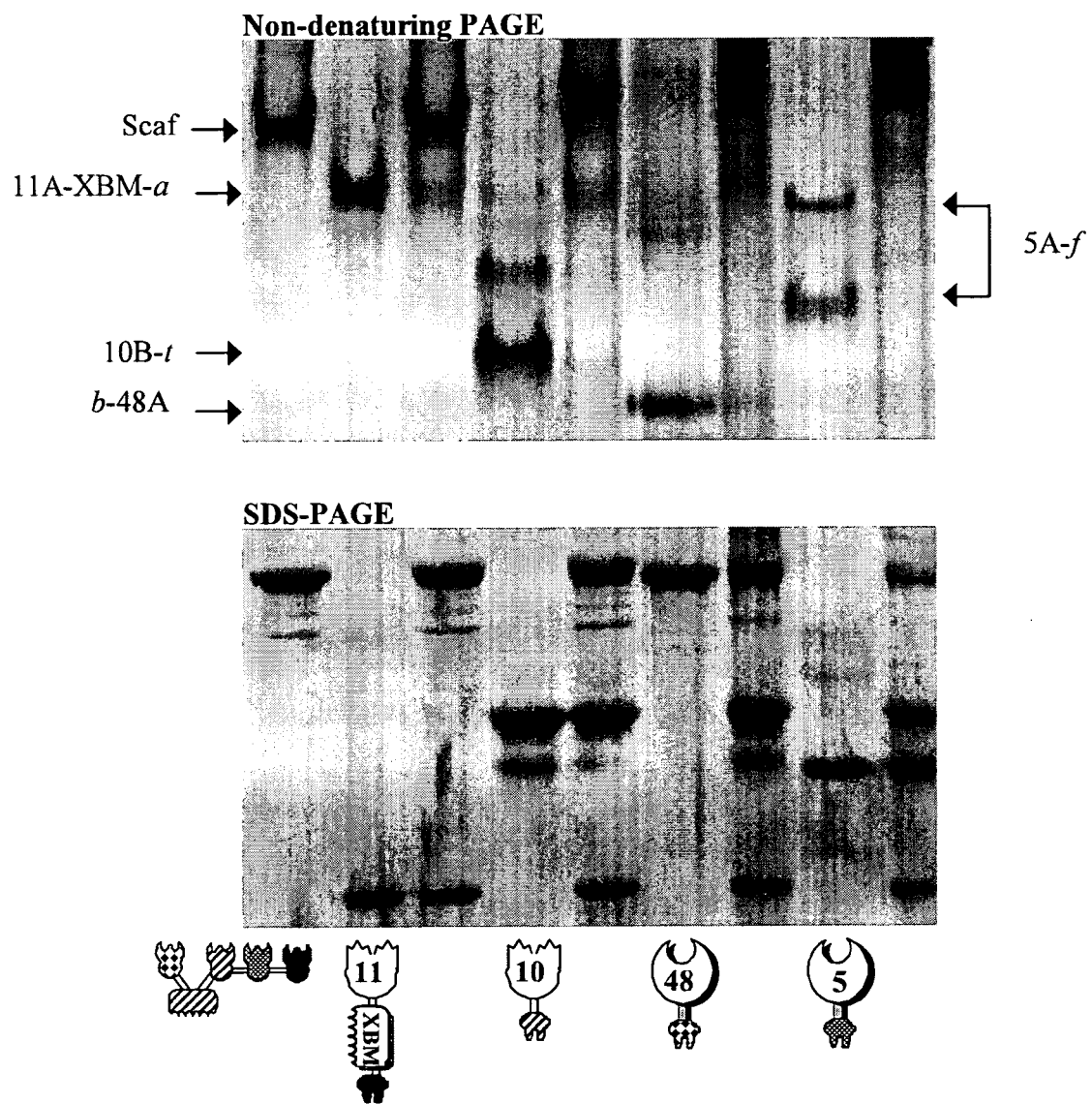

Results
The specificity of the cohesins for the chimeric dockerin-bearing enzymes was examined semi-quantitatively by a sensitive enzyme-linked affinity assay in microtiter plates. All of the cohesins in each scaffoldin specifically bound their respective dockerin and did not bind (or bound very poorly) other non-matching dockerin-bearing molecules. The scaffoldin-borne cohesins bound their matching dockerins just as efficiently as the individual single-cohesin scaffoldins, indicating that the binding capabilities of the scaffoldins were reliable and selective. All specific cohesin-dockerin interactions, for each scaffoldin, were of similar intensity, thus indicating that similar amounts of protein were bound in each well, suggesting a molar equivalent of 1:1 scaffoldin (cohesin): dockerin ratio. For each chimeric designer cellulosome, complex formation was tested by non-denaturing PAGE. Denaturing PAGE was used as a control for sample content verification. Stoichiometric mixtures of the enzymes and the scaffoldin resulted in a single band with altered mobility (band strengthened and shifted) thus indicating that complete or near-complete complexation was achieved in all cases (an example is given in FIG. 2).

Example 3

Binding to Insoluble Polysaccharides

Method

Insoluble xylan was prepared by boiling oat-spelt xylan (Sigma Chem. Co., St. Louis, Mo.) for 30 min in distilled water and recovering the residue by centrifugation; this was followed by 3 washes with distilled water, and its dry weight was determined. Microcrystalline cellulose (Avicel) was purchased from FMC Biopolymer (Philadelphia, Pa., USA). The binding of each protein to insoluble polysaccharides (insoluble xylan from oat spelt and microcrystalline cellulose) was determined qualitatively using SDS-PAGE. Pure protein (10 μg for xylan binding assays and 5 μg for cellulose binding experiments in 50 mM citrate buffer pH 6.0, 12 mM $CaCl_2$, 2 mM EDTA) was mixed with 0.5 mg of insoluble xylan or 10 mg of microcrystalline cellulose, in a final volume of 100 μl. Tubes were incubated on ice for 1 h with gentle mixing before being centrifuged at 14000 rpm for 1 min, and the supernatant fluids (containing unbound protein) were carefully removed. The polysaccharide pellet was then washed once by resuspending in 100 μl of the same buffer and centrifugation before resuspending in 60 μl of SDS-containing buffer and boiled for 10 min to dissociate any bound protein. BSA was used as negative control to ensure specificity of binding. Bound and unbound fractions were analyzed by SDS-PAGE using a 12% polyacrylamide gel.

Results

The majority of the family-10B enzyme was able to bind to insoluble xylan this was due to the inherent binding capacity of the catalytic module only, since the protein does not include any XBM. The same result was obtained for 11A-a in which the XBM module was replaced by the dockerin module—the enzyme was found both in the bound and unbound fractions. The Xyn11A, 11A-XBM-a, and f-XBM proteins were located in the bound fractions, suggesting that the dockerin module in 11A-XBM-a did not disturb the binding function of the XBM and that the XBM alone is able to bind xylan. Upon mixing the proteins with microcrystalline cellulose, Xyn11A and 11A-XBM-a were found exclusively in the bound fractions; thus the cellulose-binding ability of the protein is maintained in 11A-XBM-a, and has not been affected by the dockerin module. f-XBM was found in approximately equal portions in both fractions, suggesting that the binding function to Avicel reflects the combined action of the entire protein (catalytic module and XBM), and the lack of the catalytic module results in a weakened ability to bind the substrate. Indeed, 11A-a, which lacks the XBM, was also found in both fractions (the major part was found in the bound fraction) reinforcing the hypothesis that the protein needs its catalytic module together with its XBM to achieve full substrate-binding capacity. The Xyn10B and 10B-t enzymes bound cellulose very weakly, indicating a low but measurable cellulose-binding activity associated with the family 10 catalytic module. As expected, more than ~95% of the BSA negative control was found in the unbound fraction. These results are in perfect accord with previous publications (Irwin et al. 1994 Appl. Environ. Microbiol. 60:763-770; Kim et al. 2004 Can. J. Microbiol. 50:835-843), in which the binding capacity of the wild-type Xyn11A and Xyn10B enzymes was investigated. Xyn11A was found to bind strongly to insoluble xylan and cellulose, and a weak ability to bind insoluble xylan binding was demonstrated for Xyn10B. In previous binding experiments to microcrystalline cellulose, Cel5A exhibited an ability to bind to cellulose whereas f-5A failed to bind cellulose due to the lack of CBM2 (Caspi et al. 2009 Appl. Environ. Microbiol. 75:7335-7342).

Example 4

Enzymatic Activity of Free Xylanases on Xylans

Method

Xylanase activity was determined quantitatively by measuring the reducing sugars released from xylan by the dinitrosalicyclic acid (DNS) method (Ghose et al. 1987 Pure. Appl. Chem. 59:257-268; Miller et al. 1959 Anal. Biochem. 31:426-428). A typical assay mixture consisted of 100 μl buffer (50 mM citrate buffer pH 6.0, 12 mM $CaCl_2$, 2 mM EDTA) with enzyme (0-10 nM). The reaction was commenced by adding 100 μl of 2% xylan (birchwood, beechwood or oat spelt from Sigma Chem. Co, St. Louis Mo.), suspended in 50 mM citrate buffer, pH 6.0, and the reaction was continued for 20 min at 50° C. The reaction was stopped by transferring the tubes to an ice-water bath, 100 μl of the supernatant were then added to 150 μl DNS reagent, and the tubes were boiled for 10 min, after which absorbance was measured at 540 nm. Dockerin-containing enzymes were subjected to 1.5-h incubation (37° C., in the absence of substrate) in the presence of equimolar concentrations of scaffoldin, prior to assay.

Results

All recombinant xylanases were tested for xylan degradation on a variety of xylan substrates. Three different substrates were used to test the degradation activity of the transformed xylanases: birchwood xylan, beechwood xylan and oat spelt xylan. The characteristics (composition and properties) of xylans from different origins were previously investigated by Hespell et al. 1995 Appl. Environ. Microbiol. 61:3042-3050. Birchwood xylan is more than 90% soluble in water and is composed of a high percentage of neutral sugars (87.7% mainly xylose residues, small amounts of glucose and traces of arabinose and galactose can be found) and 10.2% of hexuronic acids. The ratio of sugars in beechwood xylan is comparable to birchwood xylan, but they differ in their relative content of hexuronic acids (less than 3% found in beechwood xylan) and in their water solubility: beechwood xylan is approximately 95% insoluble in water. Oat spelt xylan is a mixture of a high percentage of xylose (84%) and some arabinose, glucose and galactose, its water solubility varies greatly depending on temperature and extent of centrifugation. The family-11A enzymes were more effective in the degradation of xylans than the family-10B enzymes. On each substrate the enzymatic activities of the wild-type enzyme and its derivatives were very close, suggesting that the addition of the dockerin module had very little effect on the structural conformation of the enzymes.

Table 1 below summarizes the specific activity values obtained for all the tested chimeras and wild-type constructs. Oat spelt xylan was the most efficiently degraded substrate for all the enzymes. For the 11A enzymes, 11A-a had similar specific activity on all three substrates, which was lower than those of the XBM-containing enzymes, i.e., Xyn11A and 11A-XBM-a (which had comparable specific activities). Deletion of the XBM module may have a negative impact on its activity on these substrates, suggesting that the XBM-targeting role is important even for easily degraded substrates like purified xylan. Interestingly, the specific activities observed for 10B-t were higher than those of wild-type Xyn10B on all substrates; so the addition of the dockerin module may have allowed better access of the catalytic module towards its substrate. Xyn10B exhibited the lowest activity on beechwood xylan compared to the other substrates. The solubility properties of the xylan may thus play a role in degradation by this enzyme: the more insoluble the substrate, the more difficult for the enzyme to degrade it. Enzymatic activities of Cel5A and f-5A on a variety of cellulosic substrates were reported earlier (Caspi et al. 2009 Appl. Environ. Microbiol. 75:7335-7342).

TABLE 1

Specific activities* of recombinant enzymes on various xylans

| Substrate | Xyn10B | 10B-t | Xyn11A | 11A-a | 11A-XBM-a |
|---|---|---|---|---|---|
| Birchwood xylan | 89.9 | 136 | 430 | 337 | 425 |
| Oat spelt xylan | 125 | 152 | 449 | 342 | 433 |
| Beechwood xylan | 40.3 | 97.4 | 438 | 345 | 445 |

*Katal/mol enzyme

Example 5

Enzymatic Activity on Hatched Wheat Straw

Method

Hatched wheat straw (0.2-0.8 mm) provided by Valagro (Poitiers, France) was treated as described previously (Fierobe et al. 2005 J. Biol. Chem. 280:16325-16334; Tabka et al. 2006 Enzyme Microb. Technol. 39:897-902): the crude substrate was incubated in distilled water under mild stirring for 3 h at room temperature, vacuum filtered on 2.7-μm glass filter, resuspended in water, and incubated for 16 h under mild stirring at 4° C. The suspension was filtered and washed three times with water, and a sample was dried at 100° C. overnight for estimation of dry weight.

A typical assay mixture consisted of 100 μl of buffer (50 mM citrate buffer pH 6.0, 12 mM $CaCl_2$, 2 mM EDTA) and hatched wheat straw 3.5 g/l. The concentration of the enzymes added was 0.2 μM (0.3 μM for xylanases only). For assays described in "A" and "B" below the reactions were incubated for 17 hours at 50° C. For assays described in "C" and "D" below the reaction mixtures were incubated at 50° C. After 1, 4, 7 and 20 hours of substrate degradation, the reactions were stopped by transferring the tubes to an ice-water bath, then after a centrifugation step (5 min at 14000 rpm), 100 μl of the supernatant were added to 150 μl DNS reagent and the tubes were boiled for 10 min, finally absorbance was measured at 540 nm (Miller et al, 1959). Dockerin-containing enzymes were subjected to 1.5-h incubation (37° C., in the absence of substrate) in the presence of equimolar concentrations of scaffoldin, prior to assay for binding interaction.

All assays were performed in triplicate.

Results

A. Enzymatic Assays of Free Enzymes on Hatched Wheat Straw

Figure 3:
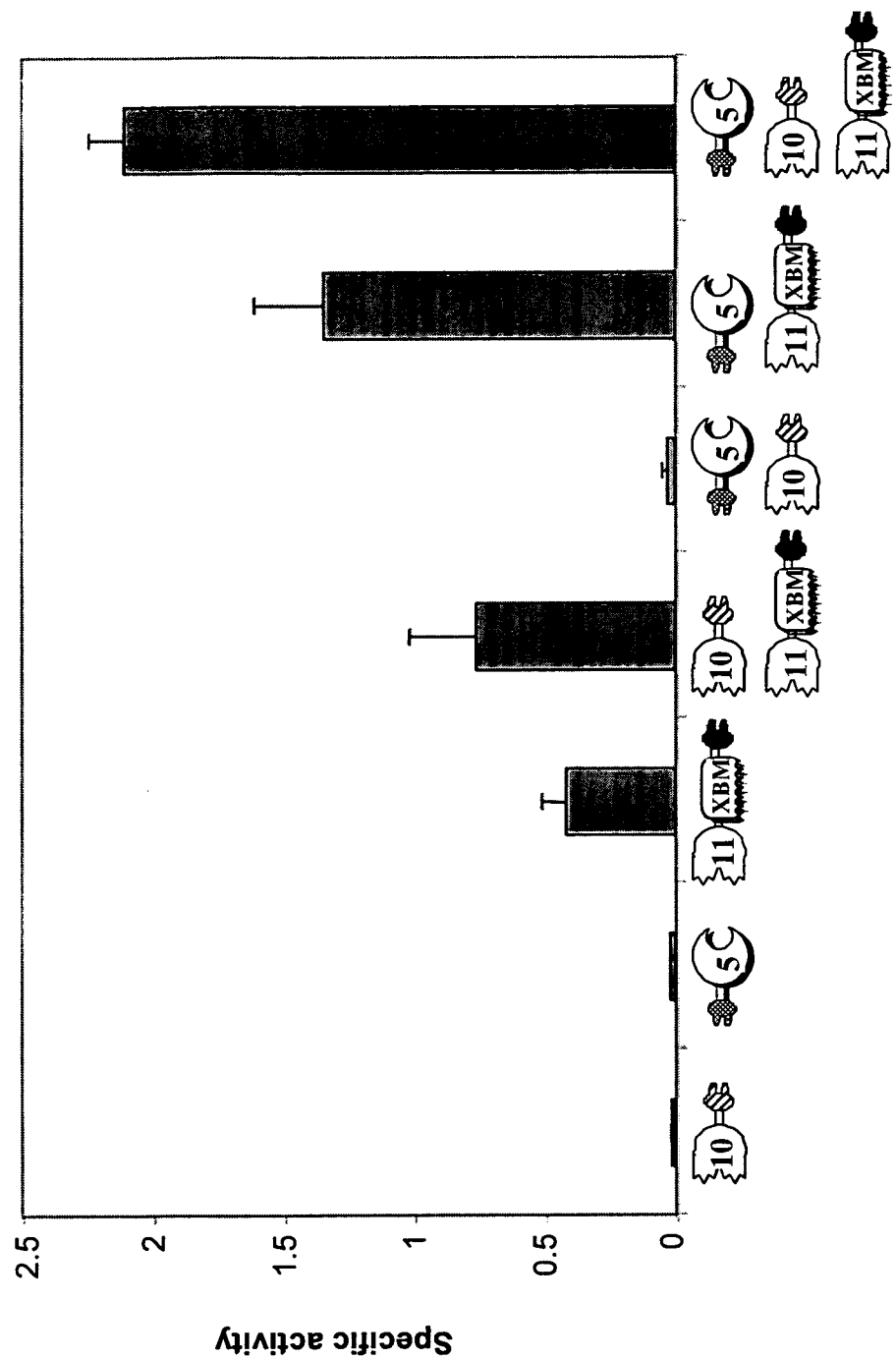
FIG. 3. Specific activities of single dockerin-containing enzymes or combinations thereof. The composition of the complexes and free enzymes systems is indicated at the bottom of the graph. Each enzyme or enzyme combination was assayed at 0.3 µM with 3.5 g/l hatched wheat straw in a 200 µl reaction. Specific activity is defined as µM reducing sugar per min per µM enzyme. Triplicate samples of each reaction mixture were employed, and standard deviations for straw hydrolysis are indicated.

Each of the dockerin-containing enzymes and their combinations were tested for activity on hatched wheat straw (FIG. 3). 10B-t and f-5A exhibited very weak activity on straw, whereas 11A-XBM-a showed higher levels of hydrolysis. Synergism was demonstrated for the following combinations: 10B-t+11A-XBM-a, 11A-XBM-a+f-5A and the three enzymes together (f-5A+11A-XBM-a+10B-t), with respective activity enhancements of 1.8, 3.1 and 4.6 fold (compared to the theoretical total of the individual activities). Notably, synergism was observed within all the combinations containing 11A-XBM-a, suggesting that 11A-XBM-a attacks the straw substrate in such a manner that it allows the other enzymes access to their specific sites on the complex substrate. Xyn10B proved to be less active than Xyn11A during initial degradation of the different xylans, but the enzyme seemed to contribute to the complete conversion of xylan into xylobiose, as reported earlier (Kim et al., 2004). The same synergistic action may also occur in the degradation of a more complex substrate, like straw, which could involve divergent cleaving mechanisms and would explain why Xyn10B (or its chimeric derivative, 10B-t) cannot achieve substantial levels of degradation by itself, but contributes to the reaction when combined with 11A-XBM-a. This hypothesis could explain the synergistic activities observed for the combinations of enzymes, i.e., the two-enzyme system 11A-XBM-a+f-5A and the three-enzyme mixture f-5A+11A-XBM-a+10B-t. Interestingly, the combination of 10B-t+f-5A reaction did not show improved activity. Xyn10B and Cel5A (or their chimeric derivatives) may have difficulty in accessing their target substrate within the complex matrix of the straw composite, and require the association with an additional enzyme such as Xyn11A to degrade straw efficiently. The same experiment was carried out with the wild-types enzymes and equivalent results were obtained (data not shown), thus indicating that the presence of dockerins in the enzymes do not substantially affect the overall action of these enzymes on the crude substrate. Additional trials were carried out in subsequent experiments only with the enzyme combinations that showed clear synergistic activity. Several concentrations of the enzyme combinations were tested in order to ensure that 0.3 mM enzyme provide linear reaction for the given time points (data not shown). Previous results were confirmed: as the three-enzyme system Cel5A+Xyn11A+Xyn10B (or f-5A+11A-XBM-a+10B-t) appeared to be more effective than the enzyme pair, Cel5A+Xyn11A (or f-5A+11A-XBM-a), which was more effective than Xyn11A+Xyn10B (11A-XBM-a+10B-t). The same trend was evident for the entire range of experimental data.

Kinetics studies also proved that the reaction is still in the linear part of the curve after 16-18 hours of enzymatic action (data not shown).

Figure 4:
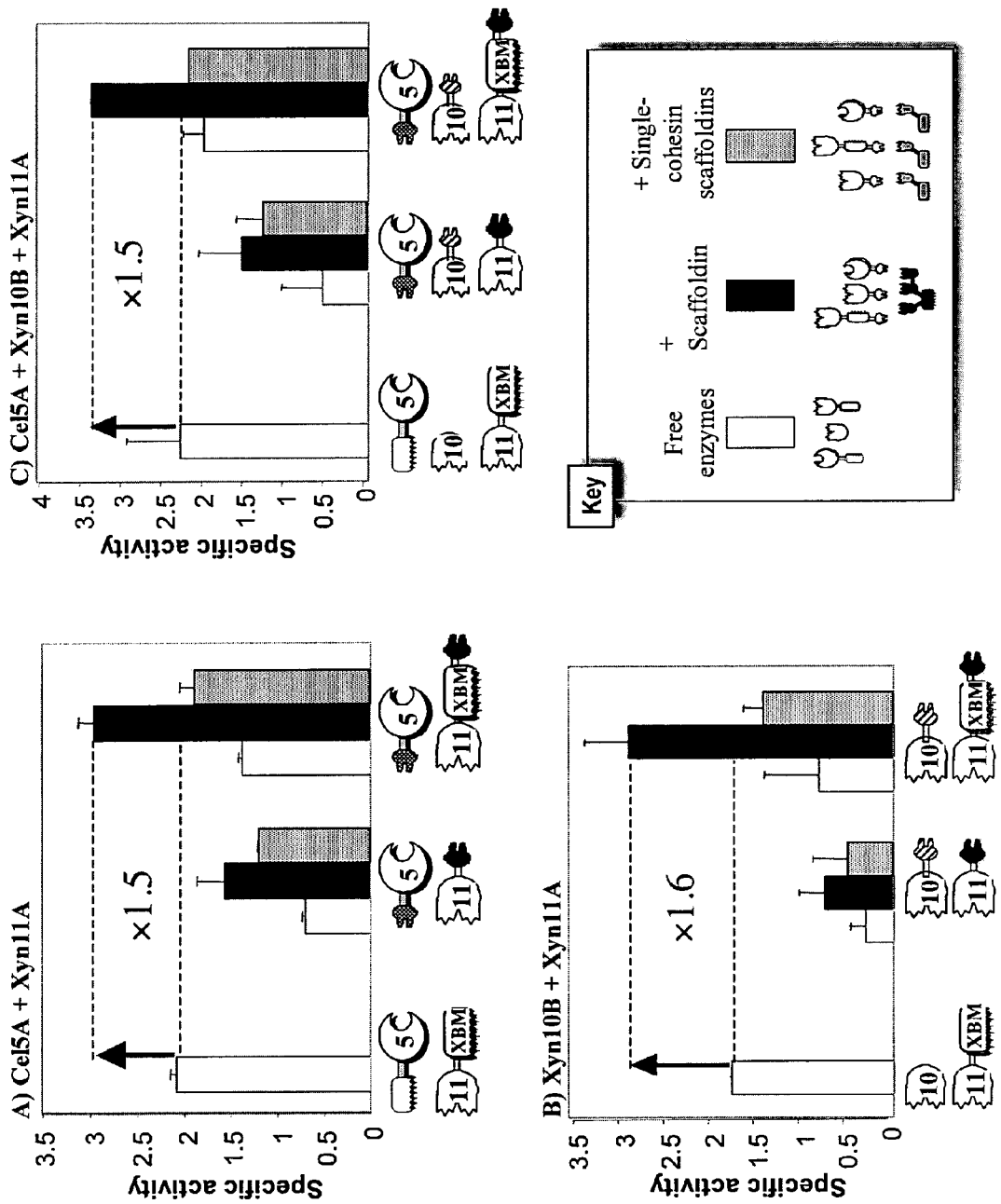
FIG. 4. Comparative degradation of straw by the various complexes and free enzyme systems. The composition of the complexes and free enzymes systems is indicated in symbolic form at the bottom of the graph. White encoded bars represent the free enzyme system; black bars the enzyme-scaffoldin complexes and the dotted bars the enzymes attached to their corresponding individual single-cohesin scaffoldins. Specific activity is defined as µM reducing sugar per min per enzyme. Each reaction was performed in triplicate, and standard deviations for straw hydrolysis are indicated.

B. Enzymatic assays of tri-functional designer cellulosomes on hatched Wheat Straw The combination of cellulase Cel5A with xylanase Xyn11A was examined in three different modes: (i) the free enzyme mixture, (ii) the designer cellulosome and (iii) the individually targeted enzyme system. Designer cellulosomes were constructed by mixing the desired dockerin-containing enzymes with the chimeric scaffoldins bearing the appropriate matching cohesins. The targeting effect was assessed by attaching the individual enzymes to a single-cohesin (CBM-containing) scaffoldin construct. The specific activities of the enzyme mixtures in each of the three modes were compared, and the results are shown in FIG. 4. As free enzymes (cellulase Cel5A and xylanase Xyn11A), the wild-type enzymes appeared to have a better specific activity than the dockerin-bearing enzymes—both f-5A+11A-a and f-5A+11A-XBM-a (FIG. 4A). This can be explained by the cellulose-binding CBM2 in Cel5A, which targets the cellulase to the cellulose substrate, leading to more efficient degradation. The combination of f-5A+11A-XBM-a is also more active than f-5A+11A-a, suggesting that the lack of XBM has a negative influence on the capacity of the enzymes to degrade straw. The addition of the matching single cohesin-bearing CBM to the dockerin-containing enzymes, improved their specific activity, by returning the cellulose-targeting feature to the enzyme. In fact, in the case of the f-5A+11A-XBM-a combination, the wild-type enzyme activity was almost fully recovered by restoration of the targeting function. In both cases, incorporation of the enzymes into designer cellulosomes served to increase the activity substantially. The resultant enhancement in enzyme activity can be attributed to the proximity effect between the enzymes in the designer cellulosome. Although f-5A+11A-a was still less efficient than the wild-type enzymes, the combination of f-5A+11A-XBM-a gave a 1.5-fold enhancement compared to the wild-type T. fusca enzymes, thus demonstrating the impact of assembling the enzymes together into a designer cellulosome complex. This also suggests that the XBM in the xylanase 11A provides a major contribution to the overall degradation of the complex cellulosic substrate.

Similar results were also obtained for the combination of the two xylanases as well as for the three-enzyme system (FIGS. 4B and 4C). In the free state, wild-type enzymes always degraded straw more efficiently than the dockerin-bearing chimeras, due to the fact that in most cases the dockerin replaces the CBM, which has an important influence (substrate targeting) on the activity. Reactions involving 11A-a showed very weak activities, demonstrating once again the crucial role of the XBM.

Connecting each enzyme to its matching single-cohesin scaffoldin improved activity in each case, confirming the CBM effect. Furthermore, as observed in the combined Xyn11A+Cel5A interaction, placing the enzymes in close proximity via the scaffoldin unit had a significant positive impact on the specific activity. Likewise, complexation of the xylanases (11A-XBM-a+10B-t) and the three-enzyme system (11A-XBM-a+10B-t+f-5A) provided activity enhancements of approximately 1.6 and 1.5 fold, respectively, relative to the wild-type enzymes. Nevertheless, complexes including 11A-a showed markedly reduced levels of activity compared to that of the wild-type enzymes.

Interestingly, parallel experiments using soluble and insoluble xylan as substrates showed no apparent difference between free or complexed enzymes (data not shown), thus reinforcing the theory that designer cellulosomes are advantageous on complex substrates relative to free enzymes.

Figure 5:
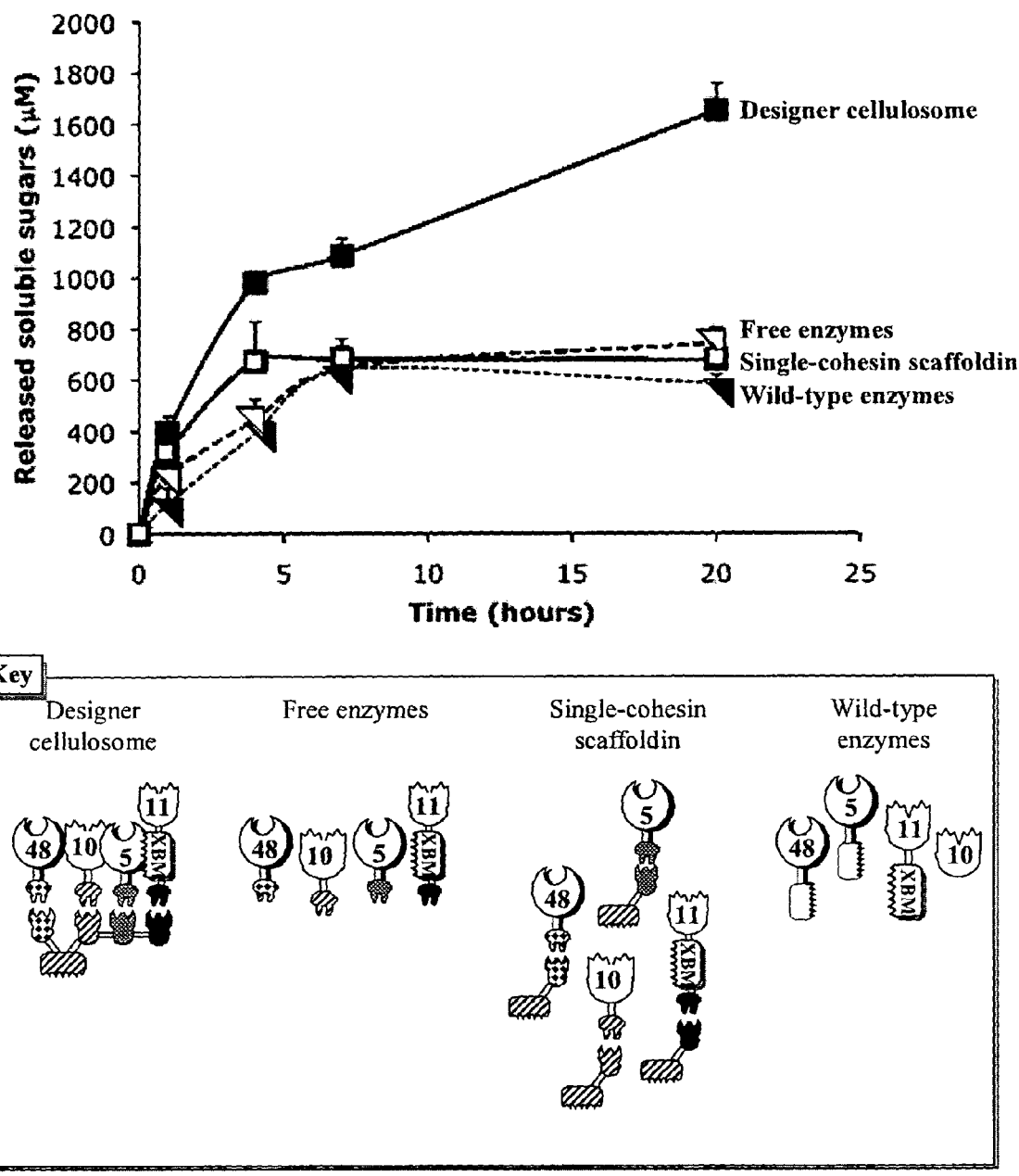
FIG. 5. Kinetics studies of hatched-straw hydrolysis by the various complexes and free enzyme systems. The black square curve represents the scaffoldin-bound enzyme complexes (designer cellulosomes), the white triangle curve represents the free enzyme system (lacking CBMs), the white square curve represents the chimeric enzymes attached to single-cohesin scaffoldin (CBM added extraneously) and the black triangle curve represents the wild-type enzymes (containing native CBMs). Triplicates of each reaction were carried out. Error bars are indicated.

C. Enzymatic Assays of Quadri-Functional Designer Cellulosomes on Hatched Wheat Straw The activity of the quadri-functional complex on straw is shown in FIG. 5. Control kinetics with the corresponding free enzymes systems (wild-type enzymes or cellulosomal-like enzymes) and the corresponding four single enzyme attached to the cohesin-CBM were performed. Compared with the designer cellulosome, the various samples were found to be less active on straw, indeed the close proximity within the four types of enzymes induced a drastic increase in the enzymatic activity of the complex, especially after 4 hours of degradation. Organizing the enzymes into designer cellulosomes is, in that case more than a success. As observed in FIG. 5, the various samples were found to be less active on wheat straw in comparison with the designer cellulosome complex, which exhibited a ~2.4 fold enhancement compared to the other enzyme mixtures after 20 h of degradation. No significant difference was observed between straw degradation by single-cohesin scaffoldin bearing enzymes, the chimeric enzymes and the wild-types enzymes after 7 hours of degradation.

D. Evaluation of the Proximity Effect Between Cellulases and Xylanases

Figure 6:
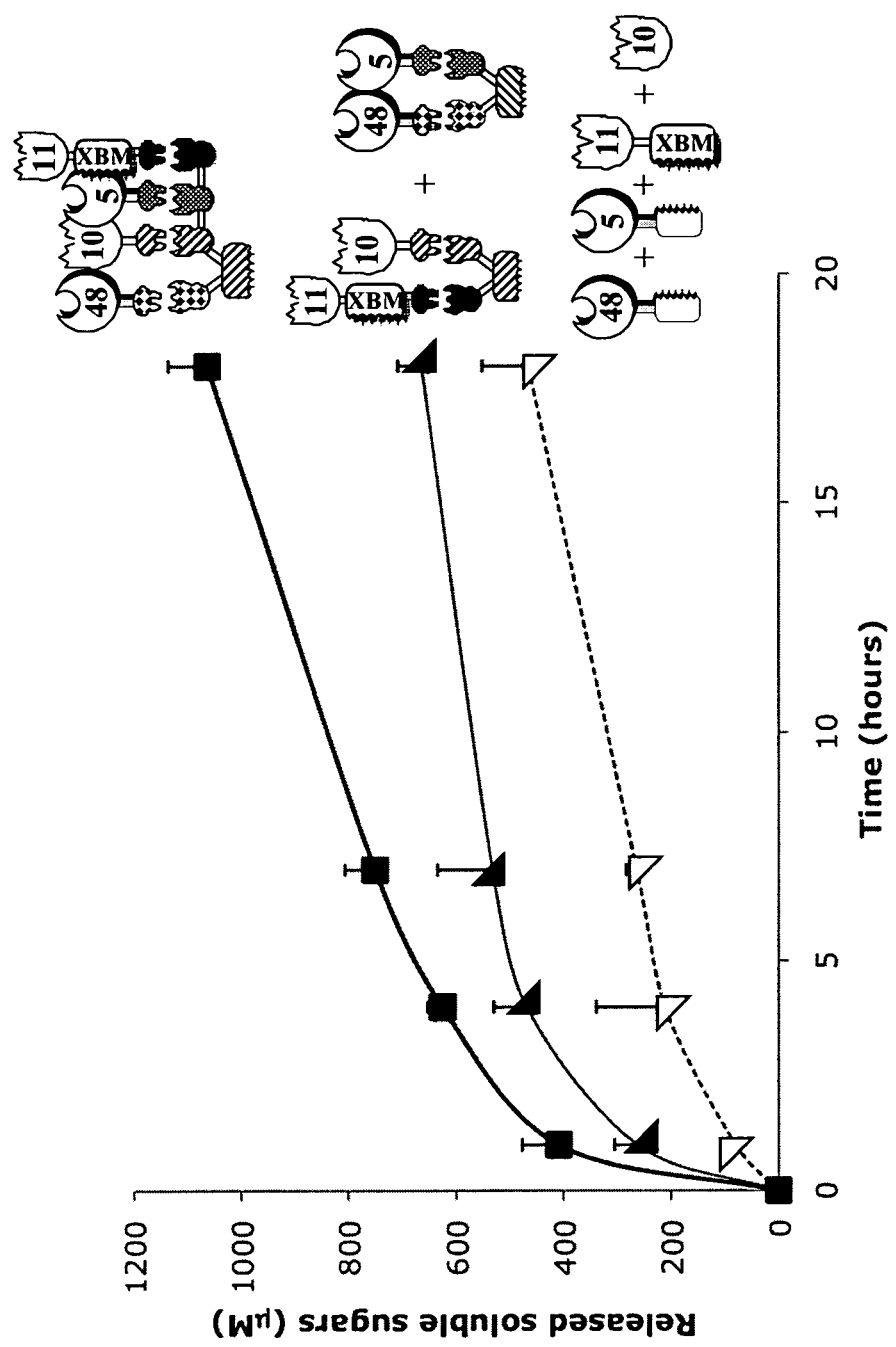
FIG. 6. Kinetics studies of hatched-straw hydrolysis by the various complexes and free enzyme systems. The black square curve represents the degradation by a single quadrifunctional designer cellulosome complex bearing the four enzymes, the black triangle curve represents the degradation by two bi-functional designer cellulosomes complexes: one bearing the cellulases and the other bearing the xylanases, and the white triangle curve represents the degradation by the free wild-type enzymes. Triplicates of each reaction were carried out. Error bars are indicated.

The two described chimeric xylanases 10B-t and 11A-a were incorporated into an appropriate scaffoldin and the two chimeric cellulases, f-5A and b-48A were integrated in a second scaffoldin. Using this approach, it was possible to estimate the differences in substrate degradation between the mixture of the two scaffoldins (cellulase- or xylanase-containing) and a third scaffoldin bearing the four enzymes (FIG. 6). In this manner, the proximity effect between cellulases and xylanases was evaluated by comparing the hydrolysis rates of each reaction. Interestingly, a significant improvement in enzymatic activity was demonstrated in the case of the four-enzyme scaffoldin compared to the mixture of the two distinct scaffoldins (~2 fold enhancement). At a lower level, the mixture of the two distinct designer cellulosome systems also provided an enhanced rate of degradation compared to the wild-type enzymes (~1.5 fold enhancement).

Example 6

Sugar Identification and Analysis

Methods

Analysis of sugar content was performed using a high-performance anion exchange chromatography (HPAEC) system equipped with a PA1 column (Dionex, Sunnyvale, Calif., USA). Reaction mixtures were loaded onto the column and eluted with NaOH (200 mM). Sugar concentrations were determined by integration of the chromatographic peaks, based on arabinose, xylose, xylobiose, xylotriose and cellobiose standards. Low levels of arabinose and xylose were observed in blanks (double-distilled water); these values were deducted in all the samples.

Xylose concentrations were confirmed by a D-xylose assay kit purchased from Megazyme (Wicklow, Ireland); glucose (absence thereof) was determined using a Glucose Assay Kit GAGO20 (Sigma-Aldrich); in both cases, according to the manufacturer's instructions.

Results

Sugar concentration and identification was performed using known concentrations of standards, and the relative amounts were calculated via integration of the identified peaks in the given samples. Combinations of free and scaffoldin-borne enzymes were applied to samples of hatched wheat straw, and the degradation products analyzed. Various quantities of arabinose, cellobiose, xylose, xylobiose and xylotriose were found in the samples (Tables 2 and 3). In accordance with the findings described in FIG. 3, Xyn10B and Cel5A were essentially inactive on the wheat straw substrate. In contrast, Xyn11A alone produced significant amounts of xylotriose, xylobiose and xylose, as well as arabinose but not cellobiose or glucose (Table 2), indicating its specificity for xylan. Many xylanases exhibit residual activity towards L-arabinose, due to the structural similarities between a-L-arabinofuranoside and b-D-xylopyranoside. The addition of Xyn10B or Cel5A appeared to drive the interaction more to completion, as no xylotriose was evident in these samples. The presence of Cel5A in the reaction mixtures resulted in significant quantities of cellobiose production, which was absent in samples lacking the cellulase. Incorporation of the dockerin-containing enzyme derivatives into chimeric scaffoldins served to enhance the levels of disaccharides and arabinose at the expense of xylose.

As seen on Table 3, incorporation of the dockerin-containing enzyme derivatives into two chimeric scaffoldins served to enhance the levels of cellobiose and xylotriose at the expense of xylobiose and arabinose relative to wild-type enzymes degradation. However, the levels of all sugars were higher in the quadri-functional designer cellulosomes in accordance with reducing sugars levels described in FIG. 6.

TABLE 2

Sugar concentration (in mmoles/g substrate), obtained by HPLC analysis following digestion of hatched wheat straw for 17 hours by various enzyme combinations.[a]

| Enzyme combination | Arabinose | Xylose | Xylobiose | Cellobiose | Xylotriose |
|---|---|---|---|---|---|
| Xyn11A | 20.3 ± 0.4 | 49.3 ± 0.5 | 7.9 ± 0.9 | n.d. | 41.7 ± 1.2 |
| Xyn10B | n.d.[b] | n.d. | n.d. | n.d. | n.d. |
| Cel5A | n.d. | n.d. | n.d. | n.d. | n.d. |
| Xyn11A + Xyn10B | 23.6 ± 0.5 | 42.7 ± 0.0 | 24.6 ± 1.2 | n.d. | n.d. |
| Scaf(11A-XBM-a + 10B-t) | 26.7 ± 0.2 | 34.7 ± 0.2 | 33.7 ± 0.2 | n.d. | n.d. |
| Xyn11A + Cel5A | 21.5 ± 0.4 | 41.5 ± 0.3 | 24.4 ± 1.1 | 20.6 ± 1.3 | n.d. |
| Scaf(11A-XBM-a + f-5A) | 24.2 ± 0.0 | 20 ± 0.5 | 32.4 ± 2.0 | 22.2 ± 0.5 | n.d. |
| Xyn11A + Xyn10B + Cel5A | 24.3 ± 0.2 | 48 ± 0.0 | 20.2 ± 1.7 | 21.8 ± 1.4 | n.d. |
| Scaf(11A-XBM-a + 10B-t + f-5A) | 31 ± 0.3 | 33.3 ± 0.1 | 24.8 ± 1.3 | 27.3 ± 0.7 | n.d. |

[a]Absence of glucose was confirmed by using a glucose assay kit. Values for xylose were corroborated using a xylose assay kit. An unidentified peak, present only after enzymatic treatments, eluted at ~3.9 min (between the xylose and xylobiose peaks), suggesting a monosaccharide, more likely a modified monosaccharide.
[b]n.d., not detected.
[c]Scaf indicates that the designated chimeric enzymes are complexed to the scaffoldin

TABLE 3

Sugar concentration (in mmoles/g substrate), obtained by HPLC analysis following digestion of hatched wheat straw for 17 hours by various enzyme combinations.[a]

| Enzyme combination | Arabinose | Xylose | Xylobiose | Cellobiose | Xylotriose |
|---|---|---|---|---|---|
| Xyn11A + Xyn10B + Cel5A + Cel48A | 45.7 ± 0.4 | 45.7 ± 1.7 | 68.6 ± 2.1 | 137.1 ± 3.9 | 10.9 ± 1 |
| Scaf (11A-XBM-a + 10B-t) + Scaf (f-5A + b-48A) | 42.8 ± 3 | 34.2 ± 2 | 45.7 ± 5.5 | 168.6 ± 5.6 | 27.1 ± 1.8 |
| Scaf (11A-XBM-a + 10B-t + f-5A + b-48A) | 45.7 ± 1.1 | 51.4 ± 0.8 | 111.4 ± 2.6 | 180 ± 2.8 | 30.6 ± 1.5 |

[a]Absence of glucose was confirmed by using a glucose assay kit. Values for xylose were corroborated using a xylose assay kit. An unidentified peak, present only after enzymatic treatments, eluted at ~3.9 min (between the xylose and xylobiose peaks), suggesting a monosaccharide, more likely a modified monosaccharide.
[b]Scaf indicates that the designated chimeric enzymes are complexed to the scaffoldin Yield Calculations:

Fierobe and colleagues (Fierobe et al. 2005 J. Biol. Chem. 280:16325-16334) analyzed the wheat straw composition after sulfuric acid treatment. The washed straw was found to contain 3.3 mmol of acid-extractable reducing sugars/g of dry matter using the Park and Johnson method (Park et al. 1949 J. Biol. Chem. 181:149-151). Quantification of glucose by high performance liquid chromatography analysis and the glucose oxidase method indicated that the substrate contains approximately 40% cellulose (2.3 mmol of glucose/g of dry matter). The content of xylose was found to be 0.8 mmol/g of dry matter, whereas the amount of arabinose was around 0.1 mmol/g. Accordingly, reaction yields after 17 h comprised about 8.2% and 9.6% for the bi- and tri-enzyme designer cellulosome system, respectively (versus the corresponding yields, 4.9% and 6.3%, of the wild-type enzymes). Accordingly, reaction yield after 20 h comprised about 10.3% for the quadri-functional designer cellulosome system versus the corresponding yield 4.2% for the wild-type enzymes). Since the straw substrate was only physically pretreated, this yield corresponds to a high-quality hydrolysis.

Example 7

Disposition of the XBM

Figure 7:
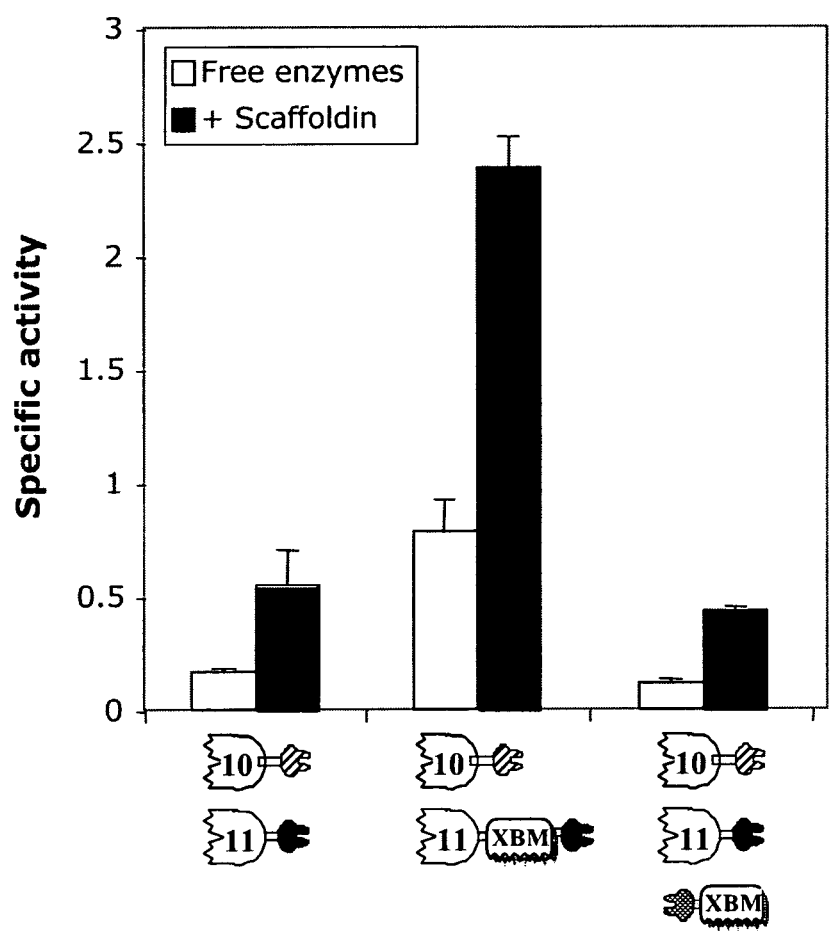
FIG. 7. Analysis of the influence of scaffoldin-borne versus native (enzyme-borne) XBM on degradation of wheat straw. The composition of the complexes and free enzymes systems is indicated at the bottom of the graph. White encoded bars represent the free enzyme system and black bars the scaffoldin-bound enzyme complexes. Specific activity is defined as µM reducing sugar per min per µM enzyme. Triplicates of each reaction were carried out, and standard deviations for straw hydrolysis are indicated.

In order to examine whether the importance of the XBM resides in the structural conformation of Xyn11A or reflects the mere presence of that particular CBM in the complex, a scaffoldin was designed that would include XBM together with a dockerin. The dockerin of *R. flavefaciens* was attached to the N-terminal end of the XBM from Xyn11A, in order to effect its physical separation from the catalytic module. Three complexes were tested for examination of the extrinsic contribution of the XBM to straw degradation (FIG. 7): (i) 11A-a+10B-t, as a negative control for an XBM-lacking system, (ii) 11A-XBM-a+10B-t as a positive control for XBM-containing system, and (iii) the designer cellulosome (11A-a+10B-t+f-XBM). The results clearly demonstrate that the structural conformation of 11A-XBM-a is responsible for the enhancement of activity and synergism between the two enzymes. Thus, function of the XBM is dependent on its presence in the native enzyme, since independent addition of the dockerin-fused XBM to higher-order designer cellulosomes had little or no effect on the activity on wheat straw. Both free systems and scaffoldin-bound designer cellulosome systems remained in the same range of efficiency as that of the 10B-t+11A-a system, which did not contain XBM.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A bio-engineered multi-enzyme complex comprising:
   (i) a scaffold polypeptide comprising a plurality of cohesin domains of divergent specificities and at least one substrate-binding module; and
   (ii) a plurality of carbohydrate active enzymes bound to said scaffold polypeptide, each carbohydrate active enzyme comprises a divergent dockerin domain matching one of the plurality of cohesin domains of the scaffold polypeptide;
wherein the plurality of carbohydrate active enzymes comprise at least two different xylanases, wherein at least one of the two different xylanases is a non-cellulosomal xylanase bio-engineered with a heterologous dockerin domain.

2. The bio-engineered multi-enzyme complex of claim 1, wherein the heterologous dockerin domain replaces at least one of the ancillary modules originally found in the enzyme structure; or wherein the heterologous dockerin domain is introduced in addition to the original ancillary modules.

3. The bio-engineered multi-enzyme complex of claim 1, wherein the dockerin domain is selected from the group consisting of a dockerin derived from *Clostridium thermocellum*, a dockerin derived from *Acetivibrio cellulolyticus*, a dockerin derived from *Ruminococcus flavefaciens*, a dockerin derived from *Bacteroides cellulosolvens*, a dockerin derived from *Archaeoglobus fulgidus* and a dockerin derived from *Clostridium cellulolyticum*.

4. The bio-engineered multi-enzyme complex of claim 1, wherein the non-cellulosomal xylanase is a *Thermobifida fusca* xylanase.

5. The bio-engineered multi-enzyme complex of claim 1, wherein the plurality of carbohydrate active enzymes further comprises at least one carbohydrate active enzyme selected from the group consisting of a glycoside hydrolase, polysaccharide lyase and carbohydrate esterase, wherein the at least one carbohydrate active enzyme is other than a xylanase.

6. The bio-engineered multi-enzyme complex of claim 5, wherein the at least one carbohydrate active enzyme is a cellulase classified in a glycoside hydrolase family selected from the group consisting of: family 5, 6, 7, 8, 9, 12, 26, 44, 45, 48, 51, 61, and 74.

7. The bio-engineered multi-enzyme complex of claim 6, wherein at least one of the cellulases present in the complex is a *T. fusca* cellulase.

8. The bio-engineered multi-enzyme complex of claim 1, wherein the complex is selected from the group consisting of: tri-functional and quadri-functional.

9. A composition for degrading biomass comprising the multi-enzyme complex of claim 1.

10. A genetically modified host cell comprising polynucleotides encoding a plurality of components of the bio-engineered multi-enzyme complex of claim 1, wherein the plurality of components comprise at least two different xylanases, wherein at least one of the two different xylanases is a non-cellulosomal xylanase bio-engineered with a heterologous dockerin domain.

11. A method for bioconversion of cellulosic material into degradation products, the method comprising exposing said cellulosic material to the multi-enzyme complex of claim 1.

12. A system for bioconversion of cellulosic material, the system comprising a multi-enzyme complex of claim 1.

13. The bio-engineered multi-enzyme complex of claim 1, wherein the at least two different xylanases are non-cellulosomal xylanases, each bio-engineered with a heterologous dockerin domain.

14. The bio-engineered multi-enzyme complex of claim 13, wherein the two non-cellulosomal xylanases are *T. fusca* xylanases.

* * * * *

SEQUENCE LISTING

<160> NUMBER OF SEQ ID NOS: 87

<210> SEQ ID NO 1
<211> LENGTH: 399
<212> TYPE: PRT
<213> ORGANISM: Thermobifida fusca

<400> SEQUENCE: 1

```
Met Lys Pro Val Arg Leu Ile Thr Ala Ala Leu Thr Thr Ala Val Leu
1               5                   10                  15

Ser Leu Pro Leu Met Val Val Pro Ala Ser Ala Gly Pro Val His Asp
            20                  25                  30

His His Pro Ala Pro His Ser Asn Ala Lys Ser Glu Arg Leu Arg Trp
        35                  40                  45

Ala Ala Pro Asp Gly Phe Tyr Ile Gly Ser Ala Val Ala Gly Gly Gly
    50                  55                  60

His His Leu Glu Gln Asp Tyr Pro Asp Pro Phe Thr His Asp Gly Lys
65                  70                  75                  80

Tyr Arg Ser Ile Leu Ala Gln Gln Phe Ser Ser Val Ser Pro Glu Asn
                85                  90                  95

Gln Met Lys Trp Glu Tyr Ile His Pro Glu Pro Asp Arg Tyr Asp Phe
            100                 105                 110

Ala Met Ala Asp Lys Ile Val Asp Phe Ala Glu Arg Asn Asp Gln Lys
        115                 120                 125

Val Arg Gly His Thr Leu Leu Trp His Ser Gln Asn Pro Glu Trp Leu
    130                 135                 140

Glu Glu Gly Asp Tyr Ser Pro Glu Glu Leu Arg Glu Ile Leu Arg Asp
145                 150                 155                 160

His Ile Thr Thr Val Val Gly Arg Tyr Ala Gly Arg Ile His Gln Trp
                165                 170                 175

Asp Val Ala Asn Glu Ile Phe Asp Glu Gln Gly Asn Leu Arg Thr Gln
            180                 185                 190

Glu Asn Ile Trp Ile Arg Glu Leu Gly Pro Gly Ile Ile Ala Asp Ala
        195                 200                 205

Phe Arg Trp Ala His Glu Ala Asp Pro Asn Ala Glu Leu Phe Phe Asn
    210                 215                 220

Asp Tyr Asn Val Glu Gly Ile Asn Pro Lys Ser Asp Ala Tyr Tyr Glu
225                 230                 235                 240

Leu Ile Gln Glu Leu Leu Asp Asp Gly Val Pro Val His Gly Phe Ser
                245                 250                 255

Val Gln Gly His Leu Ser Thr Arg Tyr Gly Phe Pro Gly Asp Leu Glu
            260                 265                 270

Gln Asn Leu Arg Arg Phe Asp Glu Leu Gly Leu Ala Thr Ala Ile Thr
        275                 280                 285

Glu Leu Asp Val Arg Met Asp Leu Pro Ala Ser Gly Lys Pro Thr Pro
    290                 295                 300

Lys Gln Leu Glu Gln Gln Ala Asp Tyr Gln Gln Ala Leu Glu Ala
305                 310                 315                 320

Cys Leu Ala Val Glu Gly Cys Asp Ser Phe Thr Ile Trp Gly Phe Thr
                325                 330                 335

Asp Lys Tyr Ser Trp Val Pro Val Phe Phe Pro Asp Glu Gly Ala Ala
            340                 345                 350

Thr Ile Met Thr Glu Lys Tyr Glu Arg Lys Pro Ala Phe Phe Ala Leu
        355                 360                 365
```

```
                Gln Gln Thr Leu Arg Glu Ala Arg Cys Ala Asp Ser Pro Lys Pro Gly
                    370                 375                 380

Pro Gly Lys Pro Lys Pro Gly Lys Gly Pro Lys His Asp His Cys
                385                 390                 395

<210> SEQ ID NO 2
<211> LENGTH: 1200
<212> TYPE: DNA
<213> ORGANISM: Thermobifida fusca

<400> SEQUENCE: 2
atgaaaccgg tgcgtctcat caccgccgcg ctcactactg cggtgctgtc tctcccctc        60 atggtggttc cgctagcgc gggaccggtc acgaccatc atcccgctcc ccactccaac       120
gcgaaatccg agcggctgcg ctgggctgcc cccgacggct tctacatcgg cagcgcggtc       180
gcgggcggcg gccaccacct ggagcaggac taccccgacc ccttcaccca cgacgggaaa       240
taccgcagca tcctggctca gcagttcagc tcagtctccc cggaaaacca gatgaagtgg       300
gagtacatcc atcctgagcc ggaccgctac gacttcgcca tggccgacaa gatcgtcgac       360
ttcgcggagc gtaacgacca gaaggtccgc ggtcacaccc tgctgtggca cagccagaac       420
cccgagtggc tcgaagaggg cgactactcc cctgaggagc tgcgcgagat cctgcgggac       480
cacatcacca ccgtggtcgg ccgctacgcc ggacggatcc accagtggga tgtggccaac       540
gagatcttcg acgagcaggg caacctgcgt actcaggaga catctggat ccgcgagctc       600 ggccccggca tcatcgctga cgcgttccgc tgggcgcacg aggcagaccc gaacgcggag       660
ctgttcttca cgactacaa cgtggagggc atcaacccga gagcgacgc ctactacgaa       720 ctcatccagg agctgctcga cgacggggtt ccggtccacg gcttctccgt ccaggggcac       780
ctgagcaccc gctacggctt cccgggcgac ctggaacaga acctgcgccg gttcgacgag       840
ctcggtctgg ccacggcgat caccgagctg gacgtgcgca tggacctgcc ggccagcggc       900
aagccgaccc cgaagcagtt ggagcagcag gccgactact accagcaggc gcttgaagcg       960
tgcctggccg tggaaggctg cgactccttc acgatctggg gcttcacgga caagtactcc      1020
tgggtgccgg tgttcttccc cgacgagggc gcggcgacga tcatgacgga agagtacgag      1080
cgcaagcccg ctttcttcgc gctgcagcag acgctgcggg aagcccggtg cgcggacagc      1140
cccaagccgg gaccgggcaa gccgaagccg ggcaagggcc caagcacga tcactgctga      1200

<210> SEQ ID NO 3
<211> LENGTH: 338
<212> TYPE: PRT
<213> ORGANISM: Thermobifida fusca

<400> SEQUENCE: 3

Met Asn His Ala Pro Ala Ser Leu Lys Ser Arg Arg Phe Arg Pro
1               5                   10                  15

Arg Leu Leu Ile Gly Lys Ala Phe Ala Ala Leu Val Ala Val
            20                  25                  30

Thr Met Ile Pro Ser Thr Ala Ala His Ala Ala Val Thr Ser Asn Glu
        35                  40                  45

Thr Gly Tyr His Asp Gly Tyr Phe Tyr Ser Phe Trp Thr Asp Ala Pro
    50                  55                  60

Gly Thr Val Ser Met Glu Leu Gly Pro Gly Gly Asn Tyr Ser Thr Ser
65                  70                  75                  80

Trp Arg Asn Thr Gly Asn Phe Val Ala Gly Lys Gly Trp Ala Thr Gly
                85                  90                  95
```

-continued

Gly Arg Arg Thr Val Thr Tyr Ser Ala Ser Phe Asn Pro Ser Gly Asn
            100                 105                 110

Ala Tyr Leu Thr Leu Tyr Gly Trp Thr Arg Asn Pro Leu Val Glu Tyr
        115                 120                 125

Tyr Ile Val Glu Ser Trp Gly Thr Tyr Arg Pro Thr Gly Thr Tyr Met
    130                 135                 140

Gly Thr Val Thr Thr Asp Gly Gly Thr Tyr Asp Ile Tyr Lys Thr Thr
145                 150                 155                 160

Arg Tyr Asn Ala Pro Ser Ile Glu Gly Thr Arg Thr Phe Asp Gln Tyr
                165                 170                 175

Trp Ser Val Arg Gln Ser Lys Arg Thr Ser Gly Thr Ile Thr Ala Gly
            180                 185                 190

Asn His Phe Asp Ala Trp Ala Arg His Gly Met His Leu Gly Thr His
        195                 200                 205

Asp Tyr Met Ile Met Ala Thr Glu Gly Tyr Gln Ser Ser Gly Ser Ser
    210                 215                 220

Asn Val Thr Leu Gly Thr Ser Gly Gly Gly Asn Pro Gly Gly Gly Asn
225                 230                 235                 240

Pro Pro Gly Gly Gly Asn Pro Pro Gly Gly Gly Cys Thr Ala Thr
                245                 250                 255

Leu Ser Ala Gly Gln Gln Trp Asn Asp Arg Tyr Asn Leu Asn Val Asn
            260                 265                 270

Val Ser Gly Ser Asn Asn Trp Thr Val Thr Val Asn Val Pro Trp Pro
        275                 280                 285

Ala Arg Ile Ile Ala Thr Trp Asn Ile His Ala Ser Tyr Pro Asp Ser
    290                 295                 300

Gln Thr Leu Val Ala Arg Pro Asn Gly Asn Gly Asn Asn Trp Gly Met
305                 310                 315                 320

Thr Ile Met His Asn Gly Asn Trp Thr Trp Pro Thr Val Ser Cys Ser
                325                 330                 335

Ala Asn

<210> SEQ ID NO 4
<211> LENGTH: 1017
<212> TYPE: DNA
<213> ORGANISM: Thermobifida fusca

<400> SEQUENCE: 4
atgaaccatg cccccgccag tctgaagagc cggagacgct tccggcccag actgctcatc      60
ggcaaggcgt tcgccgcggc actcgtcgcg gtcgtcacga tgatcccag tactgccgcc     120
cacgcggccg tgacctccaa cgagaccggg taccacgacg gtacttcta ctcgttctgg     180
accgacgcgc tggaacggt ctccatggag ctgggccctg gcggaaacta cagcacctcc     240
tggcggaaca ccgggaactt cgtcgccggt aagggatggg ccaccggtgg ccgccggacc     300
gtgacctact ccgccagctt caacccgtcg ggtaacgcct acctgaccct ctacgggtgg     360
acgcggaacc cgctcgtgga gtactacatc gtcgaaagct ggggcaccta ccggcccacc     420
ggtacctaca tggcacggt gaccaccgac ggtggtacct acgacatcta caagaccacg     480
cggtacaacg cgccctccat cgaaggcacc cggaccttcg accagtactg gagcgtccgc     540
cagtccaagc ggaccagcgg taccatcacc gcgggaacc acttcgacgc gtgggcccgc     600
cacggtatgc acctcggaac ccacgactac atgatcatgg cgaccgaggg ctaccagagc     660
agcggatcct ccaacgtgac gttgggcacc agcggcggtg gaaaccccgg tggggcaac     720

```
cccccccggtg gcggcaaccc ccccggtggc ggtggctgca cggcgacgct gtccgcgggc     780
cagcagtgga acgaccgcta caacctcaac gtcaacgtca gcggctccaa caactggacc     840
gtgaccgtga acgttccgtg gccggcgagg atcatcgcca cctggaacat ccacgccagc     900
tacccggact cccagacctt ggttgccccgg cctaacggca acgcaacaa ctggggcatg     960 acgatcatgc acaacggcaa ctggacgtgg cccacggtgt cctgcagcgc caactag     1017
```

<210> SEQ ID NO 5
<211> LENGTH: 460
<212> TYPE: PRT
<213> ORGANISM: Artificial Sequence
<220> FEATURE:
<223> OTHER INFORMATION: Polypeptide

<400> SEQUENCE: 5

```
Met Ala Ser His His His His His His Gly Pro Val His Asp His
1               5                   10                  15

Pro Ala Pro His Ser Asn Ala Lys Ser Glu Arg Leu Arg Trp Ala Ala
            20                  25                  30

Pro Asp Gly Phe Tyr Ile Gly Ser Ala Val Ala Gly Gly His His
        35                  40                  45

Leu Glu Gln Asp Tyr Pro Asp Pro Phe Thr His Asp Gly Lys Tyr Arg
    50                  55                  60

Ser Ile Leu Ala Gln Gln Phe Ser Ser Val Ser Pro Glu Asn Gln Met
65                  70                  75                  80

Lys Trp Glu Tyr Ile His Pro Glu Pro Asp Arg Tyr Asp Phe Ala Met
                85                  90                  95

Ala Asp Lys Ile Val Asp Phe Ala Glu Arg Asn Asp Gln Lys Val Arg
            100                 105                 110

Gly His Thr Leu Leu Trp His Ser Gln Asn Pro Glu Trp Leu Glu Glu
        115                 120                 125

Gly Asp Tyr Ser Pro Glu Glu Leu Arg Glu Ile Leu Arg Asp His Ile
    130                 135                 140

Thr Thr Val Val Gly Arg Tyr Ala Gly Arg Ile His Gln Trp Asp Val
145                 150                 155                 160

Ala Asn Glu Ile Phe Asp Glu Gln Gly Asn Leu Arg Thr Gln Glu Asn
                165                 170                 175

Ile Trp Ile Arg Glu Leu Gly Pro Gly Ile Ile Ala Asp Ala Phe Arg
            180                 185                 190

Trp Ala His Glu Ala Asp Pro Asn Ala Glu Leu Phe Phe Asn Asp Tyr
        195                 200                 205

Asn Val Glu Gly Ile Asn Pro Lys Ser Asp Ala Tyr Tyr Glu Leu Ile
    210                 215                 220

Gln Glu Leu Leu Asp Asp Gly Val Pro Val His Gly Phe Ser Val Gln
225                 230                 235                 240

Gly His Leu Ser Thr Arg Tyr Gly Phe Pro Gly Asp Leu Glu Gln Asn
                245                 250                 255

Leu Arg Arg Phe Asp Glu Leu Gly Leu Ala Thr Ala Ile Thr Glu Leu
            260                 265                 270

Asp Val Arg Met Asp Leu Pro Ala Ser Gly Lys Pro Thr Pro Lys Gln
        275                 280                 285

Leu Glu Gln Gln Ala Asp Tyr Tyr Gln Gln Ala Leu Glu Ala Cys Leu
    290                 295                 300

Ala Val Glu Gly Cys Asp Ser Phe Thr Ile Trp Gly Phe Thr Asp Lys
```

```
            305                 310                 315                 320
Tyr Ser Trp Val Pro Val Phe Phe Pro Asp Glu Gly Ala Ala Thr Ile
                325                 330                 335

Met Thr Glu Lys Tyr Glu Arg Lys Pro Ala Phe Phe Ala Leu Gln Gln
                340                 345                 350

Thr Leu Arg Glu Ala Arg Cys Ala Asp Ser Pro Lys Pro Gly Pro Gly
                355                 360                 365

Lys Pro Lys Pro Gly Lys Gly Pro Lys His Asp His Cys Thr Ser Thr
    370                 375                 380

Tyr Lys Val Pro Gly Thr Pro Ser Thr Lys Leu Tyr Gly Asp Val Asn
385                 390                 395                 400

Asp Asp Gly Lys Val Asn Ser Thr Asp Ala Val Ala Leu Lys Arg Tyr
                405                 410                 415

Val Leu Arg Ser Gly Ile Ser Ile Asn Thr Asp Asn Ala Asp Leu Asn
                420                 425                 430

Glu Asp Gly Arg Val Asn Ser Thr Asp Leu Gly Ile Leu Lys Arg Tyr
                435                 440                 445

Ile Leu Lys Glu Ile Asp Thr Leu Pro Tyr Lys Asn
    450                 455                 460

<210> SEQ ID NO 6
<211> LENGTH: 1383
<212> TYPE: DNA
<213> ORGANISM: Artificial Sequence
<220> FEATURE:
<223> OTHER INFORMATION: Polynucleotide

<400> SEQUENCE: 6
atggctagcc atcaccatca ccatcacgga ccggtccacg accatcatcc cgctccccac        60
tccaacgcga atccgagcg  gctgcgctgg gctgccccg  acggcttcta catcggcagc       120
gcggtcgcgg gcggcggcca ccacctggag caggactacc ccgacccctt cacccacgac       180
gggaaatacc gcagcatcct ggctcagcag ttcagctcag tctccccgga aaaccagatg       240
aagtgggagt acatccatcc tgagccggac cgctacgact cgccatggc  cgacaagatc       300 gtcgacttcg cggagcgtaa cgaccagaag gtccgcggtc acaccctgct gtggcacagc       360
cagaaccccg agtggctcga gagggcgac  tactcccctg aggagctgcg cgagatcctg       420
cgggaccaca tcaccaccgt ggtcggccgc tacgccggac ggatccacca gtgggatgtg       480
gccaacgaga tcttcgacga gcagggcaac ctgcgtactc aggagaacat ctggatccgc       540
gagctcggcc ccggcatcat cgctgacgcg ttccgctggg cgcacgaggc agacccgaac       600
gcggagctgt tcttcaacga ctacaacgtg gagggcatca acccgaagag cgacgcctac       660
tacgaactca tccaggagct gctcgacgac ggggttccgg tccacggctt ctccgtccag       720
gggcacctga gcacccgcta cggcttcccg ggcgacctgg aacagaacct cgccggttc       780 gacgagctcg gtctgccac  ggcgatcacc gagctgacg  tgcgcatgga cctgccggcc       840
agcggcaagc cgaccccgaa gcagttggag cagcaggccg actactacca gcaggcgctt       900
gaagcgtgcc tggccgtgga aggctgcgac tccttcacga tctggggctt cacggacaag       960
tactcctggg tgccggtgtt cttccccgac gagggcgcgg cgacgatcat gacggagaag      1020
tacgagcgca agcccgcttt cttcgcgctg cagcagacgc tgcgggaagc ccggtgcgcg      1080
gacagcccca gccgggacc  gggcaagccg aagccgggca agggcccaa  gcacgatcac      1140 tgtactagta catataaagt acctggtact ccttctacta aattatacgg cgacgtcaat      1200
```

```
gatgacggaa aagttaactc aactgacgct gtagcattga agagatatgt tttgagatca   1260
ggtataagca tcaacactga caatgccgat ttgaatgaag acggcagagt taattcaact   1320
gacttaggaa ttttgaagag atatattctc aaagaaatag atacattgcc gtacaagaac   1380
taa                                                                 1383
```

```
<210> SEQ ID NO 7
<211> LENGTH: 399
<212> TYPE: PRT
<213> ORGANISM: Artificial Sequence
<220> FEATURE:
<223> OTHER INFORMATION: Polypeptide

<400> SEQUENCE: 7

Met Ala Ser Met His His His His His Ala Val Thr Ser Asn Glu
1               5                   10                  15

Thr Gly Tyr His Asp Gly Tyr Phe Tyr Ser Phe Trp Thr Asp Ala Pro
            20                  25                  30

Gly Thr Val Ser Met Glu Leu Gly Pro Gly Gly Asn Tyr Ser Thr Ser
        35                  40                  45

Trp Arg Asn Thr Gly Asn Phe Val Ala Gly Lys Gly Trp Ala Thr Gly
    50                  55                  60

Gly Arg Arg Thr Val Thr Tyr Ser Ala Ser Phe Asn Pro Ser Gly Asn
65                  70                  75                  80

Ala Tyr Leu Thr Leu Tyr Gly Trp Thr Arg Asn Pro Leu Val Glu Tyr
                85                  90                  95

Tyr Ile Val Glu Ser Trp Gly Thr Tyr Arg Pro Thr Gly Thr Tyr Met
            100                 105                 110

Gly Thr Val Thr Thr Asp Gly Gly Thr Tyr Asp Ile Tyr Lys Thr Thr
        115                 120                 125

Arg Tyr Asn Ala Pro Ser Ile Glu Gly Thr Arg Thr Phe Asp Gln Tyr
    130                 135                 140

Trp Ser Val Arg Gln Ser Lys Arg Thr Ser Gly Thr Ile Thr Ala Gly
145                 150                 155                 160

Asn His Phe Asp Ala Trp Ala Arg His Gly Met His Leu Gly Thr His
                165                 170                 175

Asp Tyr Met Ile Met Ala Thr Glu Gly Tyr Gln Ser Ser Gly Ser Ser
            180                 185                 190

Asn Val Thr Leu Gly Thr Ser Gly Gly Asn Pro Gly Gly Gly Asn
        195                 200                 205

Pro Pro Gly Gly Gly Asn Pro Pro Gly Gly Gly Cys Thr Ala Thr
    210                 215                 220

Leu Ser Ala Gly Gln Gln Trp Asn Asp Arg Tyr Asn Leu Asn Val Asn
225                 230                 235                 240

Val Ser Gly Ser Asn Asn Trp Thr Val Thr Val Asn Val Pro Trp Pro
                245                 250                 255

Ala Arg Ile Ile Ala Thr Trp Asn Ile His Ala Ser Tyr Pro Asp Ser
            260                 265                 270

Gln Thr Leu Val Ala Arg Pro Asn Gly Asn Gly Asn Trp Gly Met
        275                 280                 285

Thr Ile Met His Asn Gly Asn Trp Thr Trp Pro Thr Val Ser Cys Ser
    290                 295                 300

Ala Asn Glu Leu Thr Ala Thr Thr Pro Thr Thr Pro Thr Thr
305                 310                 315                 320

Thr Pro Thr Pro Lys Phe Ile Tyr Gly Asp Val Asp Gly Asn Gly Ser
```

Val Arg Ile Asn Asp Ala Val Leu Ile Arg Asp Tyr Val Leu Gly Lys
             325                 330                 335

Ile Asn Glu Phe Pro Tyr Glu Tyr Gly Met Leu Ala Ala Asp Val Asp
    340                 345                 350

Gly Asn Gly Ser Ile Lys Ile Asn Asp Ala Val Leu Val Arg Asp Tyr
355                 360                 365

Val Leu Gly Lys Ile Phe Leu Phe Pro Val Glu Glu Lys Glu Glu
370                 375                 380

385                 390             395

<210> SEQ ID NO 8
<211> LENGTH: 1200
<212> TYPE: DNA
<213> ORGANISM: Artificial Sequence
<220> FEATURE:
<223> OTHER INFORMATION: Polynucleotide

<400> SEQUENCE: 8

```
atggctagca tgcaccatca ccatcaccac gccgtgacct ccaacgagac cgggtaccac      60
gacgggtact tctactcgtt ctggaccgac gcgcctggaa cggtctccat ggagctgggc     120
cctggcggaa actacagcac ctcctggcgg aacaccggga cttcgtcgc cggtaaggga     180
tgggccaccg gtggccgccg gaccgtgacc tactccgcca gcttcaaccc gtcgggtaac     240
gcctacctga ccctctacgg gtggacgcgg aacccgctcg tggagtacta catcgtcgaa     300
agctggggca cctaccggcc caccggtacc tacatgggca cggtgaccac cgacggtggt     360
acctacgaca tctacaagac cacgcggtac aacgcgccct ccatcgaagg cacccggacc     420
ttcgaccagt actggagcgt ccgccagtcc aagcggacca gcggtaccat caccgcgggg     480
aaccacttcg acgcgtgggc cgccacggt atgcacctcg aacccacga ctacatgatc     540
atggcgaccg agggctacca gagcagcgga tcctccaacg tgacgttggg caccagcggc     600
ggtggaaacc ccgtgggggg caacccccccc ggtggcggca acccccccgg tggcggtggc     660
tgcacggcga cgctgtccgc gggccagcag tggaacgacc gctacaacct caacgtcaac     720
gtcagcggct ccaacaactg gaccgtgacc gtgaacgttc cgtggccggc gaggatcatc     780
gccacctgga acatccacgc cagctacccg gactcccaga ccttggttgc ccggcctaac     840
ggcaacggca caactgggg catgacgatc atgcacaacg gcaactggac gtggcccacg     900
gtgtcctgca gcgccaacga gctcacagca actacaacac caactacaac accaactaca     960
acaccaacgc ctaaatttat atatggtgat gttgatggta atggaagtgt aagaattaat    1020
gatgctgtcc taataagaga ctatgtatta ggaaaaatca atgaattccc atatgaatat    1080
ggtatgcttg cagcagatgt tgatggtaat ggaagtataa aaattaatga tgctgttcta    1140
gtaagagact acgtgttagg aaagatattt ttattccctg ttgaagagaa agaagaataa    1200
```

<210> SEQ ID NO 9
<211> LENGTH: 466
<212> TYPE: PRT
<213> ORGANISM: Thermobifida fusca

<400> SEQUENCE: 9

Met Ala Lys Ser Pro Ala Ala Arg Lys Gly Gly Pro Pro Val Ala Val
1               5                   10                  15

Ala Val Thr Ala Ala Leu Ala Leu Leu Ile Ala Leu Leu Ser Pro Gly
            20                  25                  30

Val Ala Gln Ala Ala Gly Leu Thr Ala Thr Val Thr Lys Glu Ser Ser

-continued

```
                35                  40                  45
Trp Asp Asn Gly Tyr Ser Ala Ser Val Thr Val Arg Asn Asp Thr Ser
 50                  55                  60
Ser Thr Val Ser Gln Trp Glu Val Val Leu Thr Leu Pro Gly Gly Thr
 65                  70                  75                  80
Thr Val Ala Gln Val Trp Asn Ala Gln His Thr Ser Ser Gly Asn Ser
                     85                  90                  95
His Thr Phe Thr Gly Val Ser Trp Asn Ser Thr Ile Pro Pro Gly Gly
                100                 105                 110
Thr Ala Ser Phe Gly Phe Ile Ala Ser Gly Gly Glu Pro Thr His
                115                 120                 125
Cys Thr Ile Asn Gly Ala Pro Cys Asp Glu Gly Ser Glu Pro Gly Gly
 130                 135                 140
Pro Gly Gly Pro Gly Thr Pro Ser Pro Asp Pro Gly Thr Gln Pro Gly
 145                 150                 155                 160
Thr Gly Thr Pro Val Glu Arg Tyr Gly Lys Val Gln Val Cys Gly Thr
                165                 170                 175
Gln Leu Cys Asp Glu His Gly Asn Pro Val Gln Leu Arg Gly Met Ser
                180                 185                 190
Thr His Gly Ile Gln Trp Phe Asp His Cys Leu Thr Asp Ser Ser Leu
                195                 200                 205
Asp Ala Leu Ala Tyr Asp Trp Lys Ala Asp Ile Ile Arg Leu Ser Met
 210                 215                 220
Tyr Ile Gln Glu Asp Gly Tyr Glu Thr Asn Pro Arg Gly Phe Thr Asp
 225                 230                 235                 240
Arg Met His Gln Leu Ile Asp Met Ala Thr Ala Arg Gly Leu Tyr Val
                245                 250                 255
Ile Val Asp Trp His Ile Leu Thr Pro Gly Asp Pro His Tyr Asn Leu
                260                 265                 270
Asp Arg Ala Lys Thr Phe Phe Ala Glu Ile Ala Gln Arg His Ala Ser
                275                 280                 285
Lys Thr Asn Val Leu Tyr Glu Ile Ala Asn Glu Pro Asn Gly Val Ser
 290                 295                 300
Trp Ala Ser Ile Lys Ser Tyr Ala Glu Glu Val Ile Pro Val Ile Arg
 305                 310                 315                 320
Gln Arg Asp Pro Asp Ser Val Ile Ile Val Gly Thr Arg Gly Trp Ser
                325                 330                 335
Ser Leu Gly Val Ser Glu Gly Ser Gly Pro Ala Glu Ile Ala Ala Asn
                340                 345                 350
Pro Val Asn Ala Ser Asn Ile Met Tyr Ala Phe His Phe Tyr Ala Ala
                355                 360                 365
Ser His Arg Asp Asn Tyr Leu Asn Ala Leu Arg Glu Ala Ser Glu Leu
                370                 375                 380
Phe Pro Val Phe Val Thr Glu Phe Gly Thr Glu Thr Tyr Thr Gly Asp
 385                 390                 395                 400
Gly Ala Asn Asp Phe Gln Met Ala Asp Arg Tyr Ile Asp Leu Met Ala
                405                 410                 415
Glu Arg Lys Ile Gly Trp Thr Lys Trp Asn Tyr Ser Asp Phe Arg
                420                 425                 430
Ser Gly Ala Val Phe Gln Pro Gly Thr Cys Ala Ser Gly Gly Pro Trp
                435                 440                 445
Ser Gly Ser Ser Leu Lys Ala Ser Gly Gln Trp Val Arg Ser Lys Leu
 450                 455                 460
```

Gln Ser
465

<210> SEQ ID NO 10
<211> LENGTH: 1401
<212> TYPE: DNA
<213> ORGANISM: Thermobifida fusca

<400> SEQUENCE: 10

```
tcaggactgg agcttgctcc gcacccactg tccggacgcc ttcagcgacg aaccgctcca        60
cgggccgccg gacgcgcagg tgcccggctg gaagaccgcg ccggaacgga agtcgtccga       120
gtagttccac ttggtccacc cgatcttccg ttccgccatc aggtcgatgt agcggtcggc       180
catctggaag tcgttggcgc cgtcaccggt gtaggtctcg gtgccgaact cggtgacgaa       240
gacccgggaac agctcggagg cctcacgcag cgcgttgagg tagttgtcgc ggtgcgaggc       300
cgcgtagaag tggaaggcgt acatgatgtt ggaggcgttg accgggttgg ccgcgatctc       360
ggcggggccg gagccttcgg agacgccgag cgacgaccag ccgcgggtgc ccacgatgat       420
caccgagtcg gggtcgcgct ggcggatcac cgggatgacc tcttcggcgt agctcttgat       480
ggaggcccag ctcactccgt tgggttcgtt ggcgatctcg tagagcacgt tggtcttgct       540
ggcgtggcgc tgggcgattt ccgcgaagaa ggtcttggcc cggtccaggt tgtagtgggg       600
atcgcccggg gtgaggatgt gccagtccac gatcacgtac aggccgcgcg ccgtggccat       660
gtcgatgagc tggtgcatcc ggtcggtgaa gccgcgcggg ttggtctcgt agccgtcttc       720
ctggatgtac atggacaggc ggatgatgtc ggccttccag tcgtaggcca gggcgtccag       780
cgagctgtcg gtcaggcagt ggtcgaacca ctggatgccg tgggtgctca tgccgcgcag       840
ttggaccggg ttgccgtgct cgtcgcagag ctgggtgccg cagacctgga ctttgccgta       900
ccgctcgacc ggggtgccgg tgccgggctg cgtgccgggg tcggggagg gggttccggg       960
accgccgggg ccgcccggct cggagccttc gtcgcagggg gcgccgttga tggtgcagtg      1020
ggtgggttcg ccgctgccgg aagcgatgaa gccgaaggag gcggtgcctc cgggcgggat      1080
ggtgctgttc caggaaaccc cggtgaaggt gtggagttg ccgctgctgg tgtgctgggc       1140
gttccacacc tgggccactg tagtgccgcc gggcagggtg aggacgacct cccactggga      1200
gacggtgctc gaggtgtcgt tgcggacggt gacggacgcg gagtagccgt tgtcccacga      1260
ggattctttg gtgactgtgg cggtgagacc ggcggcctgc gcgactccgg gggagaggag      1320
cgcgatcagc agggcgaggg ccgcggtcac cgcgacagcg accggagggc cgcccttccg      1380
ggcggcgggg gatttcgcca t                                                1401
```

<210> SEQ ID NO 11
<211> LENGTH: 984
<212> TYPE: PRT
<213> ORGANISM: Thermobifida fusca

<400> SEQUENCE: 11

Met Arg Ser Leu Leu Ser Pro Arg Arg Trp Arg Thr Leu Ala Ser Gly
1               5                   10                  15

Ala Leu Ala Ala Ala Leu Ala Ala Ala Val Leu Ser Pro Gly Val Ala
            20                  25                  30

His Ala Ala Val Ala Cys Ser Val Asp Tyr Asp Asp Ser Asn Asp Trp
        35                  40                  45

Gly Ser Gly Phe Val Ala Glu Val Lys Val Thr Asn Glu Gly Ser Asp
    50                  55                  60

```
Pro Ile Gln Asn Trp Gln Val Gly Trp Thr Phe Pro Gly Asn Gln Gln
 65                  70                  75                  80

Ile Thr Asn Gly Trp Asn Gly Val Phe Ser Gln Ser Gly Ala Asn Val
                 85                  90                  95

Thr Val Arg Tyr Pro Asp Trp Asn Pro Asn Ile Ala Pro Gly Ala Thr
            100                 105                 110

Ile Ser Phe Gly Phe Gln Gly Thr Tyr Ser Gly Ser Asn Asp Ala Pro
            115                 120                 125

Thr Ser Phe Thr Val Asn Gly Val Thr Cys Ser Gly Ser Gln Pro Ala
            130                 135                 140

Asn Leu Pro Pro Asp Val Thr Leu Thr Ser Pro Ala Asn Asn Ser Thr
145                 150                 155                 160

Phe Leu Val Asn Asp Pro Ile Glu Leu Thr Ala Val Ala Ser Asp Pro
                165                 170                 175

Asp Gly Ser Ile Asp Arg Val Glu Phe Ala Ala Asp Asn Thr Val Ile
                180                 185                 190

Gly Ile Asp Thr Thr Ser Pro Tyr Ser Phe Thr Trp Thr Asp Ala Ala
            195                 200                 205

Ala Gly Ser Tyr Ser Val Thr Ala Ile Ala Tyr Asp Asp Gln Gly Ala
            210                 215                 220

Arg Thr Val Ser Ala Pro Ile Ala Ile Arg Val Leu Asp Arg Ala Ala
225                 230                 235                 240

Val Ile Ala Ser Pro Pro Thr Val Arg Val Pro Gln Gly Gly Thr Ala
                245                 250                 255

Asp Phe Glu Val Arg Leu Ser Asn Gln Pro Ser Gly Asn Val Thr Val
            260                 265                 270

Thr Val Ala Arg Thr Ser Gly Ser Ser Asp Leu Thr Val Ser Ser Gly
            275                 280                 285

Ser Gln Leu Gln Phe Thr Ser Ser Asn Trp Asn Gln Pro Gln Lys Val
            290                 295                 300

Thr Ile Ala Ser Ala Asp Asn Gly Gly Asn Leu Ala Glu Ala Val Phe
305                 310                 315                 320

Thr Val Ser Ala Pro Gly His Asp Ser Ala Glu Val Thr Val Arg Glu
                325                 330                 335

Ile Asp Pro Asn Thr Ser Ser Tyr Asp Gln Ala Phe Leu Glu Gln Tyr
            340                 345                 350

Glu Lys Ile Lys Asp Pro Ala Ser Gly Tyr Phe Arg Glu Phe Asn Gly
            355                 360                 365

Leu Leu Val Pro Tyr His Ser Val Glu Thr Met Ile Val Glu Ala Pro
            370                 375                 380

Asp His Gly His Gln Thr Thr Ser Glu Ala Phe Ser Tyr Tyr Leu Trp
385                 390                 395                 400

Leu Glu Ala Tyr Tyr Gly Arg Val Thr Gly Asp Trp Lys Pro Leu His
                405                 410                 415

Asp Ala Trp Glu Ser Met Glu Thr Phe Ile Ile Pro Gly Thr Lys Asp
            420                 425                 430

Gln Pro Thr Asn Ser Ala Tyr Asn Pro Asn Ser Pro Ala Thr Tyr Ile
            435                 440                 445

Pro Glu Gln Pro Asn Ala Asp Gly Tyr Pro Ser Pro Leu Met Asn Asn
            450                 455                 460

Val Pro Val Gly Gln Asp Pro Leu Ala Gln Glu Leu Ser Ser Thr Tyr
465                 470                 475                 480
```

```
Gly Thr Asn Glu Ile Tyr Gly Met His Trp Leu Leu Asp Val Asp Asn
                485                 490                 495

Val Tyr Gly Phe Gly Phe Cys Gly Asp Gly Thr Asp Asp Ala Pro Ala
            500                 505                 510

Tyr Ile Asn Thr Tyr Gln Arg Gly Ala Arg Glu Ser Val Trp Glu Thr
            515                 520                 525

Ile Pro His Pro Ser Cys Asp Asp Phe Thr His Gly Gly Pro Asn Gly
            530                 535                 540

Tyr Leu Asp Leu Phe Thr Asp Asp Gln Asn Tyr Ala Lys Gln Trp Arg
545                 550                 555                 560

Tyr Thr Asn Ala Pro Asp Ala Asp Ala Arg Ala Val Gln Val Met Phe
                565                 570                 575

Trp Ala His Glu Trp Ala Lys Glu Gln Gly Lys Glu Asn Glu Ile Ala
            580                 585                 590

Gly Leu Met Asp Lys Ala Ser Lys Met Gly Asp Tyr Leu Arg Tyr Ala
            595                 600                 605

Met Phe Asp Lys Tyr Phe Lys Lys Ile Gly Asn Cys Val Gly Ala Thr
            610                 615                 620

Ser Cys Pro Gly Gly Gln Gly Lys Asp Ser Ala His Tyr Leu Leu Ser
625                 630                 635                 640

Trp Tyr Tyr Ser Trp Gly Gly Ser Leu Asp Thr Ser Ser Ala Trp Ala
                645                 650                 655

Trp Arg Ile Gly Ser Ser Ser Ser His Gln Gly Tyr Gln Asn Val Leu
            660                 665                 670

Ala Ala Tyr Ala Leu Ser Gln Val Pro Glu Leu Gln Pro Asp Ser Pro
            675                 680                 685

Thr Gly Val Gln Asp Trp Ala Thr Ser Phe Asp Arg Gln Leu Glu Phe
            690                 695                 700

Leu Gln Trp Leu Gln Ser Ala Glu Gly Gly Ile Ala Gly Gly Ala Thr
705                 710                 715                 720

Asn Ser Trp Lys Gly Ser Tyr Asp Thr Pro Thr Gly Leu Ser Gln
                725                 730                 735

Phe Tyr Gly Met Tyr Tyr Asp Trp Gln Pro Val Trp Asn Asp Pro Pro
            740                 745                 750

Ser Asn Asn Trp Phe Gly Phe Gln Val Trp Asn Met Glu Arg Val Ala
            755                 760                 765

Gln Leu Tyr Tyr Val Thr Gly Asp Ala Arg Ala Glu Ala Ile Leu Asp
            770                 775                 780

Lys Trp Val Pro Trp Ala Ile Gln His Thr Asp Val Asp Ala Asp Asn
785                 790                 795                 800

Gly Gly Gln Asn Phe Gln Val Pro Ser Asp Leu Glu Trp Ser Gly Gln
                805                 810                 815

Pro Asp Thr Trp Thr Gly Thr Tyr Thr Gly Asn Pro Asn Leu His Val
            820                 825                 830

Gln Val Val Ser Tyr Ser Gln Asp Val Gly Val Thr Ala Ala Leu Ala
            835                 840                 845

Lys Thr Leu Met Tyr Tyr Ala Lys Arg Ser Gly Asp Thr Thr Ala Leu
850                 855                 860

Ala Thr Ala Glu Gly Leu Leu Asp Ala Leu Leu Ala His Arg Asp Ser
865                 870                 875                 880

Ile Gly Ile Ala Thr Pro Glu Gln Pro Ser Trp Asp Arg Leu Asp Asp
                885                 890                 895

Pro Trp Asp Gly Ser Glu Gly Leu Tyr Val Pro Pro Gly Trp Ser Gly
```

```
                       900              905              910
Thr Met Pro Asn Gly Asp Arg Ile Glu Pro Gly Ala Thr Phe Leu Ser
        915                 920                 925

Ile Arg Ser Phe Tyr Lys Asn Asp Pro Leu Trp Pro Gln Val Glu Ala
        930                 935                 940

His Leu Asn Asp Pro Gln Asn Val Pro Ala Pro Ile Val Glu Arg His
945                 950                 955                 960

Arg Phe Trp Ala Gln Val Glu Ile Ala Thr Phe Ala Ala His Asp
                965                 970                 975

Glu Leu Phe Gly Ala Gly Ala Pro
        980

<210> SEQ ID NO 12
<211> LENGTH: 2955
<212> TYPE: DNA
<213> ORGANISM: Thermobifida fusca

<400> SEQUENCE: 12
atgagatcgt tactgtctcc ccggcgctgg cgcacgctgg cctcgggggc gctcgcagcg      60
gccctggccg ccgctgtact ctcccccggc gtcgcgcacg ccgccgtcgc ctgctcggtg     120
gactacgacg actccaacga ctggggtagc gggttcgtcg ccgaagtcaa ggtgaccaac     180
gaaggcagcg accccatcca gaactggcaa gtaggctgga ccttccccgg taaccagcag     240
atcaccaacg gctggaacgg cgtgttcagc cagagcggcg ccaacgtcac cgtccgctac     300
ccggactgga cccccaatat cgcccccgga gccaccatct ccttcggctt ccagggcacc     360
tacagcggct ccaacgacgc cccgaccagc ttcaccgtca acgcgtcac ctgcagcgga     420 tcccagcccg ccaacctgcc gcccgatgtc accctgacat cccggccaa caactcgacc     480 ttcctggtca cgacccgat cgagctgacc gcggtcgcct ccgaccccga cggctcgatc     540
gaccgggtgg aattcgccgc cgacaacacc gtcatcggca tcgacaccac ctcccccctac    600 agcttcacct ggacggacgc tgccgccggc tcctactcgg tgaccgcgat cgcctacgac     660
gaccagggag ccaggaccgt ctccgctccc atcgccatcc gagtgctgga cccgggccgcc   720 gtcatcgcct caccgcccac cgtccgcgtg ccgcaggggcg caccgccga cttcgaggtg    780 cggctgtcca accagccctc cggcaacgtc acggtcaccg tggcgcgcac gtcgggcagc    840
tccgacctga ccgtctccag cggctcccaa ctccagttca cctccagcaa ctggaaccag    900
ccgcagaagg tgaccatcgc ctccgctgac aacggcggaa acctggccga ggcggtcttc    960
accgtcagcg cccccggcca cgactcggcc gaggtgacgg tccgggagat cgaccccgaac  1020 accagctcct acgaccaggc cttcctggag cagtacgaga agatcaagga ccccgccagc   1080
ggctacttcc gcgaattcaa cgggctcctg gtcccctacc actcggtgga gaccatgatc   1140
gtcgaggctc cggaccacgg ccaccagacc acgtccgagg cgttcagcta ctacctgtgg    1200
ctggaggcgt actacggccg ggtcaccggt gactggaagc cgctccacga cgcctgggag    1260
tcgatggaga ccttcatcat ccccggcacc aaggaccagc cgaccaactc cgcctacaac    1320
ccgaactccc cggcgaccta catccccgag cagcccaacg ctgacggcta cccgtcgcct    1380
ctcatgaaca acgtcccggt gggtcaagac ccgctcgccc aggagctgag ctccacctac   1440
gggaccaacg agatctacgg catgcactgg ctgctcgacg tggacaacgt ctacggcttc    1500
gggttctgcg cgacggcac cgacgacgcc ccgcctaca tcaacaccta ccagcgtggt     1560
gcgcgcgagt cggtgtggga gaccattccg cacccgtcct gcgacgactt cacgcacggc   1620
```

```
ggccccaacg gctacctgga cctgttcacc gacgaccaga actacgccaa gcagtggcgc    1680
tacaccaacg cccccgacgc tgacgcgcgg gccgtccagg tgatgttctg ggcgcacgaa    1740
tgggccaagg agcagggcaa ggagaacgag atcgcgggcc tgatggacaa ggcgtccaag    1800
atgggcgact acctccggta cgcgatgttc gacaagtact tcaagaagat cggcaactgc    1860
gtcggcgcca cctcctgccc gggtggccaa ggcaaggaca gcgcgcacta cctgctgtcc    1920
tggtactact cctggggcgg ctcgctcgac acctcctctg cgtgggcgtg cgtatcggc    1980 tccagctcct cgcaccaggg ctaccagaac gtgctcgctg cctacgcgct ctcgcaggtg    2040
cccgaactgc agcctgactc cccgaccggt gtccaggact gggccaccag cttcgaccgc    2100
cagttggagt tcctccagtg gctgcagtcc gctgaaggtg gtatcgccgg tggcgccacc    2160
aacagctgga agggaagcta cgacaccccg ccgaccggcc tgtcgcagtt ctacggcatg    2220
tactacgact ggcagccggt ctggaacgac cgccgtcca caactggtt cggcttccag      2280 gtctggaaca tggagcgcgt cgcccagctc tactacgtga ccggcgacgc ccgggccgag    2340
gccatcctcg acaagtgggt gccgtgggcc atccagcaca ccgacgtgga cgccgacaac    2400
ggcggccaga acttccaggt cccctccgac ctggagtggt cgggccagcc tgacacctgg    2460
accggcacct acaccggcaa cccgaacctg cacgtccagg tcgtctccta cagccaggac    2520
gtcggtgtga ccgccgctct ggccaagacc ctgatgtact acgcgaagcg ttcgggcgac    2580
accaccgccc tcgccaccgc ggagggtctg ctggacgccc tgctggccca ccgggacagc    2640
atcggtatcg ccaccccga gcagccgagc tgggaccgtc tggacgaccc gtgggacggc    2700
tccgagggcc tgtacgtgcc gccgggctgg tcgggcacca tgcccaacgg tgaccgcatc    2760
gagccgggcg cgaccttcct gtccatccgc tcgttctaca agaacgaccc gctgtggccg    2820
caggtcgagg cacacctgaa cgacccgcag aacgtcccgg cgccgatcgt ggagcgccac    2880
cgcttctggg ctcaggtgga aatcgcgacc gcgttcgcag cccacgacga actgttcggg    2940
gccggagctc cctga                                                     2955
```

<210> SEQ ID NO 13
<211> LENGTH: 411
<212> TYPE: PRT
<213> ORGANISM: Artificial Sequence
<220> FEATURE:
<223> OTHER INFORMATION: Polypeptide

<400> SEQUENCE: 13

```
Met Ala His His His His His His Ala Pro Ser Pro Gly Thr Lys Leu
1               5                   10                  15

Val Pro Thr Trp Gly Asp Thr Asn Cys Asp Gly Val Val Asn Val Ala
            20                  25                  30

Asp Val Val Leu Asn Arg Phe Leu Asn Asp Pro Thr Tyr Ser Asn
        35                  40                  45

Ile Thr Asp Gln Gly Lys Val Asn Ala Asp Val Asp Pro Gln Asp
    50                  55                  60

Lys Ser Gly Ala Ala Val Asp Pro Ala Gly Val Lys Leu Thr Val Ala
65                  70                  75                  80

Asp Ser Glu Ala Ile Leu Lys Ala Ile Val Glu Leu Ile Thr Leu Pro
                85                  90                  95

Gln Ala Val Pro Gly Thr Gln Pro Gly Thr Gly Thr Pro Val Glu Arg
            100                 105                 110

Tyr Gly Lys Val Gln Val Cys Gly Thr Gln Leu Cys Asp Glu His Gly
        115                 120                 125
```

Asn Pro Val Gln Leu Arg Gly Met Ser Thr His Gly Ile Gln Trp Phe
    130                 135                 140

Asp His Cys Leu Thr Asp Ser Ser Leu Asp Ala Leu Ala Tyr Asp Trp
145                 150                 155                 160

Lys Ala Asp Ile Ile Arg Leu Ser Met Tyr Ile Gln Glu Asp Gly Tyr
                165                 170                 175

Glu Thr Asn Pro Arg Gly Phe Thr Asp Arg Met His Gln Leu Ile Asp
            180                 185                 190

Met Ala Thr Ala Arg Gly Leu Tyr Val Ile Val Asp Trp His Ile Leu
        195                 200                 205

Thr Pro Gly Asp Pro His Tyr Asn Leu Asp Arg Ala Lys Thr Phe Phe
210                 215                 220

Ala Glu Ile Ala Gln Arg His Ala Ser Lys Thr Asn Val Leu Tyr Glu
225                 230                 235                 240

Ile Ala Asn Glu Pro Asn Gly Val Ser Trp Ala Ser Ile Lys Ser Tyr
                245                 250                 255

Ala Glu Glu Val Ile Pro Val Ile Arg Gln Arg Asp Pro Asp Ser Val
            260                 265                 270

Ile Ile Val Gly Thr Arg Gly Trp Ser Ser Leu Gly Val Ser Glu Gly
        275                 280                 285

Ser Gly Pro Ala Glu Ile Ala Ala Asn Pro Val Asn Ala Ser Asn Ile
290                 295                 300

Met Tyr Ala Phe His Phe Tyr Ala Ala Ser His Arg Asp Asn Tyr Leu
305                 310                 315                 320

Asn Ala Leu Arg Glu Ala Ser Glu Leu Phe Pro Val Phe Val Thr Glu
                325                 330                 335

Phe Gly Thr Glu Thr Tyr Thr Gly Asp Gly Ala Asn Asp Phe Gln Met
            340                 345                 350

Ala Asp Arg Tyr Ile Asp Leu Met Ala Glu Arg Lys Ile Gly Trp Thr
        355                 360                 365

Lys Trp Asn Tyr Ser Asp Asp Phe Arg Ser Gly Ala Val Phe Gln Pro
370                 375                 380

Gly Thr Cys Ala Ser Gly Gly Pro Trp Ser Gly Ser Ser Leu Lys Ala
385                 390                 395                 400

Ser Gly Gln Trp Val Arg Ser Lys Leu Gln Ser
                405                 410

<210> SEQ ID NO 14
<211> LENGTH: 1236
<212> TYPE: DNA
<213> ORGANISM: Artificial Sequence
<220> FEATURE:
<223> OTHER INFORMATION: Polynucleotide

<400> SEQUENCE: 14
atggcacacc atcaccatca ccatgcacca tcacccggca caaagctcgt tcctacatgg      60
ggcgatacaa actgcgacgg cgttgtaaat gttgctgacg tagtagttct taacagattc     120
ctcaacgatc ctacatattc taacattact gatcagggta aggttaacgc agacgttgtt     180
gatcctcagg ataagtccgg cgcagcagtt gatcctgcag gcgtaaagct cacagtagct     240
gactctgagg caatcctcaa ggctatcgtt gaactcatca cacttcctca gcggtacccc     300
ggcacgcagc ccggcaccgg caccccggtc gagcggtacg gcaaagtcca ggtctgcggc     360
acccagctct gcgacgagca cggcaacccg gtccaactgc gcggcatgag cacccacggc     420

```
atccagtggt cgaccactg cctgaccgac agctcgctgg acgccctggc ctacgactgg    480
aaggccgaca tcatccgcct gtccatgtac atccaggaag acggctacga gaccaacccg    540
cgcggcttca ccgaccggat gcaccagctc atcgacatgg ccacggcgcg cggcctgtac    600
gtgatcgtgg actggcacat cctcaccccg ggcgatcccc actacaacct ggaccgggcc    660
aagaccttct cgcggaaat cgcccagcgc cacgccagca agaccaacgt gctctacgag     720
atcgccaacg aacccaacgg agtgagctgg gcctccatca agagctacgc cgaagaggtc    780
atcccggtga tccgccagcg cgaccccgac tcggtgatca tcgtgggcac ccgcggctgg    840
tcgtcgctcg gcgtctccga aggctccggc ccgccgagag tcgcggccaa cccggtcaac    900
gcctccaaca tcatgtacgc cttccacttc tacgcggcct cgcaccgcga caactacctc    960
aacgcgctgc gtgaggcctc cgagctgttc ccggtcttcg tcaccgagtt cggcaccgag   1020
acctacaccg gtgacggcgc caacgacttc agatggccg accgctacat cgacctgatg    1080
gcggaacgga agatcgggtg gaccaagtgg aactactcgg acgacttccg ttccggcgcg   1140
gtcttccagc cgggcacctg cgcgtccggc ggcccgtgga gcggttcgtc gctgaaggcg   1200
tccggacagt gggtgcggag caagctccag tcctga                             1236
```

<210> SEQ ID NO 15
<211> LENGTH: 749
<212> TYPE: PRT
<213> ORGANISM: Artificial Sequence
<220> FEATURE:
<223> OTHER INFORMATION: Polypeptide

<400> SEQUENCE: 15

```
Met Ala His His His His His His Pro Lys Gly Thr Ala Thr Val Leu
1               5                   10                  15

Tyr Gly Asp Val Asp Asn Asp Gly Asn Val Asp Ser Asp Tyr Ala
            20                  25                  30

Tyr Met Arg Gln Trp Leu Ile Gly Met Ile Ala Asp Phe Pro Gly Gly
        35                  40                  45

Asp Ile Gly Leu Ala Asn Ala Asp Val Asp Gly Asp Gly Asn Val Asp
    50                  55                  60

Ser Asp Asp Tyr Ala Tyr Met Arg Gln Trp Leu Ile Gly Met Ile Ser
65                  70                  75                  80

Glu Phe Pro Ala Glu Gln Lys Ala Val Pro Gly His Asp Ser Ala Glu
                85                  90                  95

Val Thr Val Arg Glu Ile Asp Pro Asn Thr Ser Ser Tyr Asp Gln Ala
            100                 105                 110

Phe Leu Glu Gln Tyr Glu Lys Ile Lys Asp Pro Ala Ser Gly Tyr Phe
        115                 120                 125

Arg Glu Phe Asn Gly Leu Leu Val Pro Tyr His Ser Val Glu Thr Met
    130                 135                 140

Ile Val Glu Ala Pro Asp His Gly His Gln Thr Thr Ser Glu Ala Phe
145                 150                 155                 160

Ser Tyr Tyr Leu Trp Leu Glu Ala Tyr Tyr Gly Arg Val Thr Gly Asp
                165                 170                 175

Trp Lys Pro Leu His Asp Ala Trp Glu Ser Met Glu Thr Phe Ile Ile
            180                 185                 190

Pro Gly Thr Lys Asp Gln Pro Thr Asn Ser Ala Tyr Asn Pro Asn Ser
        195                 200                 205

Pro Ala Thr Tyr Ile Pro Glu Gln Pro Asn Ala Asp Gly Tyr Pro Ser
    210                 215                 220
```

```
Pro Leu Met Asn Asn Val Pro Val Gly Gln Asp Pro Leu Ala Gln Glu
225                 230                 235                 240

Leu Ser Ser Thr Tyr Gly Thr Asn Glu Ile Tyr Gly Met His Trp Leu
            245                 250                 255

Leu Asp Val Asp Asn Val Tyr Gly Phe Gly Phe Cys Gly Asp Gly Thr
        260                 265                 270

Asp Asp Ala Pro Ala Tyr Ile Asn Thr Tyr Gln Arg Gly Ala Arg Glu
        275                 280                 285

Ser Val Trp Glu Thr Ile Pro His Pro Ser Cys Asp Asp Phe Thr His
290                 295                 300

Gly Gly Pro Asn Gly Tyr Leu Asp Leu Phe Thr Asp Asp Gln Asn Tyr
305                 310                 315                 320

Ala Lys Gln Trp Arg Tyr Thr Asn Ala Pro Asp Ala Asp Ala Arg Ala
            325                 330                 335

Val Gln Val Met Phe Trp Ala His Glu Trp Ala Lys Glu Gln Gly Lys
        340                 345                 350

Glu Asn Glu Ile Ala Gly Leu Met Asp Lys Ala Ser Lys Met Gly Asp
        355                 360                 365

Tyr Leu Arg Tyr Ala Met Phe Asp Lys Tyr Phe Lys Lys Ile Gly Asn
370                 375                 380

Cys Val Gly Ala Thr Ser Cys Pro Gly Gln Gly Lys Asp Ser Ala
385                 390                 395                 400

His Tyr Leu Leu Ser Trp Tyr Ser Trp Gly Gly Ser Leu Asp Thr
            405                 410                 415

Ser Ser Ala Trp Ala Trp Arg Ile Gly Ser Ser Ser His Gln Gly
        420                 425                 430

Tyr Gln Asn Val Leu Ala Ala Tyr Ala Leu Ser Gln Val Pro Glu Leu
        435                 440                 445

Gln Pro Asp Ser Pro Thr Gly Val Gln Asp Trp Ala Thr Ser Phe Asp
450                 455                 460

Arg Gln Leu Glu Phe Leu Gln Trp Leu Gln Ser Ala Glu Gly Gly Ile
465                 470                 475                 480

Ala Gly Gly Ala Thr Asn Ser Trp Lys Gly Ser Tyr Asp Thr Pro Pro
            485                 490                 495

Thr Gly Leu Ser Gln Phe Tyr Gly Met Tyr Tyr Asp Trp Gln Pro Val
        500                 505                 510

Trp Asn Asp Pro Pro Ser Asn Asn Trp Phe Gly Phe Gln Val Trp Asn
        515                 520                 525

Met Glu Arg Val Ala Gln Leu Tyr Tyr Val Thr Gly Asp Ala Arg Ala
        530                 535                 540

Glu Ala Ile Leu Asp Lys Trp Val Pro Trp Ala Ile Gln His Thr Asp
545                 550                 555                 560

Val Asp Ala Asp Asn Gly Gly Gln Asn Phe Gln Val Pro Ser Asp Leu
            565                 570                 575

Glu Trp Ser Gly Gln Pro Asp Thr Trp Thr Gly Thr Tyr Thr Gly Asn
        580                 585                 590

Pro Asn Leu His Val Gln Val Val Ser Tyr Ser Gln Asp Val Gly Val
        595                 600                 605

Thr Ala Ala Leu Ala Lys Thr Leu Met Tyr Tyr Ala Lys Arg Ser Gly
        610                 615                 620

Asp Thr Thr Ala Leu Ala Thr Ala Glu Gly Leu Leu Asp Ala Leu Leu
625                 630                 635                 640
```

```
Ala His Arg Asp Ser Ile Gly Ile Ala Thr Pro Glu Gln Pro Ser Trp
            645                 650                 655

Asp Arg Leu Asp Asp Pro Trp Asp Gly Ser Glu Gly Leu Tyr Val Pro
        660                 665                 670

Pro Gly Trp Ser Gly Thr Met Pro Asn Gly Asp Arg Ile Glu Pro Gly
    675                 680                 685

Ala Thr Phe Leu Ser Ile Arg Ser Phe Tyr Lys Asn Asp Pro Leu Trp
690                 695                 700

Pro Gln Val Glu Ala His Leu Asn Asp Pro Gln Asn Val Pro Ala Pro
705                 710                 715                 720

Ile Val Glu Arg His Arg Phe Trp Ala Gln Val Glu Ile Ala Thr Ala
                725                 730                 735

Phe Ala Ala His Asp Glu Leu Phe Gly Ala Gly Ala Pro
            740                 745
```

<210> SEQ ID NO 16
<211> LENGTH: 2250
<212> TYPE: DNA
<213> ORGANISM: Artificial Sequence
<220> FEATURE:
<223> OTHER INFORMATION: Polynucleotide

<400> SEQUENCE: 16

```
atggcccacc atcaccatca ccatccaaaa ggcacagcta cagtattata tggtgacgtt    60
gataatgatg gaaatgttga ttcagacgac tatgcatata tgagacaatg gttgatcggt   120
atgattgctg atttccctgg aggagatatc ggattagcta atgctgatgt tgatggagac   180
ggaaatgtag attcagatga ctatgcgtac atgagacaat ggttaatagg aatgatttcc   240
gagttcccag cagaacaaaa agcggtaccc ggccacgact cggccgaggt gacggtccgg   300
gagatcgacc cgaacaccag ctcctacgac caggccttcc tggagcagta cgagaagatc   360
aaggaccccg ccagcggcta cttccgcgaa ttcaacgggc tcctggtccc ctaccactcg   420
gtggagacca tgatcgtcga ggctccggac cacgccacc agaccacgtc cgaggcgttc   480
agctactacc tgtggctgga ggcgtactac ggccgggtca ccggtgactg aagccgctc    540
cacgacgcct gggagtcgat ggagaccttc atcatcccg gcaccaagga ccagccgacc   600
aactccgcct acaacccgaa ctccccggcg acctacatcc ccgagcagcc aacgctgac    660
ggctaccgt cgcctctcat gaacaacgtc ccggtgggtc aagacccgct cgcccaggag   720
ctgagctcca cctacgggac caacgagatc tacggcatgc actggctgct cgacgtggac   780
aacgtctacg gcttcgggtt ctgcggcgac ggcaccgacg acgcccccgc ctacatcaac   840
acctaccagc gtggtgcgcg cgagtcggtg tgggagacca ttccgcaccc gtcctgcgac   900
gacttcacgc acgcggcccc aacggctac ctggacctgt tcaccgacga ccagaactac   960
gccaagcagt ggcgctacac caacgccccc gacgctgacg cgcgggccgt ccaggtgatg   1020
ttctgggcgc acgaatgggc caaggagcag ggcaaggaga cgagatcgc gggcctgatg   1080
gacaaggcgt ccaagatggg cgactacctc cggtacgcga tgttcgacaa gtacttcaag   1140
aagatcggca actgcgtcgg cgccaccctc ctgcccgggtg ccaaggcaa ggacagcgcg    1200
cactacctgc tgtcctggta ctactcctgg ggcggctcgc tcgacacctc ctctgcgtgg   1260
gcgtggcgta tcggctccag ctcctcgcac cagggctacc agaacgtgct cgctgcctac   1320
gcgctctcgc aggtgcccga actgcagcct gactccccga ccggtgtcca ggactgggcc   1380
accagcttcg accgccagtt ggagttcctc cagtggctgc agtccgctga aggtggtatc   1440
```

```
gccggtggcg ccaccaacag ctggaaggga agctacgaca ccccgccgac cggcctgtcg      1500
cagttctacg gcatgtacta cgactggcag ccggtctgga acgacccgcc gtccaacaac      1560
tggttcggct tccaggtctg aacatggag cgcgtcgccc agctctacta cgtgaccggc       1620
gacgcccggg ccgaggccat cctcgacaag tgggtgccgt gggccatcca gcacaccgac      1680
gtggacgccg acaacggcgg ccagaacttc caggtcccct ccgacctgga gtggtcgggc      1740
cagcctgaca cctggaccgg cacctacacc ggcaacccga acctgcacgt ccaggtcgtc      1800
tcctacagcc aggacgtcgg tgtgaccgcc gctctggcca agaccctgat gtactacgcg      1860
aagcgttcgg gcgacaccac cgccctcgcc accgcggagg gtctgctgga cgccctgctg      1920
gcccaccggg acagcatcgg tatcgccacc cccgagcagc cgagctggga ccgtctggac      1980
gacccgtggg acggctccga gggcctgtac gtgccgccgg gctggtcggg caccatgccc      2040
aacggtgacc gcatcgagcc gggcgcgacc ttcctgtcca tccgctcgtt ctacaagaac      2100
gacccgctgt ggccgcaggt cgaggcacac ctgaacgacc gcagaacgt cccggcgccg       2160 atcgtggagc gccaccgctt ctgggctcag gtggaaatcg cgaccgcgtt cgcagcccac      2220
gacgaactgt tcggggccgg agctccctga                                       2250
```

```
<210> SEQ ID NO 17
<211> LENGTH: 511
<212> TYPE: PRT
<213> ORGANISM: Artificial Sequence
<220> FEATURE:
<223> OTHER INFORMATION: Polypeptide

<400> SEQUENCE: 17

Met Asp Leu Gln Val Asp Ile Gly Ser Thr Ser Gly Lys Ala Gly Ser
1               5                   10                  15

Val Val Ser Val Pro Ile Thr Phe Thr Asn Val Pro Lys Ser Gly Ile
            20                  25                  30

Tyr Ala Leu Ser Phe Arg Thr Asn Phe Asp Pro Gln Lys Val Thr Val
        35                  40                  45

Ala Ser Ile Asp Ala Gly Ser Leu Ile Glu Asn Ala Ser Asp Phe Thr
    50                  55                  60

Thr Tyr Tyr Asn Asn Glu Asn Gly Phe Ala Ser Met Thr Phe Glu Ala
65                  70                  75                  80

Pro Val Asp Arg Ala Arg Ile Ile Asp Ser Asp Gly Val Phe Ala Thr
                85                  90                  95

Ile Asn Phe Lys Val Ser Asp Ser Ala Lys Val Gly Glu Leu Tyr Asn
            100                 105                 110

Ile Thr Thr Asn Ser Ala Tyr Thr Ser Phe Tyr Ser Gly Thr Asp
        115                 120                 125

Glu Ile Lys Asn Val Val Tyr Asn Asp Gly Lys Ile Glu Val Ile Ala
    130                 135                 140

Ser Val Pro Thr Asn Thr Pro Thr Asn Pro Ala Asn Thr Pro Val
145                 150                 155                 160

Ser Gly Asn Leu Lys Val Glu Phe Tyr Asn Ser Asn Pro Ser Asp Thr
                165                 170                 175

Thr Asn Ser Ile Asn Pro Gln Phe Lys Val Thr Asn Thr Gly Ser Ser
            180                 185                 190

Ala Ile Asp Leu Ser Lys Leu Thr Leu Arg Tyr Tyr Tyr Thr Val Asp
        195                 200                 205

Gly Gln Lys Asp Gln Thr Phe Trp Cys Asp His Ala Ala Ile Ile Gly
    210                 215                 220
```

```
Ser Asn Gly Ser Tyr Asn Gly Ile Thr Ser Asn Val Lys Gly Thr Phe
225                 230                 235                 240

Val Lys Met Ser Ser Thr Asn Asn Ala Asp Thr Tyr Leu Glu Ile
            245                 250                 255

Ser Phe Thr Gly Gly Thr Leu Glu Pro Gly Ala His Val Gln Ile Gln
                260                 265                 270

Gly Arg Phe Ala Lys Asn Asp Trp Ser Asn Tyr Thr Gln Ser Asn Asp
            275                 280                 285

Tyr Ser Phe Lys Ser Ala Ser Gln Phe Val Glu Trp Asp Gln Val Thr
        290                 295                 300

Ala Tyr Leu Asn Gly Val Leu Val Trp Gly Lys Glu Pro Gly Gly Ser
305                 310                 315                 320

Val Val Pro Ser Thr Gln Pro Val Thr Thr Pro Ala Thr Thr Lys
                325                 330                 335

Pro Pro Ala Thr Thr Ile Pro Pro Ser Glu Asp Pro Ala Gly Gly Leu
                340                 345                 350

Ser Ala Val Gln Pro Asn Val Ser Leu Gly Glu Val Leu Asp Val Ser
            355                 360                 365

Ala Asn Arg Thr Ala Ala Asp Gly Thr Val Glu Trp Leu Ile Pro Thr
370                 375                 380

Val Thr Ala Ala Pro Gly Gln Thr Val Thr Met Pro Val Val Lys
385                 390                 395                 400

Ser Ser Ser Leu Ala Val Ala Gly Ala Gln Phe Lys Ile Gln Ala Ala
            405                 410                 415

Thr Gly Val Ser Tyr Ser Ser Lys Thr Asp Gly Asp Ala Tyr Gly Ser
            420                 425                 430

Gly Ile Val Tyr Asn Asn Ser Lys Tyr Ala Phe Gly Gln Gly Ala Gly
            435                 440                 445

Arg Gly Ile Val Ala Ala Asp Asp Ser Val Val Leu Thr Leu Ala Tyr
    450                 455                 460

Thr Val Pro Ala Asp Cys Ala Glu Gly Thr Tyr Asp Val Lys Trp Ser
465                 470                 475                 480

Asp Ala Phe Val Ser Asp Thr Asp Gly Gln Asn Ile Thr Ser Lys Val
                485                 490                 495

Thr Leu Thr Asp Gly Ala Ile Ile Val His His His His His
                500                 505                 510

<210> SEQ ID NO 18
<211> LENGTH: 1536
<212> TYPE: DNA
<213> ORGANISM: Artificial Sequence
<220> FEATURE:
<223> OTHER INFORMATION: Polynucleotide

<400> SEQUENCE: 18
atggatttac aggttgacat tggaagtact agtggaaaag caggtagtgt tgttagtgta      60
cctataacat ttactaatgt acctaaatca ggtatctatg ctctaagttt tagaacaaat     120
ttcgacccac aaaaggtaac tgtagcaagt atagatgctg gctcactgat tgaaaatgct     180
tctgatttta ctactatta taataatgaa atggttttg catcaatgac gtttgaagcc      240
ccagttgata gagctagaat catagatagt gatggtgtat ttgcaaccat taactttaaa     300
gttagtgata gtgccaaagt aggtgaactt tacaatatta ctactaatag tgcatatact     360
tcattctatt attctggaac tgatgaaatc aaaaatgttg tttacaatga tggaaaaatt     420
```

```
gaggtaattg catcggtacc gacaaacaca ccgacaaaca caccggcaaa tacaccggta    480
tcaggcaatt tgaaggttga attctacaac agcaatcctt cagatactac taactcaatc    540
aatcctcagt tcaaggttac taataccgga agcagtgcaa ttgatttgtc caaactcaca    600
ttgagatatt attatacagt agacggacag aaagatcaga ccttctggtg tgaccatgct    660
gcaataatcg gcagtaacgg cagctacaac ggaattactt caaatgtaaa aggaacattt    720
gtaaaaatga gttcctcaac aaataacgca gacacctacc ttgaaataag ctttacaggc    780
ggaactcttg aaccgggtgc acatgttcag atacaaggta gatttgcaaa gaatgactgg    840
agtaactata cacagtcaaa tgactactca ttcaagtctg cttcacagtt tgttgaatgg    900
gatcaggtaa cagcatactt gaacggtgtt cttgtatggg gtaaagaacc cggtggcagt    960
gtagtaccat caacacagcc tgtaacaaca ccacctgcaa caacaaaacc acctgcaaca   1020
acaataccgc cgtcagagga tcccgccggt ggtttatccg ctgtgcagcc taatgttagt   1080
ttaggcgaag tactgatgt ttctgctaac agaaccgctg ctgacggaac agttgaatgg    1140
cttatcccaa cagtaactgc agctccaggc cagacggtca ctatgcccgt agtagtcaag   1200
agttcaagtc ttgcagttgc tggtgcgcag ttcaagatcc aggcggcgac aggcgtaagt   1260
tattcgtcca agacggacgg tgacgcttac ggttcaggca ttgtgtacaa taatagtaag   1320
tatgcttttg acagggtgc aggtagagga atagttgcag ctgatgattc ggttgtgctt    1380
actcttgcat atacagttcc cgctgattgt gctgaaggta catatgatgt caagtggtct   1440
gatgcgtttg taagtgatac agacggacag aatatcacaa gtaaggttac tcttactgat   1500
ggcgctatca ttgttcacca tcaccatcac cattaa                             1536
```

<210> SEQ ID NO 19
<211> LENGTH: 500
<212> TYPE: PRT
<213> ORGANISM: Artificial Sequence
<220> FEATURE:
<223> OTHER INFORMATION: Polypeptide

<400> SEQUENCE: 19

```
Met Asp Leu Gln Val Asp Ile Gly Ser Thr Ser Gly Lys Ala Gly Ser
1               5                   10                  15

Val Val Ser Val Pro Ile Thr Phe Thr Asn Val Pro Lys Ser Gly Ile
            20                  25                  30

Tyr Ala Leu Ser Phe Arg Thr Asn Phe Asp Pro Gln Lys Val Thr Val
        35                  40                  45

Ala Ser Ile Asp Ala Gly Ser Leu Ile Glu Asn Ala Ser Asp Phe Thr
    50                  55                  60

Thr Tyr Tyr Asn Asn Glu Asn Gly Phe Ala Ser Met Thr Phe Glu Ala
65                  70                  75                  80

Pro Val Asp Arg Ala Arg Ile Ile Asp Ser Asp Gly Val Phe Ala Thr
                85                  90                  95

Ile Asn Phe Lys Val Ser Asp Ser Ala Lys Val Gly Glu Leu Tyr Asn
            100                 105                 110

Ile Thr Thr Asn Ser Ala Tyr Thr Ser Phe Tyr Tyr Ser Gly Thr Asp
        115                 120                 125

Glu Ile Lys Asn Val Val Tyr Asn Asp Gly Lys Ile Glu Val Ile Ala
    130                 135                 140

Ser Val Pro Thr Asn Thr Pro Thr Asn Thr Pro Ala Asn Thr Pro Val
145                 150                 155                 160

Ser Gly Asn Leu Lys Val Glu Phe Tyr Asn Ser Asn Pro Ser Asp Thr
```

```
                    165                 170                 175
Thr Asn Ser Ile Asn Pro Gln Phe Lys Val Thr Asn Thr Gly Ser Ser
                180                 185                 190

Ala Ile Asp Leu Ser Lys Leu Thr Leu Arg Tyr Tyr Thr Val Asp
            195                 200                 205

Gly Gln Lys Asp Gln Thr Phe Trp Cys Asp His Ala Ala Ile Ile Gly
        210                 215                 220

Ser Asn Gly Ser Tyr Asn Gly Ile Thr Ser Asn Val Lys Gly Thr Phe
225                 230                 235                 240

Val Lys Met Ser Ser Ser Thr Asn Asn Ala Asp Thr Tyr Leu Glu Ile
                245                 250                 255

Ser Phe Thr Gly Gly Thr Leu Glu Pro Gly Ala His Val Gln Ile Gln
                260                 265                 270

Gly Arg Phe Ala Lys Asn Asp Trp Ser Asn Tyr Thr Gln Ser Asn Asp
            275                 280                 285

Tyr Ser Phe Lys Ser Ala Ser Gln Phe Val Glu Trp Asp Gln Val Thr
        290                 295                 300

Ala Tyr Leu Asn Gly Val Leu Val Trp Gly Lys Glu Pro Gly Gly Ser
305                 310                 315                 320

Val Val Pro Ser Thr Gln Pro Val Thr Thr Pro Ala Thr Thr Lys
                325                 330                 335

Pro Pro Ala Thr Thr Ile Pro Pro Ser Asp Asp Pro Asn Ala Ile Lys
            340                 345                 350

Ile Lys Val Asp Thr Val Asn Ala Lys Pro Gly Asp Thr Val Asn Ile
        355                 360                 365

Pro Val Arg Phe Ser Gly Ile Pro Ser Lys Gly Ile Ala Asn Cys Asp
370                 375                 380

Phe Val Tyr Ser Tyr Asp Pro Asn Val Leu Glu Ile Ile Glu Ile Lys
385                 390                 395                 400

Pro Gly Glu Leu Ile Val Asp Pro Asn Pro Asp Lys Ser Phe Asp Thr
                405                 410                 415

Ala Val Tyr Pro Asp Arg Lys Ile Ile Val Phe Leu Phe Ala Glu Asp
            420                 425                 430

Ser Gly Thr Gly Ala Tyr Ala Ile Thr Lys Asp Gly Val Phe Ala Thr
        435                 440                 445

Ile Val Ala Lys Val Lys Ser Gly Ala Pro Asn Gly Leu Ser Val Ile
        450                 455                 460

Lys Phe Val Glu Val Gly Gly Phe Ala Asn Asn Asp Leu Val Glu Gln
465                 470                 475                 480

Arg Thr Gln Phe Phe Asp Gly Gly Val Asn Val Gly Asp Ile His His
                485                 490                 495

His His His His
        500

<210> SEQ ID NO 20
<211> LENGTH: 1503
<212> TYPE: DNA
<213> ORGANISM: Artificial Sequence
<220> FEATURE:
<223> OTHER INFORMATION: Polynucleotide

<400> SEQUENCE: 20
atggatttac aggttgacat tggaagtact agtggaaaag caggtagtgt tgttagtgta      60
cctataacat ttactaatgt acctaaatca ggtatctatg ctctaagttt tagaacaaat     120
```

```
ttcgacccac aaaaggtaac tgtagcaagt atagatgctg gctcactgat tgaaaatgct    180
tctgatttta ctacttatta taataatgaa aatggttttg catcaatgac gtttgaagcc    240
ccagttgata gagctagaat catagatagt gatggtgtat ttgcaaccat taactttaaa    300
gttagtgata gtgccaaagt aggtgaactt tacaatatta ctactaatag tgcatatact    360
tcattctatt attctggaac tgatgaaatc aaaaatgttg tttacaatga tggaaaaatt    420
gaggtaattg catcggtacc gacaaacaca ccgacaaaca caccggcaaa tacaccggta    480
tcaggcaatt tgaaggttga attctacaac agcaatcctt cagatactac taactcaatc    540
aatcctcagt tcaaggttac taataccgga agcagtgcaa ttgatttgtc caaactcaca    600
ttgagatatt attatacagt agacggacag aaagatcaga ccttctggtg tgaccatgct    660
gcaataatcg gcagtaacgg cagctacaac ggaattactt caaatgtaaa aggaacattt    720
gtaaaaatga gttcctcaac aaataacgca gacacctacc ttgaaataag ctttacaggc    780
ggaactcttg aaccgggtgc acatgttcag atacaaggta gatttgcaaa gaatgactgg    840
agtaactata cacagtcaaa tgactactca ttcaagtctg cttcacagtt tgttgaatgg    900
gatcaggtaa cagcatactt gaacggtgtt cttgtatggg gtaaagaacc cggtggcagt    960
gtagtaccat caacacagcc tgtaacaaca ccacctgcaa caacaaaacc acctgcaaca   1020
acaataccgc cgtcagatga tccgaatgca ataaagatta aggtggacac agtaaatgca   1080
aaaccgggag acacagtaaa tatacctgta agattcagtg gtataccatc caagggaata   1140
gcaaactgtg actttgtata cagctatgac ccgaatgtac ttgagataat agagataaaa   1200
ccgggagaat tgatagttga cccgaatcct gacaagagct tgatactgc agtatatcct    1260
gacagaaaga taatagtatt cctgtttgca gaagacagcg gaacaggagc gtatgcaata   1320
actaaagacg gagtatttgc tacgatagta gcgaaagtaa aatccggagc acctaacgga   1380
ctcagtgtaa tcaaatttgt agaagtaggc ggatttgcga acaatgacct tgtagaacag   1440
aggacacagt tctttgacgg tggagtaaat gttggagata taccatcatca ccatcaccat   1500
taa                                                                1503
```

<210> SEQ ID NO 21
<211> LENGTH: 518
<212> TYPE: PRT
<213> ORGANISM: Artificial Sequence
<220> FEATURE:
<223> OTHER INFORMATION: Polupeptide

<400> SEQUENCE: 21

```
Met Ala Gly Lys Ser Ser Pro Gly Asn Lys Met Lys Ile Gln Ile Gly
1               5                   10                  15

Asp Val Lys Ala Asn Gln Gly Asp Thr Val Ile Val Pro Ile Thr Phe
            20                  25                  30

Asn Glu Val Pro Val Met Gly Val Asn Asn Cys Asn Phe Thr Leu Ala
        35                  40                  45

Tyr Asp Lys Asn Ile Met Glu Phe Ile Ser Ala Asp Ala Gly Asp Ile
    50                  55                  60

Val Thr Leu Pro Met Ala Asn Tyr Ser Tyr Asn Met Pro Ser Asp Gly
65                  70                  75                  80

Leu Val Lys Phe Leu Tyr Asn Asp Gln Ala Gln Gly Ala Met Ser Ile
                85                  90                  95

Lys Glu Asp Gly Thr Phe Ala Asn Val Lys Phe Lys Ile Lys Gln Ser
            100                 105                 110
```

-continued

```
Ala Ala Phe Gly Lys Tyr Ser Val Gly Ile Lys Ala Ile Gly Ser Ile
            115                 120                 125
Ser Ala Leu Ser Asn Ser Lys Leu Ile Pro Ile Glu Ser Ile Phe Lys
130                 135                 140
Asp Gly Ser Ile Thr Val Thr Lys Val Pro Thr Asn Thr Pro Thr Asn
145                 150                 155                 160
Thr Pro Ala Asn Thr Pro Val Ser Gly Asn Leu Lys Val Glu Phe Tyr
                165                 170                 175
Asn Ser Asn Pro Ser Asp Thr Thr Asn Ser Ile Asn Pro Gln Phe Lys
            180                 185                 190
Val Thr Asn Thr Gly Ser Ser Ala Ile Asp Leu Ser Lys Leu Thr Leu
        195                 200                 205
Arg Tyr Tyr Tyr Thr Val Asp Gly Gln Lys Asp Gln Thr Phe Trp Cys
    210                 215                 220
Asp His Ala Ala Ile Ile Gly Ser Asn Gly Ser Tyr Asn Gly Ile Thr
225                 230                 235                 240
Ser Asn Val Lys Gly Thr Phe Val Lys Met Ser Ser Ser Thr Asn Asn
                245                 250                 255
Ala Asp Thr Tyr Leu Glu Ile Ser Phe Thr Gly Gly Thr Leu Glu Pro
            260                 265                 270
Gly Ala His Val Gln Ile Gln Gly Arg Phe Ala Lys Asn Asp Trp Ser
        275                 280                 285
Asn Tyr Thr Gln Ser Asn Asp Tyr Ser Phe Lys Ser Ala Ser Gln Phe
    290                 295                 300
Val Glu Trp Asp Gln Val Thr Ala Tyr Leu Asn Gly Val Leu Val Trp
305                 310                 315                 320
Gly Lys Glu Pro Gly Gly Ser Val Val Pro Ser Thr Gln Pro Val Thr
                325                 330                 335
Thr Pro Pro Ala Thr Thr Lys Pro Pro Ala Thr Thr Ile Pro Pro Ser
            340                 345                 350
Glu Asp Pro Ala Gly Gly Leu Ser Ala Val Gln Pro Asn Val Ser Leu
        355                 360                 365
Gly Glu Val Leu Asp Val Ser Ala Asn Arg Thr Ala Ala Asp Gly Thr
    370                 375                 380
Val Glu Trp Leu Ile Pro Thr Val Thr Ala Ala Pro Gly Gln Thr Val
385                 390                 395                 400
Thr Met Pro Val Val Val Lys Ser Ser Ser Leu Ala Val Ala Gly Ala
                405                 410                 415
Gln Phe Lys Ile Gln Ala Ala Thr Gly Val Ser Tyr Ser Ser Lys Thr
            420                 425                 430
Asp Gly Asp Ala Tyr Gly Ser Gly Ile Val Tyr Asn Asn Ser Lys Tyr
        435                 440                 445
Ala Phe Gly Gln Gly Ala Gly Arg Gly Ile Val Ala Ala Asp Asp Ser
    450                 455                 460
Val Val Leu Thr Leu Ala Tyr Thr Val Pro Ala Asp Cys Ala Glu Gly
465                 470                 475                 480
Thr Tyr Asp Val Lys Trp Ser Asp Ala Phe Val Ser Asp Thr Asp Gly
                485                 490                 495
Gln Asn Ile Thr Ser Lys Val Thr Leu Thr Asp Gly Ala Ile Ile Val
            500                 505                 510
His His His His His His
        515
```

<210> SEQ ID NO 22
<211> LENGTH: 1557
<212> TYPE: DNA
<213> ORGANISM: Artificial Sequence
<220> FEATURE:
<223> OTHER INFORMATION: Polynucleotide

<400> SEQUENCE: 22

```
atggcgggga aaagttcacc aggaaataaa atgaaaattc aaattggtga tgtaaaagct      60
aatcagggag atacagttat agtacctata actttcaatg aagttcctgt aatgggtgtt     120
aataactgta atttcacttt agcttatgac aaaaatatta tggaatttat ctctgctgat     180
gcaggtgata ttgtaacatt gccaatggct aactatagct acaatatgcc atctgatggg     240
ctagtaaaat tttttatataa tgatcaagct caaggtgcaa tgtcaataaa agaagatggt     300
acttttgcta atgttaaatt taaaattaag cagagtgccg catttgggaa atattcagta     360
ggcatcaaag caattggttc aatttccgct ttaagcaata gtaagttaat acctattgaa     420
tcaatattta agatggaag cattactgta actaaggtac cgacaaacac accgacaaac     480
acaccggcaa ataccggt atcaggcaat ttgaaggttg aattctacaa cagcaatcct     540
tcagatacta ctaactcaat caatcctcag ttcaaggtta ctaataccgg aagcagtgca     600
attgatttgt ccaaactcac attgagatat tattatacag tagacggaca gaaagatcag     660
accttctggt gtgaccatgc tgcaataatc ggcagtaacg gcagctacaa cggaattact     720
tcaaatgtaa aaggaacatt tgtaaaaatg agttcctcaa caaataacgc agacacctac     780
cttgaaataa gctttacagg cggaactctt gaaccgggtg cacatgttca gatacaaggt     840
agatttgcaa agaatgactg gagtaactat acacagtcaa atgactactc attcaagtct     900
gcttcacagt ttgttgaatg ggatcaggta acagcatact tgaacggtgt tcttgtatgg     960
ggtaaagaac ccggtggcag tgtagtacca tcaacacagc ctgtaacaac accacctgca    1020
acaacaaaac cacctgcaac aacaataccg ccgtcagagg atcccgccgg tggtttatcc    1080
gctgtgcagc ctaatgttag tttaggcgaa gtactggatg tttctgctaa cagaaccgct    1140
gctgacggaa cagttgaatg gcttatccca acagtaactg cagctccagg ccagacggtc    1200
actatgcccg tagtagtcaa gagttcaagt cttgcagttg ctggtgcgca gttcaagatc    1260
caggcggcga caggcgtaag ttattcgtcc aagacggacg tgacgctta cggttcaggc    1320
attgtgtaca ataatagtaa gtatgctttt ggacagggtg caggtagagg aatagttgca    1380
gctgatgatt cggttgtgct tactcttgca tatacagttc ccgctgattg tgctgaaggt    1440
acatatgatg tcaagtggtc tgatgcgttt gtaagtgata cagacggaca gaatatcaca    1500
agtaaggtta ctcttactga tggcgctatc attgttcacc atcaccatca ccattaa       1557
```

<210> SEQ ID NO 23
<211> LENGTH: 659
<212> TYPE: PRT
<213> ORGANISM: Artificial Sequence
<220> FEATURE:
<223> OTHER INFORMATION: Polypeptide

<400> SEQUENCE: 23

Met Asp Leu Gln Val Asp Ile Gly Ser Thr Ser Gly Lys Ala Gly Ser
1               5                   10                  15

Val Val Ser Val Pro Ile Thr Phe Thr Asn Val Pro Lys Ser Gly Ile
            20                  25                  30

Tyr Ala Leu Ser Phe Arg Thr Asn Phe Asp Pro Gln Lys Val Thr Val
        35                  40                  45

```
Ala Ser Ile Asp Ala Gly Ser Leu Ile Glu Asn Ala Ser Asp Phe Thr
 50                  55                  60

Thr Tyr Tyr Asn Asn Glu Asn Gly Phe Ala Ser Met Thr Phe Glu Ala
 65                  70                  75                  80

Pro Val Asp Arg Ala Arg Ile Ile Asp Ser Asp Gly Val Phe Ala Thr
                 85                  90                  95

Ile Asn Phe Lys Val Ser Asp Ser Ala Lys Val Gly Glu Leu Tyr Asn
                100                 105                 110

Ile Thr Thr Asn Ser Ala Tyr Thr Ser Phe Tyr Tyr Ser Gly Thr Asp
            115                 120                 125

Glu Ile Lys Asn Val Val Tyr Asn Asp Gly Lys Ile Glu Val Ile Ala
        130                 135                 140

Ser Val Pro Thr Asn Thr Pro Thr Asn Thr Pro Ala Asn Thr Pro Val
145                 150                 155                 160

Ser Gly Asn Leu Lys Val Glu Phe Tyr Asn Ser Asn Pro Ser Asp Thr
                165                 170                 175

Thr Asn Ser Ile Asn Pro Gln Phe Lys Val Thr Asn Thr Gly Ser Ser
            180                 185                 190

Ala Ile Asp Leu Ser Lys Leu Thr Leu Arg Tyr Tyr Tyr Thr Val Asp
        195                 200                 205

Gly Gln Lys Asp Gln Thr Phe Trp Cys Asp His Ala Ala Ile Ile Gly
    210                 215                 220

Ser Asn Gly Ser Tyr Asn Gly Ile Thr Ser Asn Val Lys Gly Thr Phe
225                 230                 235                 240

Val Lys Met Ser Ser Thr Asn Asn Ala Asp Thr Tyr Leu Glu Ile
                245                 250                 255

Ser Phe Thr Gly Gly Thr Leu Glu Pro Gly Ala His Val Gln Ile Gln
                260                 265                 270

Gly Arg Phe Ala Lys Asn Asp Trp Ser Asn Tyr Thr Gln Ser Asn Asp
            275                 280                 285

Tyr Ser Phe Lys Ser Ala Ser Gln Phe Val Glu Trp Asp Gln Val Thr
        290                 295                 300

Ala Tyr Leu Asn Gly Val Leu Val Trp Gly Lys Glu Pro Gly Gly Ser
305                 310                 315                 320

Val Val Pro Ser Thr Gln Pro Val Thr Thr Pro Ala Thr Thr Lys
                325                 330                 335

Pro Pro Ala Thr Thr Ile Pro Pro Ser Asp Asp Pro Asn Ala Ile Lys
            340                 345                 350

Ile Lys Val Asp Thr Val Asn Ala Lys Pro Gly Asp Thr Val Asn Ile
        355                 360                 365

Pro Val Arg Phe Ser Gly Ile Pro Ser Lys Gly Ile Ala Asn Cys Asp
    370                 375                 380

Phe Val Tyr Ser Tyr Asp Pro Asn Val Leu Glu Ile Ile Glu Ile Lys
385                 390                 395                 400

Pro Gly Glu Leu Ile Val Asp Pro Asn Pro Asp Lys Ser Phe Asp Thr
                405                 410                 415

Ala Val Tyr Pro Asp Arg Lys Ile Ile Val Phe Leu Phe Ala Glu Asp
            420                 425                 430

Ser Gly Thr Gly Ala Tyr Ala Ile Thr Lys Asp Gly Val Phe Ala Thr
        435                 440                 445

Ile Val Ala Lys Val Lys Ser Gly Ala Pro Asn Gly Leu Ser Val Ile
    450                 455                 460
```

```
Lys Phe Val Glu Val Gly Gly Phe Ala Asn Asn Asp Leu Val Glu Gln
465                 470                 475                 480

Arg Thr Gln Phe Phe Asp Gly Val Asn Val Gly Asp Ile Gly Ser
            485                 490                 495

Ala Gly Gly Leu Ser Ala Val Gln Pro Asn Val Ser Leu Gly Glu Val
                500                 505                 510

Leu Asp Val Ser Ala Asn Arg Thr Ala Ala Asp Gly Thr Val Glu Trp
            515                 520                 525

Leu Ile Pro Thr Val Thr Ala Pro Gly Gln Thr Val Thr Met Pro
    530                 535                 540

Val Val Val Lys Ser Ser Leu Ala Val Ala Gly Ala Gln Phe Lys
545                 550                 555                 560

Ile Gln Ala Ala Thr Gly Val Ser Tyr Ser Ser Lys Thr Asp Gly Asp
                565                 570                 575

Ala Tyr Gly Ser Gly Ile Val Tyr Asn Asn Ser Lys Tyr Ala Phe Gly
                580                 585                 590

Gln Gly Ala Gly Arg Gly Ile Val Ala Ala Asp Ser Val Val Leu
            595                 600                 605

Thr Leu Ala Tyr Thr Val Pro Ala Asp Cys Ala Glu Gly Thr Tyr Asp
610                 615                 620

Val Lys Trp Ser Asp Ala Phe Val Ser Asp Thr Asp Gly Gln Asn Ile
625                 630                 635                 640

Thr Ser Lys Val Thr Leu Thr Asp Gly Ala Ile Ile Val His His His
                645                 650                 655

His His His

<210> SEQ ID NO 24
<211> LENGTH: 1980
<212> TYPE: DNA
<213> ORGANISM: Artificial Sequence
<220> FEATURE:
<223> OTHER INFORMATION: Polynucleotide

<400> SEQUENCE: 24
atggatttac aggttgacat tggaagtact agtggaaaag caggtagtgt tgttagtgta      60
cctataacat ttactaatgt acctaaatca ggtatctatg ctctaagttt tagaacaaat     120
ttcgacccac aaaaggtaac tgtagcaagt atagatgctg gctcactgat tgaaaatgct     180
tctgatttta ctacttatta taataatgaa atggttttg catcaatgac gtttgaagcc     240
ccagttgata gagctagaat catagatagt gatggtgtat ttgcaaccat taactttaaa     300
gttagtgata gtgccaaagt aggtgaactt acaatatta ctactaatag tgcatatact     360
tcattctatt attctggaac tgatgaaatc aaaaatgttg tttacaatga tggaaaaatt     420
gaggtaattg catcggtacc gacaaacaca ccgacaaaca caccggcaaa tacaccggta     480
tcaggcaatt tgaaggttga attctacaac agcaatcctt cagatactac taactcaatc     540
aatcctcagt tcaaggttac taataccgga agcagtgcaa ttgatttgtc caaactcaca     600
ttgagatatt attatacagt agacggacag aaagatcaga ccttctggtg tgaccatgct     660
gcaataatcg gcagtaacgg cagctacaac ggaattactt caaatgtaaa aggaacattt     720
gtaaaaatga gttcctcaac aaataacgca gacacctacc ttgaaataag ctttacaggc     780
ggaactcttg aaccgggtgc acatgttcag atacaaggta gatttgcaaa gaatgactgg     840
agtaactata cacagtcaaa tgactactca ttcaagtctg cttcacagtt tgttgaatgg     900
gatcaggtaa cagcatactt gaacggtgtt cttgtatggg gtaaagaacc cggtggcagt     960
```

```
gtagtaccat caacacagcc tgtaacaaca ccacctgcaa caacaaaacc acctgcaaca    1020
acaataccgc cgtcagatga tccgaatgca ataaagatta aggtggacac agtaaatgca    1080
aaaccgggag acacagtaaa tatacctgta agattcagtg gtataccatc caagggaata    1140
gcaaactgtg actttgtata cagctatgac ccgaatgtac ttgagataat agagataaaa    1200
ccgggagaat tgatagttga cccgaatcct gacaagagct tgatactgc agtatatcct     1260 gacagaaaga taatagtatt cctgtttgca gaagacagcg gaacaggagc gtatgcaata    1320
actaaagacg gagtatttgc tacgatagta gcgaaagtaa atccggagc acctaacgga    1380 ctcagtgtaa tcaaatttgt agaagtaggc ggatttgcga caatgaccct tgtagaacag    1440
aggacacagt tctttgacgg tggagtaaat gttggagata taggatccgc cggtggttta    1500
tccgctgtgc agcctaatgt tagtttaggc gaagtactgg atgtttctgc taacagaacc    1560
gctgctgacg gaacagttga atggcttatc ccaacagtaa ctgcagctcc aggccagacg    1620
gtcactatgc ccgtagtagt caagagttca agtcttgcag ttgctggtgc gcagttcaag    1680
atccaggcgg cgacaggcgt aagttattcg tccaagacgg acggtgacgc ttacggttca    1740
ggcattgtgt acaataatag taagtatgct tttggacagg gtgcaggtag aggaatagtt    1800
gcagctgatg attcggttgt gcttactctt gcatatacag ttcccgctga ttgtgctgaa    1860
ggtacatatg atgtcaagtg gtctgatgcg tttgtaagtg atacagacgg acagaatatc    1920
acaagtaagg ttactcttac tgatggcgct atcattgttc accatcacca tcaccattaa    1980

<210> SEQ ID NO 25
<211> LENGTH: 841
<212> TYPE: PRT
<213> ORGANISM: Artificial Sequence
<220> FEATURE:
<223> OTHER INFORMATION: Polypeptide

<400> SEQUENCE: 25

Met Ala Gly Lys Ser Ser Pro Gly Asn Lys Met Lys Ile Gln Ile Gly
1               5                   10                  15

Asp Val Lys Ala Asn Gln Gly Asp Thr Val Ile Val Pro Ile Thr Phe
            20                  25                  30

Asn Glu Val Pro Val Met Gly Val Asn Asn Cys Asn Phe Thr Leu Ala
        35                  40                  45

Tyr Asp Lys Asn Ile Met Glu Phe Ile Ser Ala Asp Ala Gly Asp Ile
    50                  55                  60

Val Thr Leu Pro Met Ala Asn Tyr Ser Tyr Asn Met Pro Ser Asp Gly
65                  70                  75                  80

Leu Val Lys Phe Leu Tyr Asn Asp Gln Ala Gln Gly Ala Met Ser Ile
                85                  90                  95

Lys Glu Asp Gly Thr Phe Ala Asn Val Lys Phe Lys Ile Lys Gln Ser
            100                 105                 110

Ala Ala Phe Gly Lys Tyr Ser Val Gly Ile Lys Ala Ile Gly Ser Ile
        115                 120                 125

Ser Ala Leu Ser Asn Ser Lys Leu Ile Pro Ile Glu Ser Ile Phe Lys
    130                 135                 140

Asp Gly Ser Ile Thr Val Thr Lys Val Pro Thr Asn Thr Pro Thr Asn
145                 150                 155                 160

Thr Pro Ala Asn Thr Pro Val Ser Gly Asn Leu Lys Val Glu Phe Tyr
                165                 170                 175

Asn Ser Asn Pro Ser Asp Thr Thr Asn Ser Ile Asn Pro Gln Phe Lys
```

```
            180                 185                 190
Val Thr Asn Thr Gly Ser Ser Ala Ile Asp Leu Ser Lys Leu Thr Leu
            195                 200                 205
Arg Tyr Tyr Tyr Thr Val Asp Gly Gln Lys Asp Gln Thr Phe Trp Cys
            210                 215                 220
Asp His Ala Ala Ile Ile Gly Ser Asn Gly Ser Tyr Asn Gly Ile Thr
225                 230                 235                 240
Ser Asn Val Lys Gly Thr Phe Val Lys Met Ser Ser Thr Asn Asn
                245                 250                 255
Ala Asp Thr Tyr Leu Glu Ile Ser Phe Thr Gly Gly Thr Leu Glu Pro
            260                 265                 270
Gly Ala His Val Gln Ile Gln Gly Arg Phe Ala Lys Asn Asp Trp Ser
            275                 280                 285
Asn Tyr Thr Gln Ser Asn Asp Tyr Ser Phe Lys Ser Ala Ser Gln Phe
            290                 295                 300
Val Glu Trp Asp Gln Val Thr Ala Tyr Leu Asn Gly Val Leu Val Trp
305                 310                 315                 320
Gly Lys Glu Pro Gly Ser Val Val Pro Ser Thr Gln Pro Val Thr
                325                 330                 335
Thr Pro Pro Ala Thr Thr Lys Pro Pro Ala Thr Thr Ile Pro Pro Ser
            340                 345                 350
Asp Asp Pro Asn Ala Ile Lys Ile Lys Val Asp Thr Val Asn Ala Lys
            355                 360                 365
Pro Gly Asp Thr Val Asn Ile Pro Val Arg Phe Ser Gly Ile Pro Ser
            370                 375                 380
Lys Gly Ile Ala Asn Cys Asp Phe Val Tyr Ser Tyr Asp Pro Asn Val
385                 390                 395                 400
Leu Glu Ile Ile Glu Ile Lys Pro Gly Glu Leu Ile Val Asp Pro Asn
                405                 410                 415
Pro Asp Lys Ser Phe Asp Thr Ala Val Tyr Pro Asp Arg Lys Ile Ile
            420                 425                 430
Val Phe Leu Phe Ala Glu Asp Ser Gly Thr Gly Ala Tyr Ala Ile Thr
            435                 440                 445
Lys Asp Gly Val Phe Ala Thr Ile Val Ala Lys Val Lys Ser Gly Ala
            450                 455                 460
Pro Asn Gly Leu Ser Val Ile Lys Phe Val Glu Val Gly Gly Phe Ala
465                 470                 475                 480
Asn Asn Asp Leu Val Glu Gln Arg Thr Gln Phe Phe Asp Gly Gly Val
                485                 490                 495
Asn Val Gly Asp Ile Gly Ser Ala Gly Gly Leu Ser Ala Val Gln Pro
            500                 505                 510
Asn Val Ser Leu Gly Glu Val Leu Asp Val Ser Ala Asn Arg Thr Ala
            515                 520                 525
Ala Asp Gly Thr Val Glu Trp Leu Ile Pro Thr Val Thr Ala Ala Pro
            530                 535                 540
Gly Gln Thr Val Thr Met Pro Val Val Lys Ser Ser Ser Leu Ala
545                 550                 555                 560
Val Ala Gly Ala Gln Phe Lys Ile Gln Ala Ala Thr Gly Val Ser Tyr
                565                 570                 575
Ser Ser Lys Thr Asp Gly Asp Ala Tyr Gly Ser Gly Ile Val Tyr Asn
            580                 585                 590
Asn Ser Lys Tyr Ala Phe Gly Gln Gly Ala Gly Arg Gly Ile Val Ala
            595                 600                 605
```

```
Ala Asp Asp Ser Val Val Leu Thr Leu Ala Tyr Thr Val Pro Ala Asp
        610                 615                 620

Cys Ala Glu Gly Thr Tyr Asp Val Lys Trp Ser Asp Ala Phe Val Ser
625                 630                 635                 640

Asp Thr Asp Gly Gln Asn Ile Thr Ser Lys Val Thr Leu Thr Asp Gly
                645                 650                 655

Ala Ile Ile Val Ala Ser Ala Pro Thr Ser Ser Ile Glu Ile Val Leu
                660                 665                 670

Asp Lys Thr Thr Ala Ser Val Gly Glu Ile Val Thr Ala Ser Ile Asn
        675                 680                 685

Ile Lys Asn Ile Thr Asn Phe Ser Gly Cys Gln Leu Asn Met Lys Tyr
    690                 695                 700

Asp Pro Ala Val Leu Gln Pro Val Thr Ser Ser Gly Val Ala Tyr Thr
705                 710                 715                 720

Lys Ser Thr Met Pro Gly Ala Gly Thr Ile Leu Asn Ser Asp Phe Asn
                725                 730                 735

Leu Arg Gln Val Ala Asp Asn Asp Leu Glu Lys Gly Ile Leu Asn Phe
                740                 745                 750

Ser Lys Ala Tyr Val Ser Leu Asp Asp Tyr Arg Thr Ala Ala Ala Pro
        755                 760                 765

Glu Gln Thr Gly Thr Val Ala Val Val Lys Phe Lys Val Leu Lys Glu
    770                 775                 780

Glu Thr Ser Ser Ile Ser Phe Glu Asp Thr Thr Ser Val Pro Asn Ala
785                 790                 795                 800

Ile Asp Gly Thr Val Leu Phe Asp Trp Asn Gly Asp Arg Ile Gln Ser
                805                 810                 815

Gly Tyr Ser Val Ile Gln Pro Ala Val Ile Asn Leu Asp Met Ile Lys
        820                 825                 830

Ala Leu Glu His His His His His His
        835                 840

<210> SEQ ID NO 26
<211> LENGTH: 2526
<212> TYPE: DNA
<213> ORGANISM: Artificial Sequence
<220> FEATURE:
<223> OTHER INFORMATION: Polynucleotide

<400> SEQUENCE: 26
atggcgggga aaagttcacc aggaaataaa atgaaaattc aaattggtga tgtaaaagct      60
aatcagggag atacagttat agtacctata actttcaatg aagttcctgt aatgggtgtt     120
aataactgta atttcacttt agcttatgac aaaaatatta tggaatttat ctctgctgat     180
gcaggtgata ttgtaacatt gccaatggct aactatagct acaatatgcc atctgatggg     240
ctagtaaaat ttttatataa tgatcaagct caaggtgcaa tgtcaataaa agaagatggt     300
acttttgcta atgttaaatt taaaattaag cagagtgccg catttgggaa atattcagta     360
ggcatcaaag caattggttc aatttccgct ttaagcaata gtaagttaat acctattgaa     420
tcaatattta aagatggaag cattactgta actaaggtac cgacaaacac accgacaaac     480
acaccggcaa atacaccggt atcaggcaat ttgaaggttg aattctacaa cagcaatcct     540
tcagatacta ctaactcaat caatcctcag ttcaaggtta ctaataccgg aagcagtgca     600
attgatttgt ccaaactcac attgagatat tattatacag tagacggaca gaaagatcag     660
accttctggt gtgaccatgc tgcaataatc ggcagtaacg gcagctacaa cggaattact     720
```

-continued

```
tcaaatgtaa aaggaacatt tgtaaaaatg agttcctcaa caaataacgc agacacctac      780
cttgaaataa gctttacagg cggaactctt gaaccgggtg cacatgttca gatacaaggt      840
agatttgcaa agaatgactg gagtaactat acacagtcaa atgactactc attcaagtct      900
gcttcacagt ttgttgaatg ggatcaggta acagcatact tgaacggtgt tcttgtatgg      960
ggtaaagaac ccggtggcag tgtagtacca tcaacacagc ctgtaacaac accacctgca     1020
acaacaaaac cacctgcaac aacaataccg ccgtcagatg atccgaatgc aataaagatt     1080
aaggtggaca cagtaaatgc aaaaccggga gacacagtaa atatacctgt aagattcagt     1140
ggtataccat ccaagggaat agcaaactgt gactttgtat acagctatga cccgaatgta     1200
cttgagataa tagagataaa accgggagaa ttgatagttg acccgaatcc tgacaagagc     1260
tttgatactg cagtatatcc tgacagaaag ataatatgta tcctgtttgc agaagacagc     1320
ggaacaggag cgtatgcaat aactaaagac ggagtatttg ctacgatagt agcgaaagta     1380
aaatccggag cacctaacgg actcagtgta atcaaatttg tagaagtagg cggatttgcg     1440
aacaatgacc ttgtagaaca gaggacacag ttctttgacg gtggagtaaa tgttggagat     1500
ataggatccg ccggtggttt atccgctgtg cagcctaatg ttagtttagg cgaagtactg     1560
gatgtttctg ctaacagaac cgctgctgac ggaacagttg aatggcttat cccaacagta     1620
actgcagctc caggccagac ggtcactatg cccgtagtag tcaagagttc aagtcttgca     1680
gttgctggtg cgcagttcaa gatccaggcg gcgacaggcg taagttattc gtccaagacg     1740
gacggtgacg cttacggttc aggcattgtg tacaataata gtaagtatgc ttttggacag     1800
ggtgcaggta gaggaatagt tgcagctgat gattcggttg tgcttactct tgcatataca     1860
gttcccgctg attgtgctga aggtacatat gatgtcaagt ggtctgatgc gtttgtaagt     1920
gatacagacg gacagaatat cacaagtaag gttactctta ctgatggcgc tatcattgtt     1980
gctagcgctc caacatctag tatagaaatt gtactagata agactaccgc atcagtagga     2040
gaaatcgtta ccgcatcaat aaatattaaa aatatcacca acttttcagg ttgtcagtta     2100
aatatgaagt atgatccagc tgtattacaa ccagttacat catctggtgt tgcatataca     2160
aagtcaacta tgccaggggc tggaacaatt cttaatagtg actttaattt aagacaagtg     2220
gccgacaatg accttgaaaa gggtattttg aacttttcaa aggcgtatgt aagtcttgat     2280
gattatagaa cagctgcagc tcctgaacag acaggtacag ttgctgtagt aaaatttaaa     2340
gttttgaagg aagaaacttc ttcaatcagt tttgaagata caacatcagt tccaaatgca     2400
atagacggaa cagtttttatt tgattggaat ggggatagaa tacaatctgg atattctgtg     2460
atccaaccgg cagtaattaa cttagatatg attaaagcgc tcgagcacca ccaccaccac     2520
cactga                                                                2526
```

<210> SEQ ID NO 27
<211> LENGTH: 77
<212> TYPE: PRT
<213> ORGANISM: Artificial Sequence
<220> FEATURE:
<223> OTHER INFORMATION: Polypeptide

<400> SEQUENCE: 27

Thr Tyr Lys Val Pro Gly Thr Pro Ser Thr Lys Leu Tyr Gly Asp Val
1               5                   10                  15

Asn Asp Asp Gly Lys Val Asn Ser Thr Asp Ala Val Ala Leu Lys Arg
            20                  25                  30

```
Tyr Val Leu Arg Ser Gly Ile Ser Ile Asn Thr Asp Asn Ala Asp Leu
             35                  40                  45

Asn Glu Asp Gly Arg Val Asn Ser Thr Asp Leu Gly Ile Leu Lys Arg
 50                  55                  60

Tyr Ile Leu Lys Glu Ile Asp Thr Leu Pro Tyr Lys Asn
 65                  70                  75

<210> SEQ ID NO 28
<211> LENGTH: 234
<212> TYPE: DNA
<213> ORGANISM: Artificial Sequence
<220> FEATURE:
<223> OTHER INFORMATION: Polynucleotide

<400> SEQUENCE: 28
acatataaag tacctggtac tccttctact aaattatacg gcgacgtcaa tgatgacgga      60
aaagttaact caactgacgc tgtagcattg aagagatatg ttttgagatc aggtataagc     120
atcaacactg acaatgccga tttgaatgaa gacggcagag ttaattcaac tgacttagga     180
attttgaaga gatatattct caaagaaata gatacattgc cgtacaagaa ctaa           234

<210> SEQ ID NO 29
<211> LENGTH: 91
<212> TYPE: PRT
<213> ORGANISM: Artificial Sequence
<220> FEATURE:
<223> OTHER INFORMATION: Polypeptide

<400> SEQUENCE: 29

Thr Ala Thr Thr Thr Pro Thr Thr Thr Pro Thr Thr Thr Pro Thr Pro
  1               5                  10                  15

Lys Phe Ile Tyr Gly Asp Val Asp Gly Asn Gly Ser Val Arg Ile Asn
             20                  25                  30

Asp Ala Val Leu Ile Arg Asp Tyr Val Leu Gly Lys Ile Asn Glu Phe
             35                  40                  45

Pro Tyr Glu Tyr Gly Met Leu Ala Ala Asp Val Asp Gly Asn Gly Ser
 50                  55                  60

Ile Lys Ile Asn Asp Ala Val Leu Val Arg Asp Tyr Val Leu Gly Lys
 65                  70                  75                  80

Ile Phe Leu Phe Pro Val Glu Glu Lys Glu Glu
             85                  90

<210> SEQ ID NO 30
<211> LENGTH: 276
<212> TYPE: DNA
<213> ORGANISM: Artificial Sequence
<220> FEATURE:
<223> OTHER INFORMATION: Polynucleotide

<400> SEQUENCE: 30
acagcaacta caaaccaac tacaacacca actacaacac caacgcctaa atttatatat      60
ggtgatgttg atggtaatgg aagtgtaaga attaatgatg ctgtcctaat aagagactat    120
gtattaggaa aaatcaatga attcccatat gaatatggta tgcttgcagc agatgttgat    180
ggtaatggaa gtataaaaat taatgatgct gttctagtaa gagactacgt gttaggaaag    240 atattttat tccctgttga agagaaagaa gaataa                              276

<210> SEQ ID NO 31
<211> LENGTH: 89
<212> TYPE: PRT
```

```
<213> ORGANISM: Artificial Sequence
<220> FEATURE:
<223> OTHER INFORMATION: Polypeptide

<400> SEQUENCE: 31

Ala Pro Ser Pro Gly Thr Lys Leu Val Pro Thr Trp Gly Asp Thr Asn
1               5                   10                  15

Cys Asp Gly Val Val Asn Val Ala Asp Val Val Leu Asn Arg Phe
            20                  25                  30

Leu Asn Asp Pro Thr Tyr Ser Asn Ile Thr Asp Gln Gly Lys Val Asn
            35                  40                  45

Ala Asp Val Val Asp Pro Gln Asp Lys Ser Gly Ala Ala Val Asp Pro
50                  55                  60

Ala Gly Val Lys Leu Thr Val Ala Asp Ser Glu Ala Ile Leu Lys Ala
65                  70                  75                  80

Ile Val Glu Leu Ile Thr Leu Pro Gln
                85

<210> SEQ ID NO 32
<211> LENGTH: 269
<212> TYPE: DNA
<213> ORGANISM: Artificial Sequence
<220> FEATURE:
<223> OTHER INFORMATION: Polynucleotide

<400> SEQUENCE: 32
gcaccatcac ccggcacaaa gctcgttcct acatggggcg atacaaactg cgacggcgtt    60
gtaaatgttg ctgacgtagt agttcttaac agattcctca acgatcctac atattctaac   120
attactgatc agggtaaggt taacgcagac gttgttgatc ctcaggataa gtccggcgca   180
gcagttgatc ctgcaggcgt aaagctcaca gtagctgact ctgaggcaat cctcaaggct   240
atcgttgaac tcatcacact tcctcaagc                                     269

<210> SEQ ID NO 33
<211> LENGTH: 79
<212> TYPE: PRT
<213> ORGANISM: Artificial Sequence
<220> FEATURE:
<223> OTHER INFORMATION: Polypeptide

<400> SEQUENCE: 33

Pro Lys Gly Thr Ala Thr Val Leu Tyr Gly Asp Val Asp Asn Asp Gly
1               5                   10                  15

Asn Val Asp Ser Asp Asp Tyr Ala Tyr Met Arg Gln Trp Leu Ile Gly
            20                  25                  30

Met Ile Ala Asp Phe Pro Gly Gly Asp Ile Gly Leu Ala Asn Ala Asp
            35                  40                  45

Val Asp Gly Asp Gly Asn Val Asp Ser Asp Asp Tyr Ala Tyr Met Arg
50                  55                  60

Gln Trp Leu Ile Gly Met Ile Ser Glu Phe Pro Ala Glu Gln Lys
65                  70                  75

<210> SEQ ID NO 34
<211> LENGTH: 239
<212> TYPE: DNA
<213> ORGANISM: Artificial Sequence
<220> FEATURE:
<223> OTHER INFORMATION: Polynucleotide

<400> SEQUENCE: 34
```

```
ccaaaaggca cagctacagt attatatggt gacgttgata atgatggaaa tgttgattca    60
gacgactatg catatatgag acaatggttg atcggtatga ttgctgattt ccctggagga   120
gatatcggat tagctaatgc tgatgttgat ggagacggaa atgtagattc agatgactat   180
gcgtacatga acaatggtt aataggaatg atttccgagt cccagcaga acaaaaagc     239
```

```
<210> SEQ ID NO 35
<211> LENGTH: 53
<212> TYPE: DNA
<213> ORGANISM: Artificial Sequence
<220> FEATURE:
<223> OTHER INFORMATION: Polynucleotide

<400> SEQUENCE: 35
ctgccgctag catgcaccat caccatcacc acgccgtgac ctccaacgag acc            53

<210> SEQ ID NO 36
<211> LENGTH: 48
<212> TYPE: DNA
<213> ORGANISM: Artificial Sequence
<220> FEATURE:
<223> OTHER INFORMATION: Polynucleotide

<400> SEQUENCE: 36
tcccaagagc tccgtcgaac tagtgccacc gccaccgggg gggttgcc                  48

<210> SEQ ID NO 37
<211> LENGTH: 32
<212> TYPE: DNA
<213> ORGANISM: Artificial Sequence
<220> FEATURE:
<223> OTHER INFORMATION: Polynucleotide

<400> SEQUENCE: 37
atgtatacta gtaaatttat atatggtgat gt                                   32

<210> SEQ ID NO 38
<211> LENGTH: 35
<212> TYPE: DNA
<213> ORGANISM: Artificial Sequence
<220> FEATURE:
<223> OTHER INFORMATION: Polynucleotide

<400> SEQUENCE: 38
taccaagagc tcttattctt ctttctcttc aacag                                35

<210> SEQ ID NO 39
<211> LENGTH: 32
<212> TYPE: DNA
<213> ORGANISM: Artificial Sequence
<220> FEATURE:
<223> OTHER INFORMATION: Polynucleotide

<400> SEQUENCE: 39
tatccggagc tcgttggcgc tgcaggacac cg                                   32

<210> SEQ ID NO 40
<211> LENGTH: 64
<212> TYPE: DNA
<213> ORGANISM: Artificial Sequence
<220> FEATURE:
<223> OTHER INFORMATION: Polynucleotide

<400> SEQUENCE: 40
ttattcgagc tcacagcaac tacaacacca actacaacac caactacaac accaacgcct    60
``` aaat                                                         64

<210> SEQ ID NO 41
<211> LENGTH: 64
<212> TYPE: DNA
<213> ORGANISM: Artificial Sequence
<220> FEATURE:
<223> OTHER INFORMATION: Polynucleotide

<400> SEQUENCE: 41
ttattcgagc tcacagcaac tacaacacca actacaacac caactacaac accaacgcct    60
aaat                                                         64

<210> SEQ ID NO 42
<211> LENGTH: 35
<212> TYPE: DNA
<213> ORGANISM: Artificial Sequence
<220> FEATURE:
<223> OTHER INFORMATION: Polynucleotide

<400> SEQUENCE: 42
ttattcacta gtacatataa agtacctggt actcc                       35

<210> SEQ ID NO 43
<211> LENGTH: 36
<212> TYPE: DNA
<213> ORGANISM: Artificial Sequence
<220> FEATURE:
<223> OTHER INFORMATION: Polynucleotide

<400> SEQUENCE: 43
ttattcctcg agttagttct tgtacggcaa tgtatc                      36

<210> SEQ ID NO 44
<211> LENGTH: 54
<212> TYPE: DNA
<213> ORGANISM: Artificial Sequence
<220> FEATURE:
<223> OTHER INFORMATION: Polynucleotide

<400> SEQUENCE: 44
catattgcta gccatcacca tcaccatcac ggaccggtcc acgaccatca tccc   54

<210> SEQ ID NO 45
<211> LENGTH: 46
<212> TYPE: DNA
<213> ORGANISM: Artificial Sequence
<220> FEATURE:
<223> OTHER INFORMATION: Polynucleotide

<400> SEQUENCE: 45
ttattcctcg agttattaac tagtacagtg atcgtgcttg gggccc            46

<210> SEQ ID NO 46
<211> LENGTH: 22
<212> TYPE: DNA
<213> ORGANISM: Artificial Sequence
<220> FEATURE:
<223> OTHER INFORMATION: Polynucleotide

<400> SEQUENCE: 46
cgccggtggt ttatccgctg tg                                     22

<210> SEQ ID NO 47

```
<211> LENGTH: 42
<212> TYPE: DNA
<213> ORGANISM: Artificial Sequence
<220> FEATURE:
<223> OTHER INFORMATION: Polynucleotide

<400> SEQUENCE: 47
ttaatggtga tggtgatggt gaacaatgat agcgccatca gt                              42

<210> SEQ ID NO 48
<211> LENGTH: 23
<212> TYPE: DNA
<213> ORGANISM: Artificial Sequence
<220> FEATURE:
<223> OTHER INFORMATION: Polynucleotide

<400> SEQUENCE: 48
atttacaggt tgacattgga agt                                                   23

<210> SEQ ID NO 49
<211> LENGTH: 23
<212> TYPE: DNA
<213> ORGANISM: Artificial Sequence
<220> FEATURE:
<223> OTHER INFORMATION: Polynucleotide

<400> SEQUENCE: 49
atttacaggt tgacattgga agt                                                   23

<210> SEQ ID NO 50
<211> LENGTH: 22
<212> TYPE: DNA
<213> ORGANISM: Artificial Sequence
<220> FEATURE:
<223> OTHER INFORMATION: Polynucleotide

<400> SEQUENCE: 50
gacaaacaca ccgacaaaca ca                                                    22

<210> SEQ ID NO 51
<211> LENGTH: 24
<212> TYPE: DNA
<213> ORGANISM: Artificial Sequence
<220> FEATURE:
<223> OTHER INFORMATION: Polynucleotide

<400> SEQUENCE: 51
ctatatctcc aacatttact ccac                                                  24

<210> SEQ ID NO 52
<211> LENGTH: 1038
<212> TYPE: DNA
<213> ORGANISM: Artificial Sequence
<220> FEATURE:
<223> OTHER INFORMATION: Polynucleotide

<400> SEQUENCE: 52
atggcaaata caccggtatc aggcaatttg aaggttgaat tctacaacag caatccttca           60
gatactacta actcaatcaa tcctcagttc aaggttacta ataccggaag cagtgcaatt          120
gatttgtcca aactcacatt gagatattat tatacagtag acggacagaa agatcagacc          180
ttctggtgtg accatgctgc aataatcggc agtaacggca gctacaacgg aattacttca          240
aatgtaaaag gaacatttgt aaaaatgagt tcctcaacaa ataacgcaga cacctacctt          300
gaaataagct ttacaggcgg aactcttgaa ccgggtgcac atgttcagat acaaggtaga          360
```

-continued

```
tttgcaaaga atgactggag taactataca cagtcaaatg actactcatt caagtctgct    420
tcacagtttg ttgaatggga tcaggtaaca gcatacttga acggtgttct tgtatggggt    480
aaagaacccg gtggcagtgt agtaccatca acacagcctg taacaacacc acctgcaaca    540
acaaaaccac ctgcaacaac aataccgccg tcagatgatc cgaatgcagg atccaatgca    600
ataaagatta aggtggacac agtaaatgca aaaccgggag acacagtaaa tatacctgta    660
agattcagtg gtataccatc caagggaata gcaaactgtg actttgtata cagctatgac    720
ccgaatgtac ttgagataat agagataaaa ccgggagaat tgatagttga cccgaatcct    780
gacaagagct ttgatactgc agtatatcct gacagaaaga taatagtatt cctgtttgca    840
gaagacagcg gaacaggagc gtatgcaata actaaagacg gagtatttgc tacgatagta    900
gcgaaagtaa aatccggagc acctaacgga ctcagtgtaa tcaaatttgt agaagtaggc    960
ggatttgcga acaatgacct tgtagaacag aggacacagt tctttgacgg tggagtaaat   1020
gttggagata caacataa                                                 1038
```

<210> SEQ ID NO 53
<211> LENGTH: 345
<212> TYPE: PRT
<213> ORGANISM: Artificial Sequence
<220> FEATURE:
<223> OTHER INFORMATION: Polypeptide

<400> SEQUENCE: 53

```
Met Ala Asn Thr Pro Val Ser Gly Asn Leu Lys Val Glu Phe Tyr Asn
1               5                   10                  15

Ser Asn Pro Ser Asp Thr Thr Asn Ser Ile Asn Pro Gln Phe Lys Val
            20                  25                  30

Thr Asn Thr Gly Ser Ser Ala Ile Asp Leu Ser Lys Leu Thr Leu Arg
        35                  40                  45

Tyr Tyr Tyr Thr Val Asp Gly Gln Lys Asp Gln Thr Phe Trp Cys Asp
    50                  55                  60

His Ala Ile Ile Gly Ser Asn Gly Ser Tyr Asn Gly Ile Thr Ser
65                  70                  75                  80

Asn Val Lys Gly Thr Phe Val Lys Met Ser Ser Thr Asn Asn Ala
                85                  90                  95

Asp Thr Tyr Leu Glu Ile Ser Phe Thr Gly Gly Thr Leu Glu Pro Gly
            100                 105                 110

Ala His Val Gln Ile Gln Gly Arg Phe Ala Lys Asn Asp Trp Ser Asn
        115                 120                 125

Tyr Thr Gln Ser Asn Asp Tyr Ser Phe Lys Ser Ala Ser Gln Phe Val
    130                 135                 140

Glu Trp Asp Gln Val Thr Ala Tyr Leu Asn Gly Val Leu Val Trp Gly
145                 150                 155                 160

Lys Glu Pro Gly Gly Ser Val Val Pro Ser Thr Gln Pro Val Thr Thr
                165                 170                 175

Pro Pro Ala Thr Thr Lys Pro Pro Ala Thr Thr Ile Pro Pro Ser Asp
            180                 185                 190

Asp Pro Asn Ala Gly Ser Asn Ala Ile Lys Ile Lys Val Asp Thr Val
        195                 200                 205

Asn Ala Lys Pro Gly Asp Thr Val Asn Ile Pro Val Arg Phe Ser Gly
    210                 215                 220

Ile Pro Ser Lys Gly Ile Ala Asn Cys Asp Phe Val Tyr Ser Tyr Asp
225                 230                 235                 240
```

Pro Asn Val Leu Glu Ile Ile Glu Ile Lys Pro Gly Glu Leu Ile Val
                245                 250                 255

Asp Pro Asn Pro Asp Lys Ser Phe Asp Thr Ala Val Tyr Pro Asp Arg
            260                 265                 270

Lys Ile Ile Val Phe Leu Phe Ala Glu Asp Ser Gly Thr Gly Ala Tyr
        275                 280                 285

Ala Ile Thr Lys Asp Gly Val Phe Ala Thr Ile Val Ala Lys Val Lys
    290                 295                 300

Ser Gly Ala Pro Asn Gly Leu Ser Val Ile Lys Phe Val Glu Val Gly
305                 310                 315                 320

Gly Phe Ala Asn Asn Asp Leu Val Glu Gln Arg Thr Gln Phe Phe Asp
                325                 330                 335

Gly Gly Val Asn Val Gly Asp Thr Thr
            340                 345

<210> SEQ ID NO 54
<211> LENGTH: 1047
<212> TYPE: DNA
<213> ORGANISM: Artificial Sequence
<220> FEATURE:
<223> OTHER INFORMATION: Polynucleotide

<400> SEQUENCE: 54
atggcaaata caccggtatc aggcaatttg aaggttgaat tctacaacag caatccttca      60
gatactacta actcaatcaa tcctcagttc aaggttacta ataccggaag cagtgcaatt     120
gatttgtcca aactcacatt gagatattat tatacagtag acggacagaa agatcagacc     180
ttctggtgtg accatgctgc aataatcggc agtaacggca gctacaacgg aattacttca     240
aatgtaaaag gaacatttgt aaaaatgagt tcctcaacaa ataacgcaga cacctacctt     300
gaaataagct ttacaggcgg aactcttgaa ccgggtgcac atgttcagat acaaggtaga     360
tttgcaaaga tgactggag taactataca cagtcaaatg actactcatt caagtctgct     420
tcacagtttg ttgaatggga tcaggtaaca gcatacttga acggtgttct tgtatggggt     480
aaagaacccg gtggcagtgt agtaccatca acacagcctg taacaacacc acctgcaaca     540
acaaaaccac ctgcaacaac aataccgccg tcagatgatc cgaatgcagg atccgggaaa     600
agttcaccag gaataaaaat gaaaattcaa attggtgatg taaaagctaa tcagggagat     660
acagttatag tacctataac tttcaatgaa gttcctgtaa tgggtgttaa taactgtaat     720
ttcactttag cttatgacaa aaatattatg gaatttatct ctgctgatgc aggtgatatt     780
gtaacattgc caatggctaa ctatagctac aatatgccat ctgatgggct agtaaaattt     840
ttatataatg atcaagctca aggtgcaatg tcaataaaag aagatggtac ttttgctaat     900
gttaaattta aaattaagca gagtgccgca tttgggaaat attcagtagg catcaaagca     960
attggttcaa tttccgcttt aagcaatagt aagttaatac ctattgaatc aatatttaaa    1020
gatggaagca ttactgtaac taattaa                                        1047

<210> SEQ ID NO 55
<211> LENGTH: 348
<212> TYPE: PRT
<213> ORGANISM: Artificial Sequence
<220> FEATURE:
<223> OTHER INFORMATION: Polypeptide

<400> SEQUENCE: 55

Met Ala Asn Thr Pro Val Ser Gly Asn Leu Lys Val Glu Phe Tyr Asn

| | 1 | | | | 5 | | | | | 10 | | | | | 15 | |
|---|---|---|---|---|---|---|---|---|---|---|---|---|---|---|---|---|
| Ser | Asn | Pro | Ser | Asp | Thr | Thr | Asn | Ser | Ile | Asn | Pro | Gln | Phe | Lys | Val |
| | | | | 20 | | | | | 25 | | | | | 30 | | |
| Thr | Asn | Thr | Gly | Ser | Ser | Ala | Ile | Asp | Leu | Ser | Lys | Leu | Thr | Leu | Arg |
| | | | | 35 | | | | | 40 | | | | | 45 | | |
| Tyr | Tyr | Tyr | Thr | Val | Asp | Gly | Gln | Lys | Asp | Gln | Thr | Phe | Trp | Cys | Asp |
| | | | 50 | | | | | 55 | | | | | 60 | | |
| His | Ala | Ala | Ile | Ile | Gly | Ser | Asn | Gly | Ser | Tyr | Asn | Gly | Ile | Thr | Ser |
| 65 | | | | | 70 | | | | | 75 | | | | | 80 |
| Asn | Val | Lys | Gly | Thr | Phe | Val | Lys | Met | Ser | Ser | Ser | Thr | Asn | Asn | Ala |
| | | | | 85 | | | | | 90 | | | | | 95 | | |
| Asp | Thr | Tyr | Leu | Glu | Ile | Ser | Phe | Thr | Gly | Thr | Leu | Glu | Pro | Gly |
| | | | | 100 | | | | | 105 | | | | | 110 | |
| Ala | His | Val | Gln | Ile | Gln | Gly | Arg | Phe | Ala | Lys | Asn | Asp | Trp | Ser | Asn |
| | | | | 115 | | | | | 120 | | | | | 125 | | |
| Tyr | Thr | Gln | Ser | Asn | Asp | Tyr | Ser | Phe | Lys | Ser | Ala | Ser | Gln | Phe | Val |
| | | | 130 | | | | | 135 | | | | | 140 | | |
| Glu | Trp | Asp | Gln | Val | Thr | Ala | Tyr | Leu | Asn | Gly | Val | Leu | Val | Trp | Gly |
| 145 | | | | | 150 | | | | | 155 | | | | | 160 |
| Lys | Glu | Pro | Gly | Gly | Ser | Val | Val | Pro | Ser | Thr | Gln | Pro | Val | Thr | Thr |
| | | | | 165 | | | | | 170 | | | | | 175 | |
| Pro | Pro | Ala | Thr | Thr | Lys | Pro | Pro | Ala | Thr | Thr | Ile | Pro | Pro | Ser | Asp |
| | | | | 180 | | | | | 185 | | | | | 190 | | |
| Asp | Pro | Asn | Ala | Gly | Ser | Gly | Lys | Ser | Ser | Pro | Gly | Asn | Lys | Met | Lys |
| | | | 195 | | | | | 200 | | | | | 205 | | |
| Ile | Gln | Ile | Gly | Asp | Val | Lys | Ala | Asn | Gln | Gly | Asp | Thr | Val | Ile | Val |
| | | | 210 | | | | | 215 | | | | | 220 | | |
| Pro | Ile | Thr | Phe | Asn | Glu | Val | Pro | Val | Met | Gly | Val | Asn | Asn | Cys | Asn |
| 225 | | | | | 230 | | | | | 235 | | | | | 240 |
| Phe | Thr | Leu | Ala | Tyr | Asp | Lys | Asn | Ile | Met | Glu | Phe | Ile | Ser | Ala | Asp |
| | | | | 245 | | | | | 250 | | | | | 255 | |
| Ala | Gly | Asp | Ile | Val | Thr | Leu | Pro | Met | Ala | Asn | Tyr | Ser | Tyr | Asn | Met |
| | | | 260 | | | | | 265 | | | | | 270 | | |
| Pro | Ser | Asp | Gly | Leu | Val | Lys | Phe | Leu | Tyr | Asn | Asp | Gln | Ala | Gln | Gly |
| | | | 275 | | | | | 280 | | | | | 285 | | |
| Ala | Met | Ser | Ile | Lys | Glu | Asp | Gly | Thr | Phe | Ala | Asn | Val | Lys | Phe | Lys |
| | | | 290 | | | | | 295 | | | | | 300 | | |
| Ile | Lys | Gln | Ser | Ala | Ala | Phe | Gly | Lys | Tyr | Ser | Val | Gly | Ile | Lys | Ala |
| 305 | | | | | 310 | | | | | 315 | | | | | 320 |
| Ile | Gly | Ser | Ile | Ser | Ala | Leu | Ser | Asn | Ser | Lys | Leu | Ile | Pro | Ile | Glu |
| | | | | 325 | | | | | 330 | | | | | 335 | |
| Ser | Ile | Phe | Lys | Asp | Gly | Ser | Ile | Thr | Val | Thr | Asn |
| | | | | 340 | | | | | 345 | | | |

<210> SEQ ID NO 56
<211> LENGTH: 1020
<212> TYPE: DNA
<213> ORGANISM: Artificial Sequence
<220> FEATURE:
<223> OTHER INFORMATION: Polynucleotide

<400> SEQUENCE: 56
atggcaaata caccggtatc aggcaatttg aaggttgaat tctacaacag caatccttca    60
gatactacta actcaatcaa tcctcagttc aaggttacta ataccggaag cagtgcaatt   120

| | | |
|---|---|---|
| gatttgtcca aactcacatt gagatattat tatacagtag acggacagaa agatcagacc | 180 | |
| ttctggtgtg accatgctgc aataatcggc agtaacggca gctacaacgg aattacttca | 240 | |
| aatgtaaaag gaacatttgt aaaaatgagt tcctcaacaa ataacgcaga cacctacctt | 300 | |
| gaaataagct ttacaggcgg aactcttgaa ccgggtgcac atgttcagat acaaggtaga | 360 | |
| tttgcaaaga atgactggag taactataca cagtcaaatg actactcatt caagtctgct | 420 | |
| tcacagtttg ttgaatggga tcaggtaaca gcatacttga acggtgttct tgtatggggt | 480 | |
| aaagaacccg gtggcagtgt agtaccatca acacagcctg taacaacacc acctgcaaca | 540 | |
| acaaaaccac ctgcaacaac aataccgccg tcagatgatc cgaatgcagg atccgctaac | 600 | |
| agaaccgctg ctgacggaac agttgaatgg cttatcccaa cagtaactgc agctccaggc | 660 | |
| cagacggtca ctatgcccgt agtagtcaag agttcaagtc ttgcagttgc tggtgcgcag | 720 | |
| ttcaagatcc aggcggcgac aggcgtacgt tattagtcca agacggacgg tgacgcttac | 780 | |
| ggttcaggca ttgtgtacaa taatagtaag tatgcttttg acagggtgc aggtagagga | 840 | |
| atagttgcag ctgatgattc ggttgtgctt actcttgcat atacagttcc cgctgattgt | 900 | |
| gctgaaggta catatgatgt caagtggtct gatgcgtttg taagtgatac agacggacag | 960 | |
| aatatcacaa gtaaggttac tcttactgat ggcgctatca ttgttaagaa ggataactaa | 1020 | |

<210> SEQ ID NO 57
<211> LENGTH: 338
<212> TYPE: PRT
<213> ORGANISM: Artificial Sequence
<220> FEATURE:
<223> OTHER INFORMATION: Polypeptide

<400> SEQUENCE: 57

```
Met Ala Asn Thr Pro Val Ser Gly Asn Leu Lys Val Glu Phe Tyr Asn
1               5                   10                  15

Ser Asn Pro Ser Asp Thr Thr Asn Ser Ile Asn Pro Gln Phe Lys Val
            20                  25                  30

Thr Asn Thr Gly Ser Ser Ala Ile Asp Leu Ser Lys Leu Thr Leu Arg
        35                  40                  45

Tyr Tyr Tyr Thr Val Asp Gly Gln Lys Asp Gln Thr Phe Trp Cys Asp
    50                  55                  60

His Ala Ala Ile Ile Gly Ser Asn Gly Ser Tyr Asn Gly Ile Thr Ser
65                  70                  75                  80

Asn Val Lys Gly Thr Phe Val Lys Met Ser Ser Ser Thr Asn Asn Ala
                85                  90                  95

Asp Thr Tyr Leu Glu Ile Ser Phe Thr Gly Gly Thr Leu Glu Pro Gly
            100                 105                 110

Ala His Val Gln Ile Gln Gly Arg Phe Ala Lys Asn Asp Trp Ser Asn
        115                 120                 125

Tyr Thr Gln Ser Asn Asp Tyr Ser Phe Lys Ser Ala Ser Gln Phe Val
    130                 135                 140

Glu Trp Asp Gln Val Thr Ala Tyr Leu Asn Gly Val Leu Val Trp Gly
145                 150                 155                 160

Lys Glu Pro Gly Gly Ser Val Val Pro Ser Thr Gln Pro Val Thr Thr
                165                 170                 175

Pro Pro Ala Thr Thr Lys Pro Pro Ala Thr Thr Ile Pro Pro Ser Asp
            180                 185                 190

Asp Pro Asn Ala Gly Ser Ala Asn Arg Thr Ala Ala Asp Gly Thr Val
        195                 200                 205
```

Glu Trp Leu Ile Pro Thr Val Thr Ala Ala Pro Gly Gln Thr Val Thr
    210                 215                 220

Met Pro Val Val Val Lys Ser Ser Ser Leu Ala Val Ala Gly Ala Gln
225                 230                 235                 240

Phe Lys Ile Gln Ala Ala Thr Gly Val Arg Tyr Ser Lys Thr Asp Gly
                245                 250                 255

Asp Ala Tyr Gly Ser Gly Ile Val Tyr Asn Asn Ser Lys Tyr Ala Phe
            260                 265                 270

Gly Gln Gly Ala Gly Arg Gly Ile Val Ala Ala Asp Asp Ser Val Val
            275                 280                 285

Leu Thr Leu Ala Tyr Thr Val Pro Ala Asp Cys Ala Glu Gly Thr Tyr
    290                 295                 300

Asp Val Lys Trp Ser Asp Ala Phe Val Ser Asp Thr Asp Gly Gln Asn
305                 310                 315                 320

Ile Thr Ser Lys Val Thr Leu Thr Asp Gly Ala Ile Ile Val Lys Lys
                325                 330                 335

Asp Asn

<210> SEQ ID NO 58
<211> LENGTH: 1029
<212> TYPE: DNA
<213> ORGANISM: Artificial Sequence
<220> FEATURE:
<223> OTHER INFORMATION: Polynucleotide

<400> SEQUENCE: 58

| | | | | |
|---|---|---|---|---|
| atggcaaata caccggtatc aggcaatttg aaggttgaat tctacaacag caatccttca | | | | 60 |
| gatactacta actcaatcaa tcctcagttc aaggttacta ataccggaag cagtgcaatt | | | | 120 |
| gatttgtcca aactcacatt gagatattat tatacagtag acggacagaa agatcagacc | | | | 180 |
| ttctggtgtg accatgctgc aataatcggc agtaacggca gctacaacgg aattacttca | | | | 240 |
| aatgtaaaag gaacatttgt aaaaatgagt tcctcaacaa ataacgcaga cacctacctt | | | | 300 |
| gaaataagct ttacaggcgg aactcttgaa ccgggtgcac atgttcagat acaaggtaga | | | | 360 |
| tttgcaaaga tgactggag taactataca cagtcaaatg actactcatt caagtctgct | | | | 420 |
| tcacagtttg ttgaatggga tcaggtaaca gcatacttga acggtgttct tgtatggggt | | | | 480 |
| aaagaacccg gtggcagtgt agtaccatca cacagcctg taacaacacc acctgcaaca | | | | 540 |
| acaaaaccac ctgcaacaac aataccgccg tcagatgatc cgaatgcagg atccgattta | | | | 600 |
| caggttgaca ttggaagtac tagtggaaaa gcaggtagtg ttgttagtgt acctataaca | | | | 660 |
| tttactaatg tacctaaatc aggtatctat gctctaagtt ttagaacaaa tttcgaccca | | | | 720 |
| caaaaggtaa ctgtagcaag tatagatgct ggctcactga ttgaaaatgc ttctgatttt | | | | 780 |
| actacttatt ataataatga aaatggtttt gcatcaatga cgtttgaagc cccagttgat | | | | 840 |
| agagctagaa tcatagatag tgatggtgta tttgcaacca ttaactttaa agttagtgat | | | | 900 |
| agtgccaaag taggtgaact ttacaatatt actactaata gtgcatatac ttcattctat | | | | 960 |
| tattctggaa ctgatgaaat caaaaatgtt gtttacaatg atggaaaaat tgaggtaatt | | | | 1020 |
| gcaagttaa | | | | 1029 |

<210> SEQ ID NO 59
<211> LENGTH: 342
<212> TYPE: PRT
<213> ORGANISM: Artificial Sequence
<220> FEATURE:
<223> OTHER INFORMATION: Polypeptide

<400> SEQUENCE: 59

```
Met Ala Asn Thr Pro Val Ser Gly Asn Leu Lys Val Glu Phe Tyr Asn
1               5                  10                  15

Ser Asn Pro Ser Asp Thr Thr Asn Ser Ile Asn Pro Gln Phe Lys Val
            20                  25                  30

Thr Asn Thr Gly Ser Ser Ala Ile Asp Leu Ser Lys Leu Thr Leu Arg
        35                  40                  45

Tyr Tyr Tyr Thr Val Asp Gly Gln Lys Asp Gln Thr Phe Trp Cys Asp
50                  55                  60

His Ala Ala Ile Ile Gly Ser Asn Gly Ser Tyr Asn Gly Ile Thr Ser
65                  70                  75                  80

Asn Val Lys Gly Thr Phe Val Lys Met Ser Ser Ser Thr Asn Asn Ala
                85                  90                  95

Asp Thr Tyr Leu Glu Ile Ser Phe Thr Gly Thr Leu Glu Pro Gly
            100                 105                 110

Ala His Val Gln Ile Gln Gly Arg Phe Ala Lys Asn Asp Trp Ser Asn
        115                 120                 125

Tyr Thr Gln Ser Asn Asp Tyr Ser Phe Lys Ser Ala Ser Gln Phe Val
    130                 135                 140

Glu Trp Asp Gln Val Thr Ala Tyr Leu Asn Gly Val Leu Val Trp Gly
145                 150                 155                 160

Lys Glu Pro Gly Gly Ser Val Val Pro Ser Thr Gln Pro Val Thr Thr
                165                 170                 175

Pro Pro Ala Thr Thr Lys Pro Pro Ala Thr Thr Ile Pro Pro Ser Asp
            180                 185                 190

Asp Pro Asn Ala Gly Ser Asp Leu Gln Val Asp Ile Gly Ser Thr Ser
        195                 200                 205

Gly Lys Ala Gly Ser Val Val Ser Val Pro Ile Thr Phe Thr Asn Val
    210                 215                 220

Pro Lys Ser Gly Ile Tyr Ala Leu Ser Phe Arg Thr Asn Phe Asp Pro
225                 230                 235                 240

Gln Lys Val Thr Val Ala Ser Ile Asp Ala Gly Ser Leu Ile Glu Asn
                245                 250                 255

Ala Ser Asp Phe Thr Thr Tyr Tyr Asn Asn Glu Asn Gly Phe Ala Ser
            260                 265                 270

Met Thr Phe Glu Ala Pro Val Asp Arg Ala Arg Ile Ile Asp Ser Asp
        275                 280                 285

Gly Val Phe Ala Thr Ile Asn Phe Lys Val Ser Asp Ser Ala Lys Val
    290                 295                 300

Gly Glu Leu Tyr Asn Ile Thr Thr Asn Ser Ala Tyr Thr Ser Phe Tyr
305                 310                 315                 320

Tyr Ser Gly Thr Asp Glu Ile Lys Asn Val Val Tyr Asn Asp Gly Lys
                325                 330                 335

Ile Glu Val Ile Ala Ser
            340
```

<210> SEQ ID NO 60
<211> LENGTH: 34
<212> TYPE: DNA
<213> ORGANISM: Artificial Sequence
<220> FEATURE:
<223> OTHER INFORMATION: Polynucleotide

<400> SEQUENCE: 60

<210> SEQ ID NO 61
<211> LENGTH: 32
<212> TYPE: DNA
<213> ORGANISM: Artificial Sequence
<220> FEATURE:
<223> OTHER INFORMATION: Polynucleotide

<400> SEQUENCE: 61
aaattactcg agctagttgg cgctgcagga ca    32

<210> SEQ ID NO 62
<211> LENGTH: 52
<212> TYPE: DNA
<213> ORGANISM: Artificial Sequence
<220> FEATURE:
<223> OTHER INFORMATION: Polynucleotide

<400> SEQUENCE: 62
tgatccatgg cacaccatca ccatcaccat gcaccatcac ccggcacaaa gc    52

<210> SEQ ID NO 63
<211> LENGTH: 37
<212> TYPE: DNA
<213> ORGANISM: Artificial Sequence
<220> FEATURE:
<223> OTHER INFORMATION: Polynucleotide

<400> SEQUENCE: 63
atgcttggta ccgcttgagg aagtgtgatg agttcaa    37

<210> SEQ ID NO 64
<211> LENGTH: 1422
<212> TYPE: DNA
<213> ORGANISM: Artificial Sequence
<220> FEATURE:
<223> OTHER INFORMATION: Polynucleotide

<400> SEQUENCE: 64
atggcacacc atcaccatca ccatgcgaaa tcccccgccg cccggaaggg cggccctccg    60
gtcgctgtcg cggtgaccgc ggccctcgcc ctgctgatcg cgctcctctc ccccggagtc   120
gcgcaggccg ccggtctcac cgccacagtc accaaagaat cctcgtggga caacggctac   180
tccgcgtccg tcaccgtccg caacgacacc tcgagcaccg tctcccagtg ggaggtcgtc   240
ctcaccctgc ccggcggcac tacagtggcc caggtgtgga acgccagca ccagcagc     300
ggcaactccc acaccttcac cggggtttcc tggaacagca ccatcccgcc cggaggcacc   360
gcctccttcg gcttcatcgc ttccggcagc ggcgaaccca ccactgcac catcaacggc   420
gcccctgcg acgaaggctc cgagccgggc ggccccggcg gtcccggaac cccctccccc   480
gaccccggca cgcagcccgg caccggcacc ccggtcgagc ggtacggcaa agtccaggtc   540
tgcggcaccc agctctgcga cgagcacggc aacccggtcc aactgcgcgg catgagcacc   600
cacggcatcc agtggttcga ccactgcctg accgacagct cgctggacgc cctggcctac   660
gactggaagg ccgacatcat ccgcctgtcc atgtacatcc aggaagacgg ctacgagacc   720
aacccgcgcg gcttcaccga ccggatgcac cagctcatcg acatggccac ggcgcgcggc   780
ctgtacgtga tcgtggactg gcacatcctc acccgggcg atccccacta caacctggac   840
cgggccaaga ccttcttcgc ggaaatcgcc cagcgccacg ccagcaagac caacgtgctc   900
tacgagatcg ccaacgaacc caacggagtg agctgggcct ccatcaagag ctacgccgaa   960

-continued

```
gaggtcatcc cggtgatccg ccagcgcgac cccgactcgg tgatcatcgt gggcacccgc    1020
ggctggtcgt cgctcggcgt ctccgaaggc tccggcccg ccgagatcgc ggccaacccg     1080
gtcaacgcct ccaacatcat gtacgccttc cacttctacg cggcctcgca ccgcgacaac    1140
tacctcaacg cgctgcgtga ggcctccgag ctgttcccgg tcttcgtcac cgagttcggc    1200
accgagacct acaccggtga cggcgccaac gacttccaga tggccgaccg ctacatcgac    1260
ctgatggcgg aacggaagat cgggtggacc aagtggaact actcggacga cttccgttcc    1320
ggcgcggtct tccagccggg cacctgcgcg tccggcggcc cgtggagcgg ttcgtcgctg    1380
aaggcgtccg gacagtgggt gcggagcaag ctccagtcct ga                       1422
```

<210> SEQ ID NO 65
<211> LENGTH: 473
<212> TYPE: PRT
<213> ORGANISM: Artificial Sequence
<220> FEATURE:
<223> OTHER INFORMATION: Polypeptide

<400> SEQUENCE: 65

```
Met Ala His His His His His His Ala Lys Ser Pro Ala Ala Arg Lys
1               5                   10                  15

Gly Gly Pro Pro Val Ala Val Ala Val Thr Ala Ala Leu Ala Leu Leu
            20                  25                  30

Ile Ala Leu Leu Ser Pro Gly Val Ala Gln Ala Ala Gly Leu Thr Ala
        35                  40                  45

Thr Val Thr Lys Glu Ser Ser Trp Asp Asn Gly Tyr Ser Ala Ser Val
    50                  55                  60

Thr Val Arg Asn Asp Thr Ser Ser Thr Val Ser Gln Trp Glu Val Val
65                  70                  75                  80

Leu Thr Leu Pro Gly Gly Thr Thr Val Ala Gln Val Trp Asn Ala Gln
                85                  90                  95

His Thr Ser Ser Gly Asn Ser His Thr Phe Thr Gly Val Ser Trp Asn
            100                 105                 110

Ser Thr Ile Pro Pro Gly Gly Thr Ala Ser Phe Gly Phe Ile Ala Ser
        115                 120                 125

Gly Ser Gly Glu Pro Thr His Cys Thr Ile Asn Gly Ala Pro Cys Asp
    130                 135                 140

Glu Gly Ser Glu Pro Gly Gly Pro Gly Gly Pro Gly Thr Pro Ser Pro
145                 150                 155                 160

Asp Pro Gly Thr Gln Pro Gly Thr Gly Thr Pro Val Glu Arg Tyr Gly
                165                 170                 175

Lys Val Gln Val Cys Gly Thr Gln Leu Cys Asp Glu His Gly Asn Pro
            180                 185                 190

Val Gln Leu Arg Gly Met Ser Thr His Gly Ile Gln Trp Phe Asp His
        195                 200                 205

Cys Leu Thr Asp Ser Ser Leu Asp Ala Leu Ala Tyr Asp Trp Lys Ala
    210                 215                 220

Asp Ile Ile Arg Leu Ser Met Tyr Ile Gln Glu Asp Gly Tyr Glu Thr
225                 230                 235                 240

Asn Pro Arg Gly Phe Thr Asp Arg Met His Gln Leu Ile Asp Met Ala
                245                 250                 255

Thr Ala Arg Gly Leu Tyr Val Ile Val Asp Trp His Ile Leu Thr Pro
            260                 265                 270

Gly Asp Pro His Tyr Asn Leu Asp Arg Ala Lys Thr Phe Phe Ala Glu
```

```
                275                 280                 285
Ile Ala Gln Arg His Ala Ser Lys Thr Asn Val Leu Tyr Glu Ile Ala
    290                 295                 300

Asn Glu Pro Asn Gly Val Ser Trp Ala Ser Ile Lys Ser Tyr Ala Glu
305                 310                 315                 320

Glu Val Ile Pro Val Ile Arg Gln Arg Asp Pro Asp Ser Val Ile Ile
                325                 330                 335

Val Gly Thr Arg Gly Trp Ser Ser Leu Gly Val Ser Glu Gly Ser Gly
            340                 345                 350

Pro Ala Glu Ile Ala Ala Asn Pro Val Asn Ala Ser Asn Ile Met Tyr
        355                 360                 365

Ala Phe His Phe Tyr Ala Ala Ser His Arg Asp Asn Tyr Leu Asn Ala
    370                 375                 380

Leu Arg Glu Ala Ser Glu Leu Phe Pro Val Phe Val Thr Glu Phe Gly
385                 390                 395                 400

Thr Glu Thr Tyr Thr Gly Asp Gly Ala Asn Asp Phe Gln Met Ala Asp
                405                 410                 415

Arg Tyr Ile Asp Leu Met Ala Glu Arg Lys Ile Gly Trp Thr Lys Trp
            420                 425                 430

Asn Tyr Ser Asp Asp Phe Arg Ser Gly Ala Val Phe Gln Pro Gly Thr
        435                 440                 445

Cys Ala Ser Gly Gly Pro Trp Ser Gly Ser Ser Leu Lys Ala Ser Gly
    450                 455                 460

Gln Trp Val Arg Ser Lys Leu Gln Ser
465                 470

<210> SEQ ID NO 66
<211> LENGTH: 921
<212> TYPE: DNA
<213> ORGANISM: Artificial Sequence
<220> FEATURE:
<223> OTHER INFORMATION: Polynucleotide

<400> SEQUENCE: 66
atggctagca tgcaccatca ccatcaccac gccgtgacct ccaacgagac cgggtaccac      60
gacgggtact tctactcgtt ctggaccgac gcgcctggaa cggtctccat ggagctgggc     120
cctggcggaa actacagcac ctcctggcgg aacaccggga acttcgtcgc cggtaaggga     180
tgggccaccg gtggccgccg gaccgtgacc tactccgcca gcttcaaccc gtcgggtaac     240
gcctacctga ccctctacgg gtggacgcgg aacccgctcg tggagtacta catcgtcgaa     300
agctggggca cctaccggcc caccggtacc tacatgggca cggtgaccac cgacggtggt     360
acctacgaca tctacaagac cacgcggtac aacgcgccct ccatcgaagg cacccggacc     420
ttcgaccagt actggagcgt ccgccagtcc aagcggacca gcggtaccat caccgcgggg     480
aaccacttcg acgcgtgggc ccgccacggt atgcacctcg aaccacgact ctacatgatc     540
atggcgaccg agggctacca gagcagcgga tcctccaacg tgacgttggg caccagcggc     600
ggtggaaacc ccgtgggggg caaccccccc ggtggcggca ccccccccgg tggcggtggc     660
tgcacggcga cgctgtccgc gggccagcag tggaacgacc gctacaacct caacgtcaac     720
gtcagcggct ccaacaactg gaccgtgacc gtgaacgttc cgtggccggc gaggatcatc     780
gccacctgga catccacgc cagctacccg gactcccaga ccttggttgc ccggcctaac     840
ggcaacggca caactggggg catgacgatc atgcacaacg caactggac gtggcccacg     900 gtgtcctgca gcgccaacta g                                              921
```

<210> SEQ ID NO 67
<211> LENGTH: 306
<212> TYPE: PRT
<213> ORGANISM: Artificial Sequence
<220> FEATURE:
<223> OTHER INFORMATION: Polypeptide

<400> SEQUENCE: 67

```
Met Ala Ser Met His His His His His Ala Val Thr Ser Asn Glu
1               5                   10                  15

Thr Gly Tyr His Asp Gly Tyr Phe Tyr Ser Phe Trp Thr Asp Ala Pro
            20                  25                  30

Gly Thr Val Ser Met Glu Leu Gly Pro Gly Gly Asn Tyr Ser Thr Ser
        35                  40                  45

Trp Arg Asn Thr Gly Asn Phe Val Ala Gly Lys Gly Trp Ala Thr Gly
    50                  55                  60

Gly Arg Arg Thr Val Thr Tyr Ser Ala Ser Phe Asn Pro Ser Gly Asn
65                  70                  75                  80

Ala Tyr Leu Thr Leu Tyr Gly Trp Thr Arg Asn Pro Leu Val Glu Tyr
                85                  90                  95

Tyr Ile Val Glu Ser Trp Gly Thr Tyr Arg Pro Thr Gly Thr Tyr Met
            100                 105                 110

Gly Thr Val Thr Thr Asp Gly Gly Thr Tyr Asp Ile Tyr Lys Thr Thr
        115                 120                 125

Arg Tyr Asn Ala Pro Ser Ile Glu Gly Thr Arg Thr Phe Asp Gln Tyr
    130                 135                 140

Trp Ser Val Arg Gln Ser Lys Arg Thr Ser Gly Thr Ile Thr Ala Gly
145                 150                 155                 160

Asn His Phe Asp Ala Trp Ala Arg His Gly Met His Leu Gly Thr His
                165                 170                 175

Asp Tyr Met Ile Met Ala Thr Glu Gly Tyr Gln Ser Ser Gly Ser Ser
            180                 185                 190

Asn Val Thr Leu Gly Thr Ser Gly Gly Gly Asn Pro Gly Gly Gly Asn
        195                 200                 205

Pro Pro Gly Gly Gly Asn Pro Pro Gly Gly Gly Cys Thr Ala Thr
    210                 215                 220

Leu Ser Ala Gly Gln Gln Trp Asn Asp Arg Tyr Asn Leu Asn Val Asn
225                 230                 235                 240

Val Ser Gly Ser Asn Asn Trp Thr Val Thr Val Asn Val Pro Trp Pro
                245                 250                 255

Ala Arg Ile Ile Ala Thr Trp Asn Ile His Ala Ser Tyr Pro Asp Ser
            260                 265                 270

Gln Thr Leu Val Ala Arg Pro Asn Gly Asn Gly Asn Asn Trp Gly Met
        275                 280                 285

Thr Ile Met His Asn Gly Asn Trp Thr Trp Pro Thr Val Ser Cys Ser
    290                 295                 300

Ala Asn
305
```

<210> SEQ ID NO 68
<211> LENGTH: 1146
<212> TYPE: DNA
<213> ORGANISM: Artificial Sequence
<220> FEATURE:
<223> OTHER INFORMATION: Polynucleotide

<400> SEQUENCE: 68

```
atggctagcc atcaccatca ccatcacgga ccggtccacg accatcatcc cgctccccac      60
tccaacgcga atccgagcg gctgcgctgg gctgccccg acggcttcta catcggcagc       120
gcggtcgcgg gcggcggcca ccacctggag caggactacc ccgacccctt cacccacgac      180
gggaaatacc gcagcatcct ggctcagcag ttcagctcag tctccccgga aaaccagatg      240
aagtgggagt acatccatcc tgagccggac cgctacgact cgccatggc cgacaagatc      300
gtcgacttcg cggagcgtaa cgaccagaag gtccgcggtc acaccctgct gtggcacagc      360
cagaaccccg agtggctcga gagggcgac tactcccctg aggagctgcg cgagatcctg       420
cgggaccaca tcaccaccgt ggtcggccgc tacgccggac ggatccacca gtgggatgtg      480
gccaacgaga tcttcgacga gcagggcaac ctgcgtactc aggagaacat ctggatccgc      540
gagctcggcc ccggcatcat cgctgacgcg ttccgctggg cgcacgaggc agacccgaac      600
gcggagctgt tcttcaacga ctacaacgtg gagggcatca cccgaagag cgacgcctac       660
tacgaactca tccaggagct gctcgacgac ggggttccgg tccacggctt ctccgtccag      720
gggcacctga gcaccccgcta cggcttcccg ggcgacctgg aacagaacct cgccggttc      780
gacgagctcg gtctggccac ggcgatcacc gagctggacg tgcgcatgga cctgccggcc      840
agcggcaagc cgaccccgaa gcagttggag cagcaggccg actactacca gcaggcgctt      900
gaagcgtgcc tggccgtgga aggctgcgac tccttcacga tctggggctt cacggacaag      960
tactcctggg tgccggtgtt cttccccgac gagggcgcgg cgacgatcat gacggagaag     1020
tacgagcgca gcccgctttt cttcgcgctg cagcagacgc tgcgggaagc ccggtgcgcg     1080
gacagcccca gccgggacc gggcaagccg aagccgggca agggcccaa gcacgatcac      1140
tgttga                                                                1146
```

<210> SEQ ID NO 69
<211> LENGTH: 381
<212> TYPE: PRT
<213> ORGANISM: Artificial Sequence
<220> FEATURE:
<223> OTHER INFORMATION: Polypeptide

<400> SEQUENCE: 69

```
Met Ala Ser His His His His His His Gly Pro Val His Asp His His
1               5                   10                  15

Pro Ala Pro His Ser Asn Ala Lys Ser Glu Arg Leu Arg Trp Ala Ala
            20                  25                  30

Pro Asp Gly Phe Tyr Ile Gly Ser Ala Val Ala Gly Gly His His
        35                  40                  45

Leu Glu Gln Asp Tyr Pro Asp Pro Phe Thr His Asp Gly Lys Tyr Arg
    50                  55                  60

Ser Ile Leu Ala Gln Gln Phe Ser Ser Val Ser Pro Glu Asn Gln Met
65                  70                  75                  80

Lys Trp Glu Tyr Ile His Pro Glu Pro Asp Arg Tyr Asp Phe Ala Met
                85                  90                  95

Ala Asp Lys Ile Val Asp Phe Ala Glu Arg Asn Asp Gln Lys Val Arg
            100                 105                 110

Gly His Thr Leu Leu Trp His Ser Gln Asn Pro Glu Trp Leu Glu Glu
        115                 120                 125

Gly Asp Tyr Ser Pro Glu Glu Leu Arg Glu Ile Leu Arg Asp His Ile
    130                 135                 140
```

Thr Thr Val Val Gly Arg Tyr Ala Gly Arg Ile His Gln Trp Asp Val
145                 150                 155                 160

Ala Asn Glu Ile Phe Asp Glu Gln Gly Asn Leu Arg Thr Gln Glu Asn
            165                 170                 175

Ile Trp Ile Arg Glu Leu Gly Pro Gly Ile Ile Ala Asp Ala Phe Arg
            180                 185                 190

Trp Ala His Glu Ala Asp Pro Asn Ala Glu Leu Phe Phe Asn Asp Tyr
        195                 200                 205

Asn Val Glu Gly Ile Asn Pro Lys Ser Asp Ala Tyr Tyr Glu Leu Ile
    210                 215                 220

Gln Glu Leu Leu Asp Asp Gly Val Pro Val His Gly Phe Ser Val Gln
225                 230                 235                 240

Gly His Leu Ser Thr Arg Tyr Gly Phe Pro Gly Asp Leu Glu Gln Asn
                245                 250                 255

Leu Arg Arg Phe Asp Glu Leu Gly Leu Ala Thr Ala Ile Thr Glu Leu
            260                 265                 270

Asp Val Arg Met Asp Leu Pro Ala Ser Gly Lys Pro Thr Pro Lys Gln
        275                 280                 285

Leu Glu Gln Gln Ala Asp Tyr Tyr Gln Gln Ala Leu Glu Ala Cys Leu
    290                 295                 300

Ala Val Glu Gly Cys Asp Ser Phe Thr Ile Trp Gly Phe Thr Asp Lys
305                 310                 315                 320

Tyr Ser Trp Val Pro Val Phe Phe Pro Asp Glu Gly Ala Ala Thr Ile
                325                 330                 335

Met Thr Glu Lys Tyr Glu Arg Lys Pro Ala Phe Phe Ala Leu Gln Gln
            340                 345                 350

Thr Leu Arg Glu Ala Arg Cys Ala Asp Ser Pro Lys Pro Gly Pro Gly
        355                 360                 365

Lys Pro Lys Pro Gly Lys Gly Pro Lys His Asp His Cys
    370                 375                 380

<210> SEQ ID NO 70
<211> LENGTH: 894
<212> TYPE: DNA
<213> ORGANISM: Artificial Sequence
<220> FEATURE:
<223> OTHER INFORMATION: Polynucleotide

<400> SEQUENCE: 70
atggctagca tgcaccatca ccatcaccac gccgtgacct ccaacgagac cgggtaccac      60
gacgggtact tctactcgtt ctggaccgac gcgcctggaa cggtctccat ggagctgggc     120
cctggcggaa actacagcac ctcctggcgg aacaccggga acttcgtcgc cggtaaggga     180
tgggccaccg gtggccgccg gaccgtgacc tactccgcca gcttcaaccc gtcgggtaac     240
gcctacctga ccctctacgg gtggacgcgg aacccgctcg tggagtacta catcgtcgaa     300
agctggggca cctaccggcc caccggtacc tacatgggca cggtgaccac cgacggtggt     360
acctacgaca tctacaagac cacgcggtac aacgcgccct ccatcgaagg cacccggacc     420
ttcgaccagt actggagcgt ccgccagtcc aagcggacca gcgtaccat caccgcgggg     480 aaccacttcg acgcgtgggc cgccacggt atgcacctcg aacccacga ctacatgatc     540 atggcgaccg agggctacca gagcagcgga tcctccaacg tgacgttggg caccagcggc     600
ggtggaaacc ccgtgggggg caaccccccc ggtggcggca accccccgg tggcggtggc     660 actagtaaat ttatatatgg tgatgttgat ggtaatggaa gtgtaagaat taatgatgct     720

```
gtcctaataa gagactatgt attaggaaaa atcaatgaat tcccatatga atatggtatg       780
cttgcagcag atgttgatgg taatggaagt ataaaaatta atgatgctgt tctagtaaga       840
gactacgtgt taggaaagat attttttattc cctgttgaag agaaagaaga ataa            894
```

```
<210> SEQ ID NO 71
<211> LENGTH: 297
<212> TYPE: PRT
<213> ORGANISM: Artificial Sequence
<220> FEATURE:
<223> OTHER INFORMATION: Polypeptide

<400> SEQUENCE: 71
```

```
Met Ala Ser Met His His His His His His Ala Val Thr Ser Asn Glu
1               5                   10                  15

Thr Gly Tyr His Asp Gly Tyr Phe Tyr Ser Phe Trp Thr Asp Ala Pro
            20                  25                  30

Gly Thr Val Ser Met Glu Leu Gly Pro Gly Gly Asn Tyr Ser Thr Ser
        35                  40                  45

Trp Arg Asn Thr Gly Asn Phe Val Ala Gly Lys Gly Trp Ala Thr Gly
    50                  55                  60

Gly Arg Arg Thr Val Thr Tyr Ser Ala Ser Phe Asn Pro Ser Gly Asn
65                  70                  75                  80

Ala Tyr Leu Thr Leu Tyr Gly Trp Thr Arg Asn Pro Leu Val Glu Tyr
                85                  90                  95

Tyr Ile Val Glu Ser Trp Gly Thr Tyr Arg Pro Thr Gly Thr Tyr Met
            100                 105                 110

Gly Thr Val Thr Thr Asp Gly Gly Thr Tyr Asp Ile Tyr Lys Thr Thr
        115                 120                 125

Arg Tyr Asn Ala Pro Ser Ile Glu Gly Thr Arg Thr Phe Asp Gln Tyr
    130                 135                 140

Trp Ser Val Arg Gln Ser Lys Arg Thr Ser Gly Thr Ile Thr Ala Gly
145                 150                 155                 160

Asn His Phe Asp Ala Trp Ala Arg His Gly Met His Leu Gly Thr His
                165                 170                 175

Asp Tyr Met Ile Met Ala Thr Glu Gly Tyr Gln Ser Ser Gly Ser Ser
            180                 185                 190

Asn Val Thr Leu Gly Thr Ser Gly Gly Asn Pro Gly Gly Gly Asn
        195                 200                 205

Pro Pro Gly Gly Gly Asn Pro Pro Gly Gly Gly Thr Ser Lys Phe
    210                 215                 220

Ile Tyr Gly Asp Val Asp Gly Asn Gly Ser Val Arg Ile Asn Asp Ala
225                 230                 235                 240

Val Leu Ile Arg Asp Tyr Val Leu Gly Lys Ile Asn Glu Phe Pro Tyr
                245                 250                 255

Glu Tyr Gly Met Leu Ala Ala Asp Val Asp Gly Asn Gly Ser Ile Lys
            260                 265                 270

Ile Asn Asp Ala Val Leu Val Arg Asp Tyr Val Leu Gly Lys Ile Phe
        275                 280                 285

Leu Phe Pro Val Glu Glu Lys Glu Glu
    290                 295
```

```
<210> SEQ ID NO 72
<211> LENGTH: 471
<212> TYPE: DNA
<213> ORGANISM: Artificial Sequence
<220> FEATURE:
```

<223> OTHER INFORMATION: Polynucleotide

<400> SEQUENCE: 72

```
gccggtggtt tatccgctgt gcagcctaat gttagtttag gcgaagtact ggatgtttct        60
gctaacagaa ccgctgctga cggaacagtt gaatggctta tcccaacagt aactgcagct       120
ccaggccaga cggtcactat gcccgtagta gtcaagagtt caagtcttgc agttgctggt       180
gcgcagttca agatccaggc ggcgacaggc gtaagttatt cgtccaagac ggacggtgac       240
gcttacggtt caggcattgt gtacaataat agtaagtatg cttttggaca gggtgcaggt       300
agaggaatag ttgcagctga tgattcggtt gtgcttactc ttgcatatac agttcccgct       360
gattgtgctg aaggtacata tgatgtcaag tggtctgatg cgtttgtaag tgatacagac       420
ggacagaata tcacaagtaa ggttactctt actgatggcg ctatcattgt t                471
```

<210> SEQ ID NO 73
<211> LENGTH: 157
<212> TYPE: PRT
<213> ORGANISM: Artificial Sequence
<220> FEATURE:
<223> OTHER INFORMATION: Polypeptide

<400> SEQUENCE: 73

```
Ala Gly Gly Leu Ser Ala Val Gln Pro Asn Val Ser Leu Gly Glu Val
1               5                   10                  15
Leu Asp Val Ser Ala Asn Arg Thr Ala Ala Asp Gly Thr Val Glu Trp
            20                  25                  30
Leu Ile Pro Thr Val Thr Ala Ala Pro Gly Gln Thr Val Thr Met Pro
        35                  40                  45
Val Val Val Lys Ser Ser Leu Ala Val Ala Gly Ala Gln Phe Lys
    50                  55                  60
Ile Gln Ala Ala Thr Gly Val Ser Tyr Ser Ser Lys Thr Asp Gly Asp
65                  70                  75                  80
Ala Tyr Gly Ser Gly Ile Val Tyr Asn Asn Ser Lys Tyr Ala Phe Gly
                85                  90                  95
Gln Gly Ala Gly Arg Gly Ile Val Ala Ala Asp Asp Ser Val Val Leu
            100                 105                 110
Thr Leu Ala Tyr Thr Val Pro Ala Asp Cys Ala Glu Gly Thr Tyr Asp
        115                 120                 125
Val Lys Trp Ser Asp Ala Phe Val Ser Asp Thr Asp Gly Gln Asn Ile
    130                 135                 140
Thr Ser Lys Val Thr Leu Thr Asp Gly Ala Ile Ile Val
145                 150                 155
```

<210> SEQ ID NO 74
<211> LENGTH: 435
<212> TYPE: DNA
<213> ORGANISM: Artificial Sequence
<220> FEATURE:
<223> OTHER INFORMATION: Polynucleotide

<400> SEQUENCE: 74

```
gatttacagg ttgacattgg aagtactagt ggaaaagcag gtagtgttgt tagtgtacct        60
ataacattta ctaatgtacc taatcaggt atctatgctc taagttttag aacaaatttc        120
gacccacaaa aggtaactgt agcaagtata gatgctggct cactgattga aaatgcttct       180
gattttacta cttattataa taatgaaaat ggttttgcat caatgacgtt tgaagcccca       240
gttgatagag ctagaatcat agatagtgat ggtgtatttg caaccattaa ctttaaagtt       300
```

```
agtgatagtg ccaaagtagg tgaactttac aatattacta ctaatagtgc atatacttca    360
ttctattatt ctggaactga tgaaatcaaa atgttgttt acaatgatgg aaaaattgag     420
gtaattgcaa gttaa                                                      435
```

<210> SEQ ID NO 75
<211> LENGTH: 144
<212> TYPE: PRT
<213> ORGANISM: Artificial Sequence
<220> FEATURE:
<223> OTHER INFORMATION: Polypeptide

<400> SEQUENCE: 75

```
Asp Leu Gln Val Asp Ile Gly Ser Thr Ser Gly Lys Ala Gly Ser Val
1               5                   10                  15

Val Ser Val Pro Ile Thr Phe Thr Asn Val Pro Lys Ser Gly Ile Tyr
            20                  25                  30

Ala Leu Ser Phe Arg Thr Asn Phe Asp Pro Gln Lys Val Thr Val Ala
        35                  40                  45

Ser Ile Asp Ala Gly Ser Leu Ile Glu Asn Ala Ser Asp Phe Thr Thr
    50                  55                  60

Tyr Tyr Asn Asn Glu Asn Gly Phe Ala Ser Met Thr Phe Glu Ala Pro
65                  70                  75                  80

Val Asp Arg Ala Arg Ile Ile Asp Ser Asp Gly Val Phe Ala Thr Ile
                85                  90                  95

Asn Phe Lys Val Ser Asp Ser Ala Lys Val Gly Glu Leu Tyr Asn Ile
            100                 105                 110

Thr Thr Asn Ser Ala Tyr Thr Ser Phe Tyr Tyr Ser Gly Thr Asp Glu
        115                 120                 125

Ile Lys Asn Val Val Tyr Asn Asp Gly Lys Ile Glu Val Ile Ala Ser
    130                 135                 140
```

<210> SEQ ID NO 76
<211> LENGTH: 453
<212> TYPE: DNA
<213> ORGANISM: Artificial Sequence
<220> FEATURE:
<223> OTHER INFORMATION: Polynucleotide

<400> SEQUENCE: 76

```
gggaaaagtt caccaggaaa taaatgaaa attcaaattg gtgatgtaaa agctaatcag     60
ggagatacag ttatagtacc tataactttc aatgaagttc ctgtaatggg tgttaataac   120
tgtaatttca ctttagctta tgacaaaaat attatggaat ttatctctgc tgatgcaggt   180
gatattgtaa cattgccaat ggctaactat agctacaata tgccatctga tgggctagta   240
aaatttttat ataatgatca agctcaaggt gcaatgtcaa taaagaaga tggtactttt    300 gctaatgtta aatttaaaat taagcagagt gccgcatttg gaaatattc agtaggcatc    360 aaagcaattg gttcaatttc cgctttaagc aatagtaagt taatacctat tgaatcaata   420
tttaaagatg gaagcattac tgtaactaat taa                                 453
```

<210> SEQ ID NO 77
<211> LENGTH: 150
<212> TYPE: PRT
<213> ORGANISM: Artificial Sequence
<220> FEATURE:
<223> OTHER INFORMATION: Polypeptide

<400> SEQUENCE: 77

```
Gly Lys Ser Ser Pro Gly Asn Lys Met Lys Ile Gln Ile Gly Asp Val
1               5                   10                  15

Lys Ala Asn Gln Gly Asp Thr Val Ile Val Pro Ile Thr Phe Asn Glu
            20                  25                  30

Val Pro Val Met Gly Val Asn Asn Cys Asn Phe Thr Leu Ala Tyr Asp
        35                  40                  45

Lys Asn Ile Met Glu Phe Ile Ser Ala Asp Ala Gly Asp Ile Val Thr
    50                  55                  60

Leu Pro Met Ala Asn Tyr Ser Tyr Asn Met Pro Ser Asp Gly Leu Val
65                  70                  75                  80

Lys Phe Leu Tyr Asn Asp Gln Ala Gln Gly Ala Met Ser Ile Lys Glu
                85                  90                  95

Asp Gly Thr Phe Ala Asn Val Lys Phe Lys Ile Lys Gln Ser Ala Ala
            100                 105                 110

Phe Gly Lys Tyr Ser Val Gly Ile Lys Ala Ile Gly Ser Ile Ser Ala
        115                 120                 125

Leu Ser Asn Ser Lys Leu Ile Pro Ile Glu Ser Ile Phe Lys Asp Gly
    130                 135                 140

Ser Ile Thr Val Thr Asn
145                 150
```

<210> SEQ ID NO 78
<211> LENGTH: 432
<212> TYPE: DNA
<213> ORGANISM: Artificial Sequence
<220> FEATURE:
<223> OTHER INFORMATION: Polynucleotide

<400> SEQUENCE: 78

```
ataaagatta aggtggacac agtaaatgca aaaccgggag acacagtaaa tatacctgta    60
agattcagtg gtataccatc caagggaata gcaaactgtg actttgtata cagctatgac   120
ccgaatgtac ttgagataat agagataaaa ccgggagaat tgatagttga cccgaatcct   180
gacaagagct ttgatactgc agtatatcct gacagaaaga taatagtatt cctgttttgca  240
gaagacagcg aacaggagc gtatgcaata actaaagacg gagtatttgc tacgatagta    300
gcgaaagtaa aatccggagc acctaacgga ctcagtgtaa tcaaatttgt agaagtaggc   360
ggatttgcga acaatgacct tgtagaacag aggacacagt tctttgacgg tggagtaaat   420
gttggagata ta                                                       432
```

<210> SEQ ID NO 79
<211> LENGTH: 144
<212> TYPE: PRT
<213> ORGANISM: Artificial Sequence
<220> FEATURE:
<223> OTHER INFORMATION: Polypeptide

<400> SEQUENCE: 79

```
Ile Lys Ile Lys Val Asp Thr Val Asn Ala Lys Pro Gly Asp Thr Val
1               5                   10                  15

Asn Ile Pro Val Arg Phe Ser Gly Ile Pro Ser Lys Gly Ile Ala Asn
            20                  25                  30

Cys Asp Phe Val Tyr Ser Tyr Asp Pro Asn Val Leu Glu Ile Ile Glu
        35                  40                  45

Ile Lys Pro Gly Glu Leu Ile Val Asp Pro Asn Pro Asp Lys Ser Phe
    50                  55                  60
```

Asp Thr Ala Val Tyr Pro Asp Arg Lys Ile Ile Val Phe Leu Phe Ala
 65                  70                  75                  80

Glu Asp Ser Gly Thr Gly Ala Tyr Ala Ile Thr Lys Asp Gly Val Phe
                 85                  90                  95

Ala Thr Ile Val Ala Lys Val Lys Ser Gly Ala Pro Asn Gly Leu Ser
            100                 105                 110

Val Ile Lys Phe Val Glu Val Gly Phe Ala Asn Asn Asp Leu Val
        115                 120                 125

Glu Gln Arg Thr Gln Phe Phe Asp Gly Val Asn Val Gly Asp Ile
    130                 135                 140

<210> SEQ ID NO 80
<211> LENGTH: 588
<212> TYPE: DNA
<213> ORGANISM: Artificial Sequence
<220> FEATURE:
<223> OTHER INFORMATION: Polynucleotide

<400> SEQUENCE: 80
atggcaaata caccggtatc aggcaatttg aaggttgaat ctacaacag caatccttca     60 gatactacta actcaatcaa tcctcagttc aaggttacta ataccggaag cagtgcaatt    120
gatttgtcca aactcacatt gagatattat tatacagtag acggacagaa agatcagacc    180
ttctggtgtg accatgctgc aataatcggc agtaacggca gctacaacgg aattacttca    240
aatgtaaaag gaacatttgt aaaaatgagt tcctcaacaa taacgcaga cacctacctt     300 gaaataagct ttacaggcgg aactcttgaa ccgggtgcac atgttcagat acaaggtaga    360
tttgcaaaga atgactggag taactataca cagtcaaatg actactcatt caagtctgct    420
tcacagtttg ttgaatggga tcaggtaaca gcatacttga acggtgttct tgtatggggt    480
aaagaacccg gtggcagtgt agtaccatca acacagcctg taacaacacc acctgcaaca    540
acaaaaccac ctgcaacaac aataccgccg tcagatgatc cgaatgca                588

<210> SEQ ID NO 81
<211> LENGTH: 196
<212> TYPE: PRT
<213> ORGANISM: Artificial Sequence
<220> FEATURE:
<223> OTHER INFORMATION: Polypeptide

<400> SEQUENCE: 81

Met Ala Asn Thr Pro Val Ser Gly Asn Leu Lys Val Glu Phe Tyr Asn
  1               5                  10                  15

Ser Asn Pro Ser Asp Thr Thr Asn Ser Ile Asn Pro Gln Phe Lys Val
                 20                  25                  30

Thr Asn Thr Gly Ser Ser Ala Ile Asp Leu Ser Lys Leu Thr Leu Arg
             35                  40                  45

Tyr Tyr Tyr Thr Val Asp Gly Gln Lys Asp Gln Thr Phe Trp Cys Asp
     50                  55                  60

His Ala Ala Ile Ile Gly Ser Asn Gly Ser Tyr Asn Gly Ile Thr Ser
 65                  70                  75                  80

Asn Val Lys Gly Thr Phe Val Lys Met Ser Ser Ser Thr Asn Asn Ala
                 85                  90                  95

Asp Thr Tyr Leu Glu Ile Ser Phe Thr Gly Gly Thr Leu Glu Pro Gly
            100                 105                 110

Ala His Val Gln Ile Gln Gly Arg Phe Ala Lys Asn Asp Trp Ser Asn
        115                 120                 125

```
Tyr Thr Gln Ser Asn Asp Tyr Ser Phe Lys Ser Ala Ser Gln Phe Val
    130                 135                 140

Glu Trp Asp Gln Val Thr Ala Tyr Leu Asn Gly Val Leu Val Trp Gly
145                 150                 155                 160

Lys Glu Pro Gly Gly Ser Val Val Pro Ser Thr Gln Pro Val Thr Thr
                165                 170                 175

Pro Pro Ala Thr Thr Lys Pro Pro Ala Thr Thr Ile Pro Pro Ser Asp
            180                 185                 190

Asp Pro Asn Ala
        195

<210> SEQ ID NO 82
<211> LENGTH: 630
<212> TYPE: DNA
<213> ORGANISM: Artificial Sequence
<220> FEATURE:
<223> OTHER INFORMATION: Polynucleotide

<400> SEQUENCE: 82
atggcacacc atcaccatca ccatgcacca tcacccggca caaagctcgt tcctacatgg      60
ggcgatacaa actgcgacgg cgttgtaaat gttgctgacg tagtagttct taacagattc     120
ctcaacgatc ctacatattc taacattact gatcagggta aggttaacgc agacgttgtt     180
gatcctcagg ataagtccgg cgcagcagtt gatcctgcag cgtaaagct cacagtagct      240 gactctgagg caatcctcaa ggctatcgtt gaactcatca cacttcctca agcggtacct     300
accagcggcg gtggaaaccc cggtgggggc aaccccccg gtggcggcaa ccccccggt       360 ggcggtggct gcacggcgac gctgtccgcg ggccagcagt ggaacgaccg ctacaacctc     420
aacgtcaacg tcagcggctc caacaactgg accgtgaccg tgaacgttcc gtggccggcg     480
aggatcatcg ccacctggaa catccacgcc agctacccgg actcccagac cttggttgcc     540
cggcctaacg gcaacggcaa caactggggc atgacgatca tgcacaacgg caactggacg     600
tggcccacgg tgtcctgcag cgccaactag                                      630

<210> SEQ ID NO 83
<211> LENGTH: 209
<212> TYPE: PRT
<213> ORGANISM: Artificial Sequence
<220> FEATURE:
<223> OTHER INFORMATION: Polypeptide

<400> SEQUENCE: 83

Met Ala His His His His His Ala Pro Ser Pro Gly Thr Lys Leu
1               5                   10                  15

Val Pro Thr Trp Gly Asp Thr Asn Cys Asp Gly Val Val Asn Val Ala
                20                  25                  30

Asp Val Val Leu Asn Arg Phe Leu Asn Asp Pro Thr Tyr Ser Asn
            35                  40                  45

Ile Thr Asp Gln Gly Lys Val Asn Ala Asp Val Asp Pro Gln Asp
        50                  55                  60

Lys Ser Gly Ala Ala Val Asp Pro Ala Gly Val Lys Leu Thr Val Ala
65                  70                  75                  80

Asp Ser Glu Ala Ile Leu Lys Ala Ile Val Glu Leu Ile Thr Leu Pro
                85                  90                  95

Gln Ala Val Pro Thr Ser Gly Gly Asn Pro Gly Gly Gly Asn Pro
            100                 105                 110

Pro Gly Gly Gly Asn Pro Pro Gly Gly Gly Gly Cys Thr Ala Thr Leu
```

|  |  | 115 |  |  | 120 |  |  |  | 125 |  |  |
|--|--|--|--|--|--|--|--|--|--|--|--|

Ser Ala Gly Gln Gln Trp Asn Asp Arg Tyr Asn Leu Asn Val Asn Val
        130                 135                 140

Ser Gly Ser Asn Asn Trp Thr Val Thr Val Asn Val Pro Trp Pro Ala
145                 150                 155                 160

Arg Ile Ile Ala Thr Trp Asn Ile His Ala Ser Tyr Pro Asp Ser Gln
                165                 170                 175

Thr Leu Val Ala Arg Pro Asn Gly Asn Gly Asn Trp Gly Met Thr
            180                 185                 190

Ile Met His Asn Gly Asn Trp Thr Trp Pro Thr Val Ser Cys Ser Ala
            195                 200                 205

Asn

<210> SEQ ID NO 84
<211> LENGTH: 2883
<212> TYPE: DNA
<213> ORGANISM: Artificial Sequence
<220> FEATURE:
<223> OTHER INFORMATION: Polynucleotide

<400> SEQUENCE: 84

| atggcacacc atcaccatca ccatgccttc gcctgctcgg tggactacga cgactccaac | 60 |
|---|---|
| gactggggta gcgggttcgt cgccgaagtc aaggtgacca cgaaggcag cgaccccatc | 120 |
| cagaactggc aagtaggctg daccttcccc ggtaaccagc agatcaccaa cggctggaac | 180 |
| ggcgtgttca gccagagcgg cgccaacgtc accgtccgct accgggactg gaacccaat | 240 |
| atcgcccccg gagccaccat ctccttcggc ttccagggca cctacagcgg ctccaacgac | 300 |
| gccccgacca gcttcaccgt caacggcgtc acctgcagcg gatcccagcc cgccaacctg | 360 |
| ccgcccgatg tcaccctgac atccccggcc aacaactcga ccttcctggt caacgacccg | 420 |
| atcgagctga ccgcggtcgc ctccgacccc gacggctcga tcgaccgggt ggaattcgcc | 480 |
| gccgacaaca ccgtcatcgg catcgacacc acctccccct acagcttcac ctggacggac | 540 |
| gctgccgccg ctcctactc ggtgaccgcg atcgcctacg acgaccaggg agccaggacc | 600 |
| gtctccgctc ccatcgccat ccgagtgctg daccgggccg ccgtcatcgc ctcaccgccc | 660 |
| accgtccgcg tgccgcaggg cggcaccgcc gacttcgagg tgcggctgtc caaccagccc | 720 |
| tccggcaacg tcacggtcac cgtggcgcgc acgtcgggca gctccgacct gaccgtctcc | 780 |
| agcggctccc aactccagtt cacctccagc aactggaacc agccgcagaa ggtgaccatc | 840 |
| gcctccgctg caaacggcgg aaacctggcc gaggcggtct tcaccgtcag cgcccccggc | 900 |
| cacgactcgg ccgaggtgac ggtccgggag atcgacccga acaccagctc ctacgaccag | 960 |
| gccttcctgg agcagtacga gaagatcaag gaccccgcca cgggctactt cgccgaattc | 1020 |
| aacgggctcc tggtccccta ccactcggtg gagaccatga tcgtcgaggc tccggaccac | 1080 |
| ggccaccaga ccacgtccga ggcgttcagc tactacctgt ggctggaggc gtactacggc | 1140 |
| cgggtcaccg gtgactggaa gccgctccac gacgcctggg agtcgatgga gaccttcatc | 1200 |
| atccccggca ccaaggacca gccgaccaac tccgcctaca cccgaactc cccggcgacc | 1260 |
| tacatccccg agcagcccaa cgctgacggc tacccgtcgc ctctcatgaa caacgtcccg | 1320 |
| gtgggtcaag accgctcgc ccaggagctg agctccacct acgggaccaa cgagatctac | 1380 |
| ggcatgcact ggctgctcga cgtggacaac gtctacggct cgggttctg cggcgacggc | 1440 |
| accgacgacg ccccgcccta catcaacacc taccagcgtg gtgcgcgcga gtcggtgtgg | 1500 |

```
gagaccattc cgcacccgtc ctgcgacgac ttcacgcacg gcggccccaa cggctacctg    1560
gacctgttca ccgacgacca gaactacgcc aagcagtggc gctacaccaa cgcccccgac    1620
gctgacgcgc gggccgtcca ggtgatgttc tgggcgcacg aatgggccaa ggagcagggc    1680
aaggagaacg agatcgcggg cctgatggac aaggcgtcca agatgggcga ctacctccgg    1740
tacgcgatgt tcgacaagta cttcaagaag atcggcaact gcgtcggcgc cacctcctgc    1800
ccgggtggcc aaggcaagga cagcgcgcac tacctgctgt cctggtacta ctcctggggc    1860
ggctcgctcg acacctcctc tgcgtgggcg tggcgtatcg gctccagctc ctcgcaccag    1920
ggctaccaga acgtgctcgc tgcctacgcg ctctcgcagg tgcccgaact gcagcctgac    1980
tccccgaccg gtgtccagga ctgggccacc agcttcgacc gccagttgga gttcctccag    2040
tggctgcagt ccgctgaagg tggtatcgcc ggtggcgcca ccaacagctg aagggaagc    2100 tacgacaccc cgccgaccgg cctgtcgcag ttctacggca tgtactacga ctggcagccg    2160
gtctggaacg acccgccgtc caacaactgg ttcggcttcc aggtctggaa catggagcgc    2220
gtcgcccagc tctactacgt gaccggcgac gcccggggcc aggccatcct cgacaagtgg    2280
gtgccgtggg ccatccagca caccgacgtg gacgccgaca acggcggcca gaacttccag    2340
gtcccctccg acctggagtg gtcgggccag cctgacacct ggaccggcac ctacaccggc    2400
aacccgaacc tgcacgtcca ggtcgtctcc tacagccagg acgtcggtgt gaccgccgct    2460
ctggccaaga ccctgatgta ctacgcgaag cgttcgggcg acaccaccgc cctcgccacc    2520
gcggagggtc tgctggacgc cctgctggcc caccgggaca gcatcggtat cgccacccc    2580 gagcagccga gctgggaccg tctggacgac ccgtgggacg ctccgaggg cctgtacgtg    2640 ccgccgggct ggtcgggcac catgcccaac ggtgaccgca tcgagccggg cgcgaccttc    2700
ctgtccatcc gctcgttcta caagaacgac ccgctgtggc cgcaggtcga ggcacacctg    2760
aacgacccgc agaacgtccc ggcgccgatc gtggagcgcc accgcttctg ggctcaggtg    2820
gaaatcgcga ccgcgttcgc agcccacgac gaactgttcg gggccggagc tcctactagt    2880
taa                                                                  2883
```

<210> SEQ ID NO 85
<211> LENGTH: 960
<212> TYPE: PRT
<213> ORGANISM: Artificial Sequence
<220> FEATURE:
<223> OTHER INFORMATION: Polypeptide

<400> SEQUENCE: 85

```
Met Ala His His His His His His Ala Phe Ala Cys Ser Val Asp Tyr
1               5                   10                  15

Asp Asp Ser Asn Asp Trp Gly Ser Gly Phe Val Ala Glu Val Lys Val
            20                  25                  30

Thr Asn Glu Gly Ser Asp Pro Ile Gln Asn Trp Gln Val Gly Trp Thr
        35                  40                  45

Phe Pro Gly Asn Gln Gln Ile Thr Asn Gly Trp Asn Gly Val Phe Ser
    50                  55                  60

Gln Ser Gly Ala Asn Val Thr Val Arg Tyr Pro Asp Trp Asn Pro Asn
65                  70                  75                  80

Ile Ala Pro Gly Ala Thr Ile Ser Phe Gly Phe Gln Gly Thr Tyr Ser
                85                  90                  95

Gly Ser Asn Asp Ala Pro Thr Ser Phe Thr Val Asn Gly Val Thr Cys
            100                 105                 110
```

-continued

```
Ser Gly Ser Gln Pro Ala Asn Leu Pro Pro Asp Val Thr Leu Thr Ser
        115                 120                 125
Pro Ala Asn Asn Ser Thr Phe Leu Val Asn Asp Pro Ile Glu Leu Thr
130                 135                 140
Ala Val Ala Ser Asp Pro Asp Gly Ser Ile Asp Arg Val Glu Phe Ala
145                 150                 155                 160
Ala Asp Asn Thr Val Ile Gly Ile Asp Thr Thr Ser Pro Tyr Ser Phe
                165                 170                 175
Thr Trp Thr Asp Ala Ala Gly Ser Tyr Ser Val Thr Ala Ile Ala
                180                 185                 190
Tyr Asp Asp Gln Gly Ala Arg Thr Val Ser Ala Pro Ile Ala Ile Arg
                195                 200                 205
Val Leu Asp Arg Ala Ala Val Ile Ala Ser Pro Pro Thr Val Arg Val
        210                 215                 220
Pro Gln Gly Gly Thr Ala Asp Phe Glu Val Arg Leu Ser Asn Gln Pro
225                 230                 235                 240
Ser Gly Asn Val Thr Val Thr Val Ala Arg Thr Ser Gly Ser Ser Asp
                245                 250                 255
Leu Thr Val Ser Ser Gly Ser Gln Leu Gln Phe Thr Ser Ser Asn Trp
                260                 265                 270
Asn Gln Pro Gln Lys Val Thr Ile Ala Ser Ala Asp Asn Gly Gly Asn
                275                 280                 285
Leu Ala Glu Ala Val Phe Thr Val Ser Ala Pro Gly His Asp Ser Ala
        290                 295                 300
Glu Val Thr Val Arg Glu Ile Asp Pro Asn Thr Ser Ser Tyr Asp Gln
305                 310                 315                 320
Ala Phe Leu Glu Gln Tyr Glu Lys Ile Lys Asp Pro Ala Ser Gly Tyr
                325                 330                 335
Phe Arg Glu Phe Asn Gly Leu Leu Val Pro Tyr His Ser Val Glu Thr
                340                 345                 350
Met Ile Val Glu Ala Pro Asp His Gly His Gln Thr Thr Ser Glu Ala
        355                 360                 365
Phe Ser Tyr Tyr Leu Trp Leu Glu Ala Tyr Tyr Gly Arg Val Thr Gly
370                 375                 380
Asp Trp Lys Pro Leu His Asp Ala Trp Glu Ser Met Glu Thr Phe Ile
385                 390                 395                 400
Ile Pro Gly Thr Lys Asp Gln Pro Thr Asn Ser Ala Tyr Asn Pro Asn
                405                 410                 415
Ser Pro Ala Thr Tyr Ile Pro Glu Gln Pro Asn Ala Asp Gly Tyr Pro
                420                 425                 430
Ser Pro Leu Met Asn Asn Val Pro Val Gly Gln Asp Pro Leu Ala Gln
                435                 440                 445
Glu Leu Ser Ser Thr Tyr Gly Thr Asn Glu Ile Tyr Gly Met His Trp
        450                 455                 460
Leu Leu Asp Val Asp Asn Val Tyr Gly Phe Gly Phe Cys Gly Asp Gly
465                 470                 475                 480
Thr Asp Asp Ala Pro Ala Tyr Ile Asn Thr Tyr Gln Arg Gly Ala Arg
                485                 490                 495
Glu Ser Val Trp Glu Thr Ile Pro His Pro Ser Cys Asp Asp Phe Thr
                500                 505                 510
His Gly Gly Pro Asn Gly Tyr Leu Asp Leu Phe Thr Asp Asp Gln Asn
        515                 520                 525
Tyr Ala Lys Gln Trp Arg Tyr Thr Asn Ala Pro Asp Ala Asp Ala Arg
```

```
            530                 535                 540
Ala Val Gln Val Met Phe Trp Ala His Glu Trp Ala Lys Glu Gln Gly
545                 550                 555                 560

Lys Glu Asn Glu Ile Ala Gly Leu Met Asp Lys Ala Ser Lys Met Gly
                    565                 570                 575

Asp Tyr Leu Arg Tyr Ala Met Phe Asp Lys Tyr Phe Lys Lys Ile Gly
                580                 585                 590

Asn Cys Val Gly Ala Thr Ser Cys Pro Gly Gln Gly Lys Asp Ser
            595                 600                 605

Ala His Tyr Leu Leu Ser Trp Tyr Ser Trp Gly Gly Ser Leu Asp
        610                 615                 620

Thr Ser Ser Ala Trp Ala Trp Arg Ile Gly Ser Ser Ser His Gln
625                 630                 635                 640

Gly Tyr Gln Asn Val Leu Ala Ala Tyr Ala Leu Ser Gln Val Pro Glu
                    645                 650                 655

Leu Gln Pro Asp Ser Pro Thr Gly Val Gln Asp Trp Ala Thr Ser Phe
                    660                 665                 670

Asp Arg Gln Leu Glu Phe Leu Gln Trp Leu Gln Ser Ala Glu Gly Gly
                675                 680                 685

Ile Ala Gly Gly Ala Thr Asn Ser Trp Lys Gly Ser Tyr Asp Thr Pro
690                 695                 700

Pro Thr Gly Leu Ser Gln Phe Tyr Gly Met Tyr Tyr Asp Trp Gln Pro
705                 710                 715                 720

Val Trp Asn Asp Pro Pro Ser Asn Asn Trp Phe Gly Phe Gln Val Trp
                725                 730                 735

Asn Met Glu Arg Val Ala Gln Leu Tyr Tyr Val Thr Gly Asp Ala Arg
                740                 745                 750

Ala Glu Ala Ile Leu Asp Lys Trp Val Pro Trp Ala Ile Gln His Thr
                755                 760                 765

Asp Val Asp Ala Asp Asn Gly Gly Gln Asn Phe Gln Val Pro Ser Asp
                770                 775                 780

Leu Glu Trp Ser Gly Gln Pro Asp Thr Trp Thr Gly Thr Tyr Thr Gly
785                 790                 795                 800

Asn Pro Asn Leu His Val Gln Val Val Ser Tyr Ser Gln Asp Val Gly
                    805                 810                 815

Val Thr Ala Ala Leu Ala Lys Thr Leu Met Tyr Ala Lys Arg Ser
            820                 825                 830

Gly Asp Thr Thr Ala Leu Ala Thr Ala Glu Gly Leu Leu Asp Ala Leu
                835                 840                 845

Leu Ala His Arg Asp Ser Ile Gly Ile Ala Thr Pro Glu Gln Pro Ser
850                 855                 860

Trp Asp Arg Leu Asp Asp Pro Trp Asp Gly Ser Glu Gly Leu Tyr Val
865                 870                 875                 880

Pro Pro Gly Trp Ser Gly Thr Met Pro Asn Gly Asp Arg Ile Glu Pro
                885                 890                 895

Gly Ala Thr Phe Leu Ser Ile Arg Ser Phe Tyr Lys Asn Asp Pro Leu
                900                 905                 910

Trp Pro Gln Val Glu Ala His Leu Asn Asp Pro Gln Asn Val Pro Ala
            915                 920                 925

Pro Ile Val Glu Arg His Arg Phe Trp Ala Gln Val Glu Ile Ala Thr
        930                 935                 940

Ala Phe Ala Ala His Asp Glu Leu Phe Gly Ala Gly Ala Pro Thr Ser
945                 950                 955                 960
```

```
<210> SEQ ID NO 86
<211> LENGTH: 24
<212> TYPE: DNA
<213> ORGANISM: Artificial Sequence
<220> FEATURE:
<223> OTHER INFORMATION: Polynucleotide

<400> SEQUENCE: 86
ccatggcggg gaaaagttca ccag                                              24

<210> SEQ ID NO 87
<211> LENGTH: 26
<212> TYPE: DNA
<213> ORGANISM: Artificial Sequence
<220> FEATURE:
<223> OTHER INFORMATION: Polynucleotide

<400> SEQUENCE: 87
ggtaccttag ttacagtaat gcttcc                                            26
```